(12) United States Patent
Chiu et al.

(10) Patent No.: US 10,983,130 B2
(45) Date of Patent: *Apr. 20, 2021

(54) FLUORINATED POLYMER DOTS

(71) Applicant: University of Washington through its Center for Commercialization, Seattle, WA (US)

(72) Inventors: Daniel Chiu, Seattle, WA (US); Yong Zhang, Seattle, WA (US); Jiangbo Yu, Seattle, WA (US); Yu Rong, Seattle, WA (US)

(73) Assignee: University of Washington Through Its Center for Commercialization, Seattle, WA (US)

( * ) Notice: Subject to any disclaimer, the term of this patent is extended or adjusted under 35 U.S.C. 154(b) by 92 days.

This patent is subject to a terminal disclaimer.

(21) Appl. No.: 14/904,269

(22) PCT Filed: Jul. 11, 2014

(86) PCT No.: PCT/US2014/046387
§ 371 (c)(1),
(2) Date: Jan. 11, 2016

(87) PCT Pub. No.: WO2015/006714
PCT Pub. Date: Jan. 15, 2015

(65) Prior Publication Data
US 2016/0131659 A1     May 12, 2016

Related U.S. Application Data

(60) Provisional application No. 61/845,297, filed on Jul. 11, 2013, provisional application No. 61/879,630, filed on Sep. 18, 2013.

(51) Int. Cl.
| | | |
|---|---|---|
| *G01N 33/58* | (2006.01) | |
| *C08G 75/32* | (2006.01) | |
| *B82Y 15/00* | (2011.01) | |
| *B82Y 20/00* | (2011.01) | |

(52) U.S. Cl.
CPC ............ *G01N 33/582* (2013.01); *B82Y 15/00* (2013.01); *C08G 75/32* (2013.01); *B82Y 20/00* (2013.01); *Y10S 977/773* (2013.01); *Y10S 977/92* (2013.01)

(58) Field of Classification Search
CPC .............................. G01N 33/582; C08G 75/32
See application file for complete search history.

(56) References Cited

U.S. PATENT DOCUMENTS

| | | | |
|---|---|---|---|
| 9,382,473 B2 * | 7/2016 | Chiu | .............. B82Y 30/00 |
| 2011/0014473 A1 | 1/2011 | Ying et al. | |
| 2013/0053260 A1 | 2/2013 | Chen et al. | |

FOREIGN PATENT DOCUMENTS

| | | | | |
|---|---|---|---|---|
| JP | 2005314639 A | 11/2005 | | |
| JP | 2011500916 A | 1/2011 | | |
| JP | 2013091712 A | 5/2013 | | |
| JP | 2013517374 A | 5/2013 | | |
| WO | WO-2008094144 A1 | 8/2008 | | |
| WO | WO 2013/101902 A2 | 7/2013 | | |
| WO | WO-2013101902 A2 * | 7/2013 | ......... | A61K 49/0019 |
| WO | WO-2013101902 A3 | 1/2015 | | |
| WO | WO-2015006374 A1 * | 1/2015 | ............. | C09K 11/06 |

OTHER PUBLICATIONS

Zhang et al. Chem. Commun. 2013, 49, 8256-8258.*
Rong et al. ACS Nano, 2013, 7, 376-384.*
Zhang et al. Macromolecules 2012, 45, 5427-5435 (Year: 2012).*
Zhang et al. Chem. Commun. 2011, 47, 11026-11028 (Year: 2011).*
Liang et al. J. Am. Chem. Soc. 2009, 131, 7792-7799 (Year: 2009).*
International search report and written opinion dated Oct. 15, 2014 for PCT/US2014/046387.
Zhang, et al. Importance of having low-density functional groups for generating high-performance semiconducting polymer dots. ACS Nano. Jun. 26, 2012;6(6):5429-39. doi: 10.1021/nn301308w. Epub May 24, 2012.
Chan, et al. Development of ultrabright semiconducting polymer dots for ratiometric pH sensing. Anal Chem. Feb. 15, 2011;83(4):1448-55. doi: 10.1021/ac103140x. Epub Jan. 18, 2011.
Feng, et al. A convenient preparation of multi-spectral microparticles by bacteria-mediated assemblies of conjugated polymer nanoparticles for cell imaging and barcoding. Adv Mater. Feb. 2, 2012;24(5):637-41. doi: 10.1002/adma.201102026. Epub Sep. 20, 2011.
Howes, et al. Phospholipid encapsulated semiconducting polymer nanoparticles: their use in cell imaging and protein attachment. J Am Chem Soc. Mar. 24, 2010;132(11):3989-96. doi: 10.1021/ja1002179.
Kim, et al. Conjugated polymer nanoparticles for biomedical in vivo imaging. Chem Commun (Camb). Mar. 14, 2010;46(10):1617-9. doi: 10.1039/b923309a. Epub Jan. 12, 2010.
Li, et al. Conjugated Polymer Based Nanoparticles as Dual-Modal Probes for Targeted In Vivo Fluorescence and Magnetic Resonance Imaging. Advanced Functional Materials. Aug. 2012; 22(15):3107-3115.
Li, et al. Polymer encapsulated conjugated polymer nanoparticles for fluorescence bioimaging. Journal of Materials Chemistry. Nov. 2011; 22(4):1257-1264.
Lim, et al. Fluorous biphase synthesis of a poly(p-phenyleneethynylene) and its fluorescent aqueous fluorous-phase emulsion. Angew Chem Int Ed Engl. Oct. 4, 2010;49(41):7486-8. doi: 10.1002/anie.201003111.
Liu, et al. Green light-emitting polyfluorenes with improved color purity incorporated with 4,7-diphenyl-2,1,3-benzothiadiazole moieties. Journal of Materials Chemistry. Apr. 2007; 17(27):2832-2838.
Pecher, et al. Nanoparticles of conjugated polymers. Chem Rev. Oct. 13, 2010;110(10):6260-79. doi: 10.1021/cr100132y.

(Continued)

*Primary Examiner* — Matthew P Coughlin
(74) *Attorney, Agent, or Firm* — Christensen O'Connor Johnson Kindness PLLC

(57) ABSTRACT

This disclosure provides semiconducting polymer dots (Pdots) for use in a wide variety of applications. In particular, this disclosure provides Pdots that are halogenated, including fluorinated Pdots. This disclosure also provides methods for synthesizing Pdots and methods for using Pdots, such as for biological imaging.

10 Claims, 43 Drawing Sheets

(56) References Cited

OTHER PUBLICATIONS

Petkau, et al. Pre- and postfunctionalized self-assembled π-conjugated fluorescent organic nanoparticles for dual targeting. J Am Chem Soc. Oct. 26, 2011;133(42):17063-71. doi: 10.1021/ja2075345. Epub Sep. 30, 2011.
Price, et al.Fluorine substituted conjugated polymer of medium band gap yields 7% efficiency in polymer-fullerene solar cells. J Am Chem Soc. Mar. 30, 2011;133(12):4625-31. doi: 10.1021/ja1112595. Epub Mar. 4, 2011.
Rong, et al. Multicolor fluorescent semiconducting polymer dots with narrow emissions and high brightness. Acs Nano. 2013; 7(1)L376-384.
Schutze, et al. Fluorescent conjugated block copolymer nanoparticles by controlled mixing. Chem Commun (Camb). Feb. 18, 2012;48(15):2104-6. doi: 10.1039/c2cc17066c. Epub Jan. 13, 2012.
Tuncel, et al. Conjugated polymer nanoparticles. Nanoscale. Apr. 2010;2(4):484-94. doi: 10.1039/b9nr00374f. Epub Mar. 6, 2010.
Wu, et al. Bioconjugation of ultrabright semiconducting polymer dots for specific cellular targeting. J Am Chem Soc. Nov. 3, 2010;132(43):15410-7. doi: 10.1021/ja107196s.
Wu, et al. Design of highly emissive polymer dot bioconjugates for in vivo tumor targeting. Angew Chem Int Ed Engl. Apr. 4, 2011;50(15):3430-4. doi: 10.1002/anie.201007461. Epub Mar. 4, 2011.
Wu, et al. Highly fluorescent semiconducting polymer dots for biology and medicine. Angew Chem Int Ed Engl. Mar. 11, 2013;52(11):3086-109. doi: 10.1002/anie.201205133. Epub Jan. 10, 2013.
Wu, et al. Multicolor conjugated polymer dots for biological fluorescence imaging. ACS Nano. Nov. 25, 2008;2(11):2415-23. doi: 10.1021/nn800590n.
Wu, et al. Ultrabright and bioorthogonal labeling of cellular targets using semiconducting polymer dots and click cAngew Chem Int Ed Engl. Dec. 3, 2010;49(49):9436-40. doi: 10.1002/anie.201004260. hemistry.
Ye, et al. A compact and highly fluorescent orange-emitting polymer dot for specific subcellular imaging. Chem Commun (Camb). Feb. 7, 2012;48(12):1778-80. doi: 10.1039/c2cc16486h. Epub Jan. 4, 2012.
Yu, et al. Nanoscale 3D tracking with conjugated polymer nanoparticles. J Am Chem Soc. Dec. 30, 2009;131(51):18410-4. doi: 10.1021/ja907228q.
Yu, et al. Stable functionalization of small semiconducting polymer dots via covalent cross-linking and their application for specific cellular imaging. Adv Mater. Jul. 10, 2012;24(26):3498-504. doi: 10.1002/adma.201201245. Epub Jun. 11, 2012.
Zhang, et al. Highly luminescent, fluorinated semiconducting polymer dots for cellular imaging and analysis. Chem Commun (Camb). Sep. 25, 2013;49(74):8256-8. doi: 10.1039/c3cc44048f.
Zhang, et al. Increased open circuit voltage in fluorinated benzothiadiazole-based alternating conjugated polymers. Chem Commun (Camb). Oct. 21, 2011;47(39):11026-8. doi: 10.1039/c1cc14586j. Epub Sep. 12, 2011.
Zhang, et al. Significant Improved Performance of Photovoltaic Cells Made from a Partially Fluorinated Cyclopentadithiophene/Benzothiadiazole Conjugated Polymer. Macromolecules. Jun. 2012; 45(13):5427-5435.
Extended European search report and opinion dated Feb. 8, 2017 for EP Application No. 14822204.
CN 201480049947.X First Office Action dated Feb. 2, 2018 (w/ English translation).
Hermanson. Chapter 4: Zero-Length Crosslinkers. Bioconjugate Techniques. Acad. Press, 2013.
"JP 2016-525815 Office Action dated Apr. 5, 2018 (w/ English translation)".
CN 201480049947.X Second Office Action dated Nov. 1, 2018 (w/ English translation).
Third Chinese Office Action dated Jun. 4, 2019, issued in corresponding Chinese Application No. 201480049947.X, filed Jul. 11, 2014, 39 pages.
Official Action from the European Patent Office dated Jul. 30, 2019, issued in corresponding European Application No. 14822204.5, filed Jul. 11, 2014, 4 pages.
Decision on Rejection dated Nov. 4, 2019, issued in corresponding Chinese Application No. 201480049947.X, filed Jul. 11, 2014, 69 pages.

* cited by examiner (a)

(b)

(a)

(b)

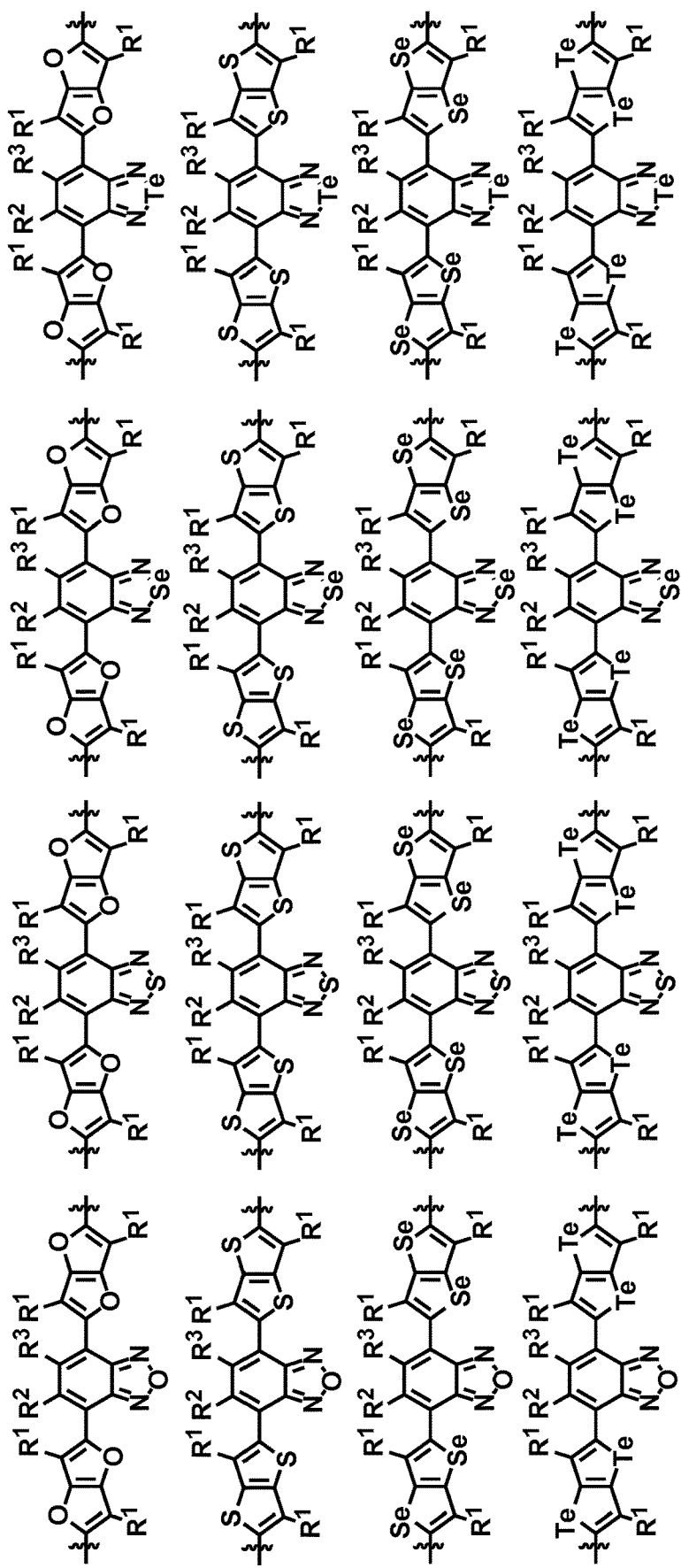
FIG. 21 (Cont. 1)

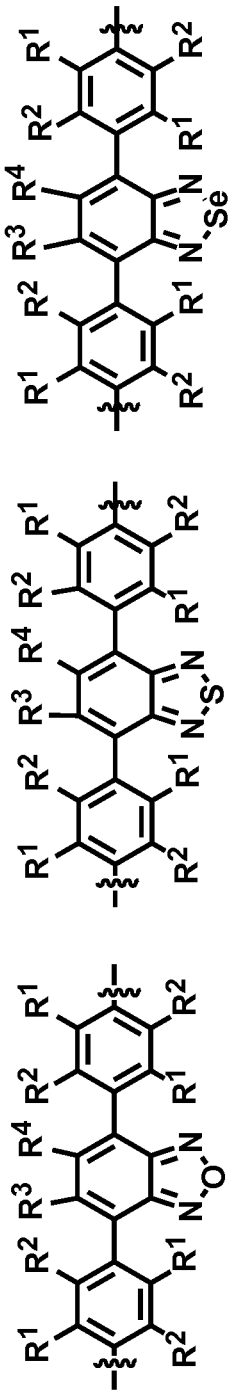
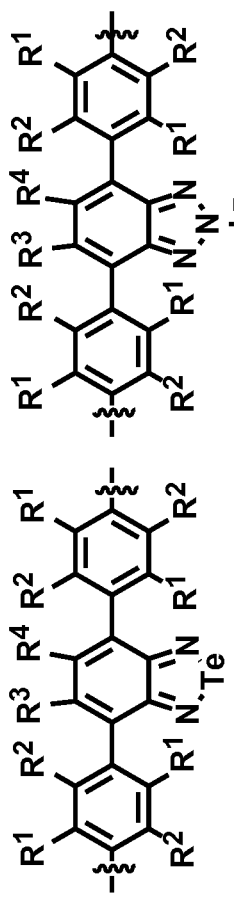
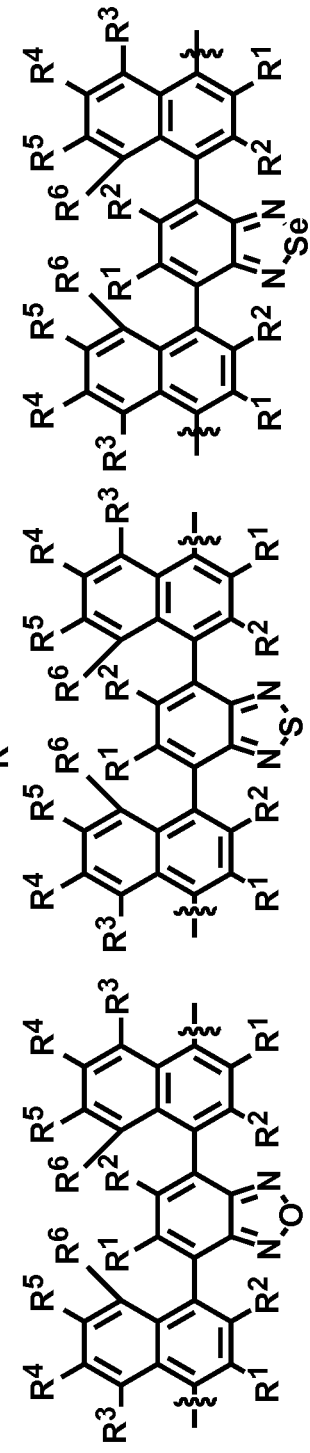
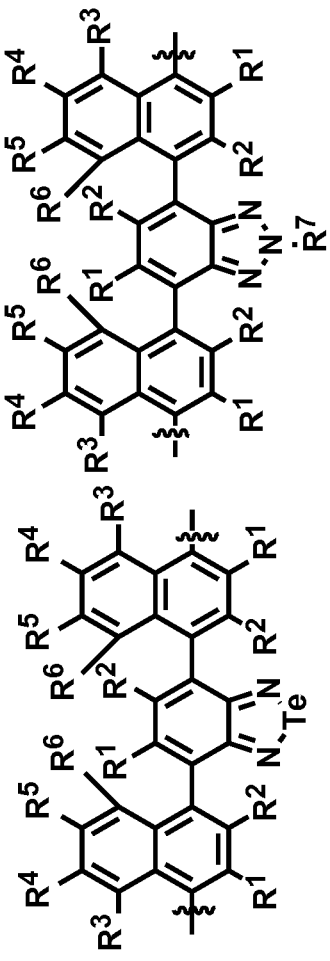
FIG. 21 (Cont. 2)

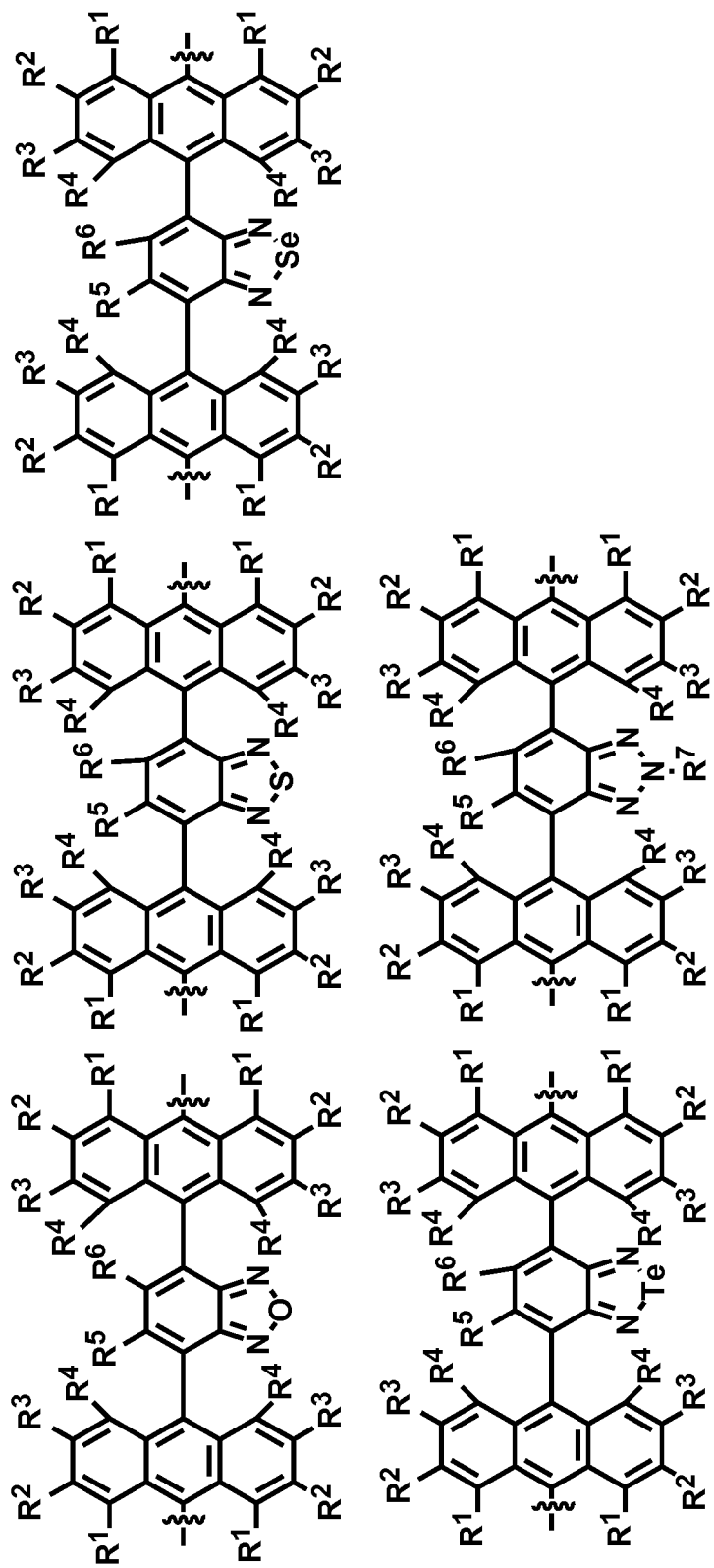
FIG. 21 (Cont. 3)

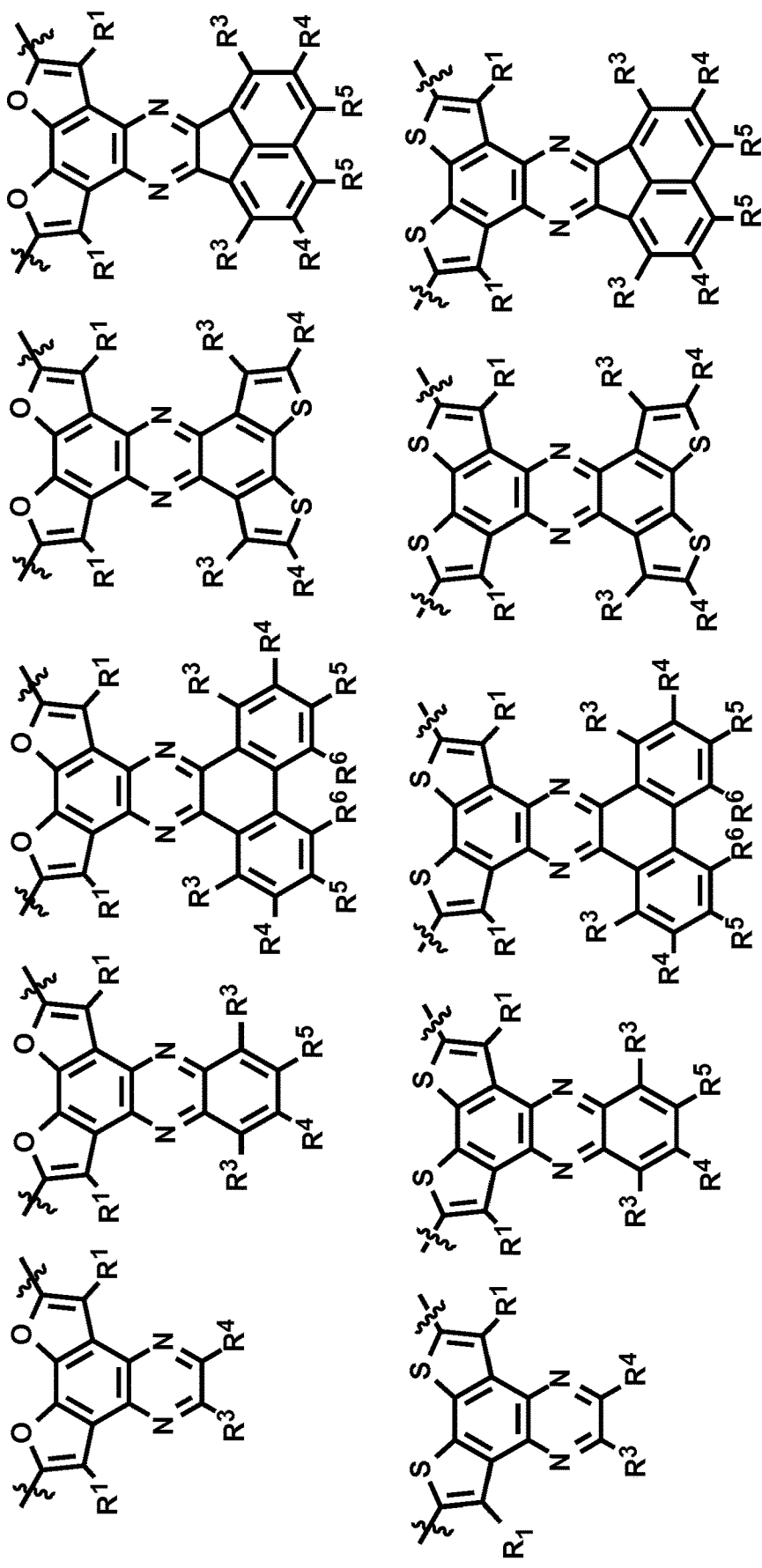
FIG. 22 (Cont. 1)

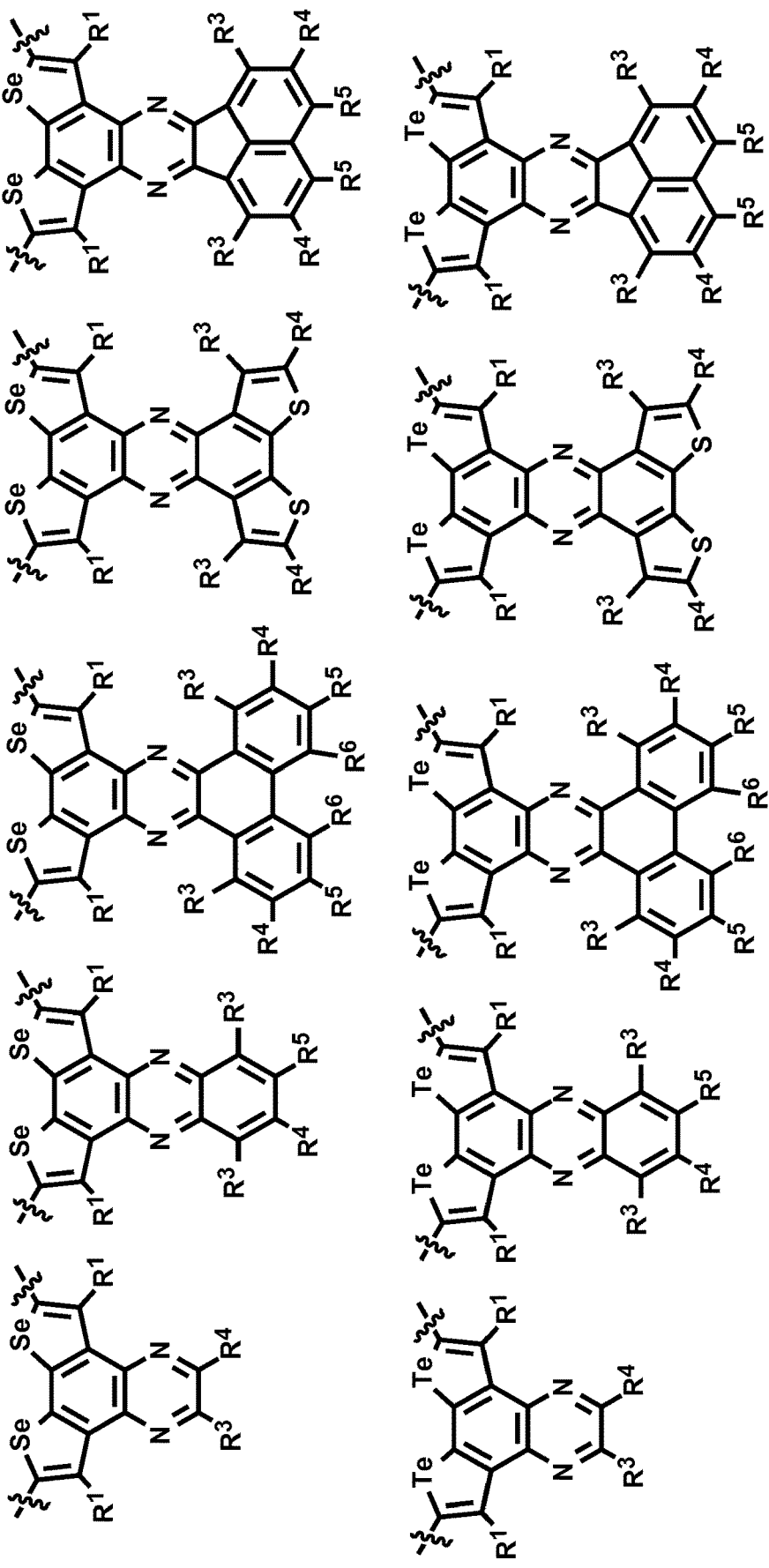
FIG. 22 (Cont. 2)

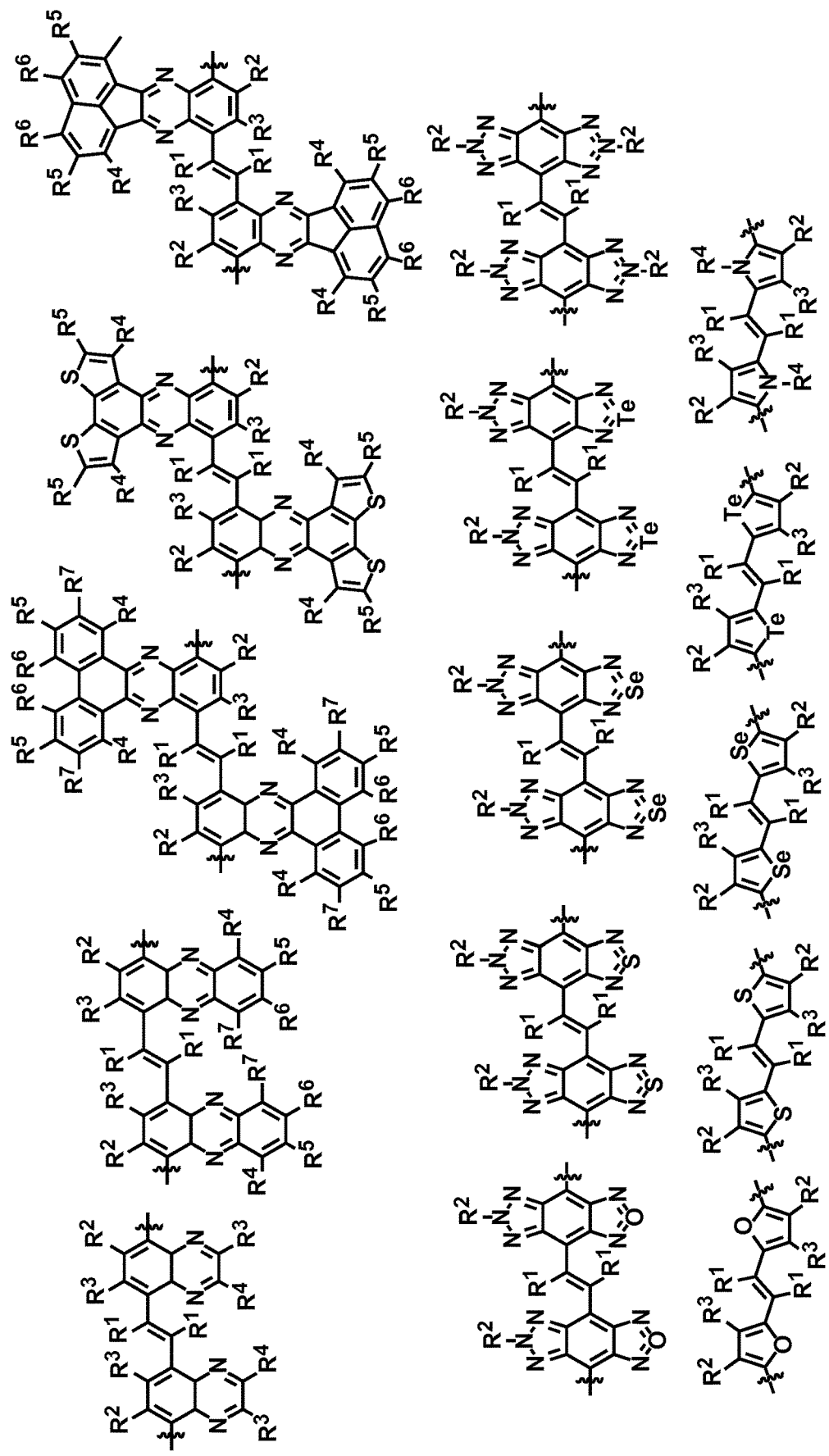
FIG. 24 (Cont. 1)

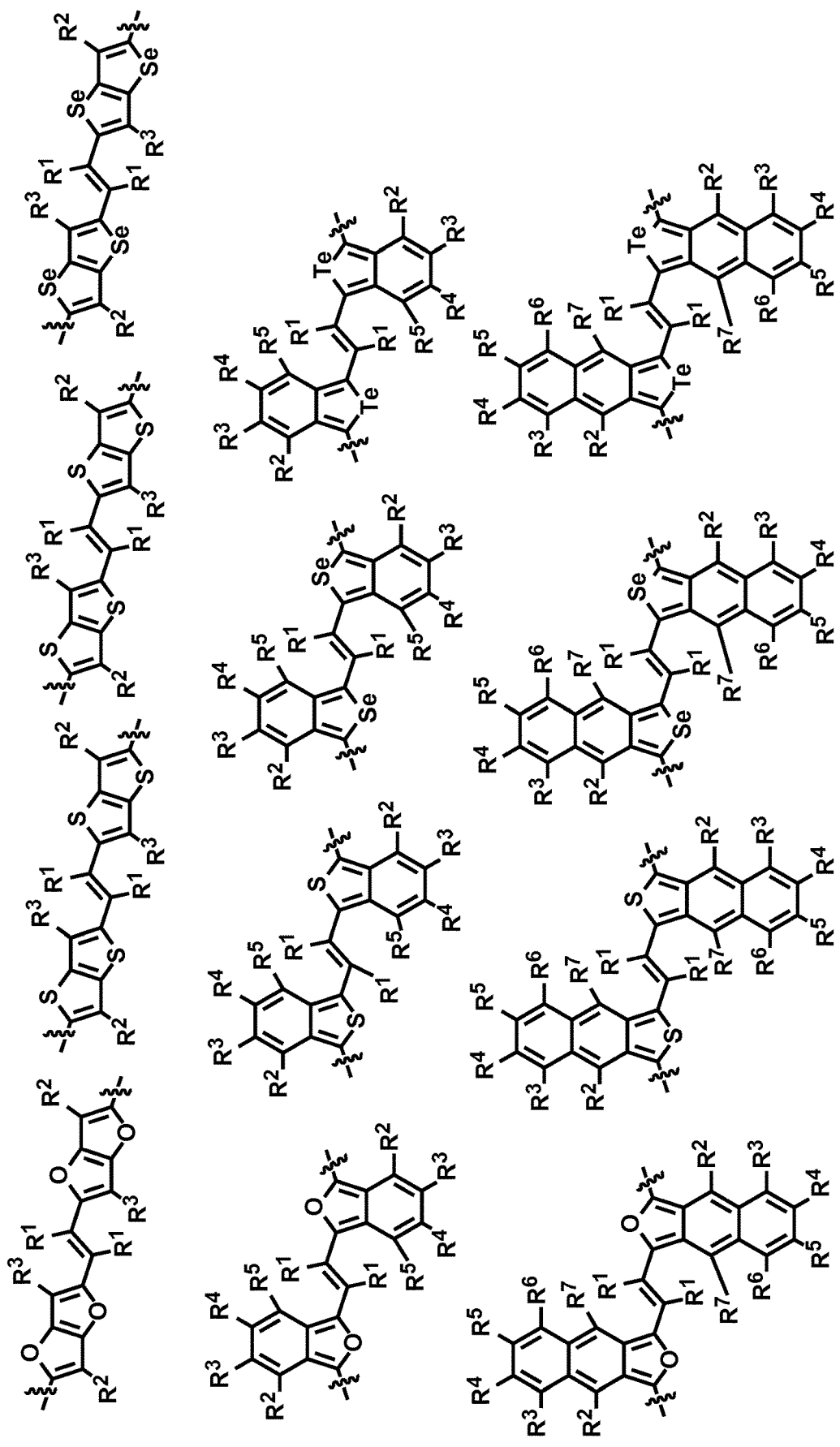
FIG. 24 (Cont. 2)

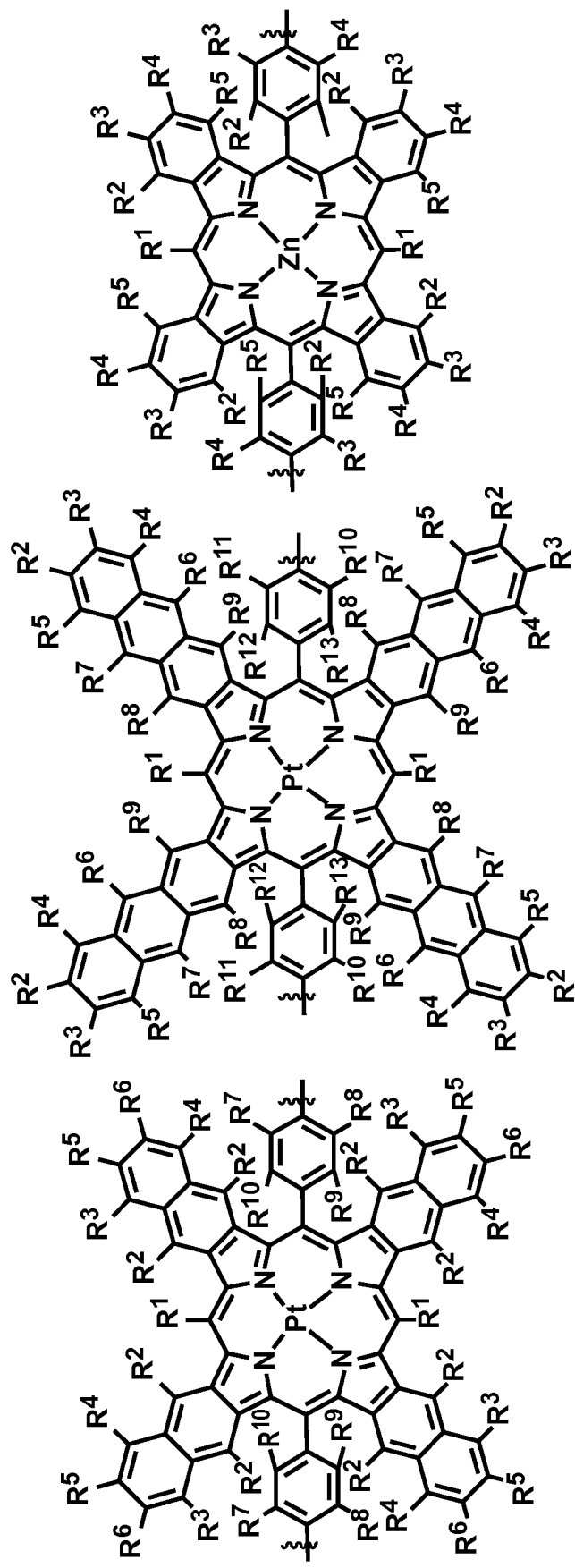
FIG. 26 (Cont. 1)

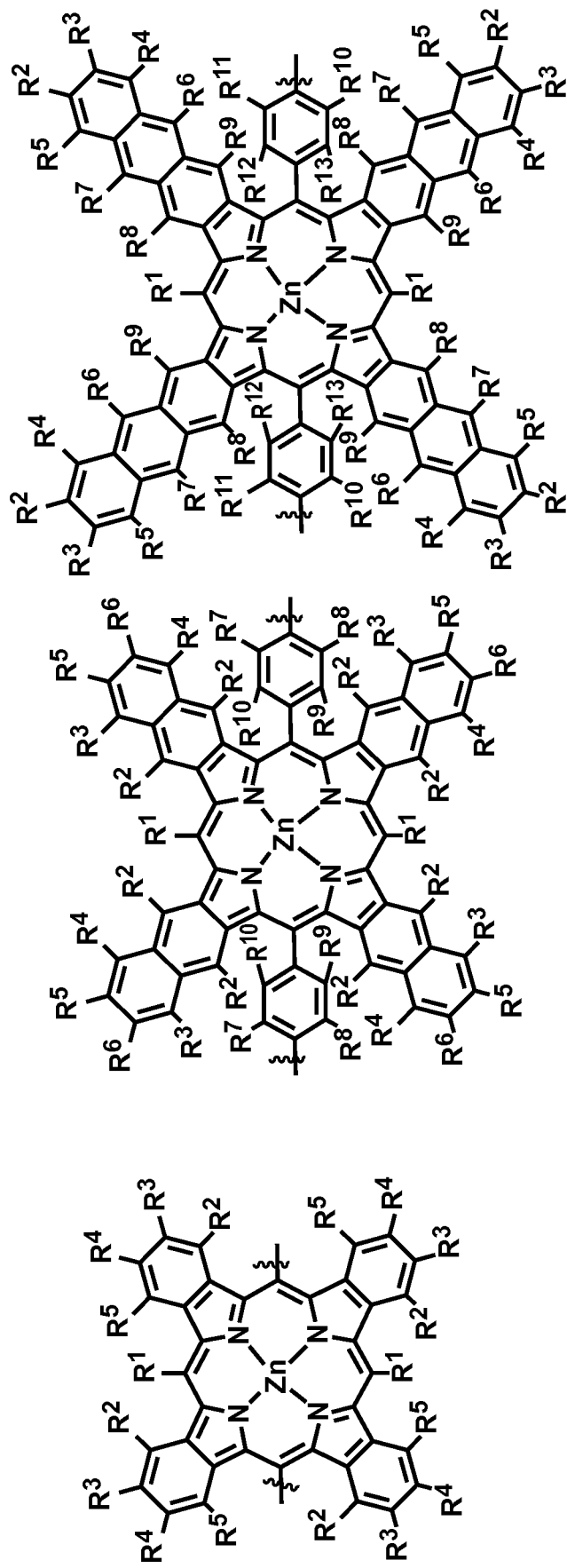
FIG. 26 (Cont. 2)

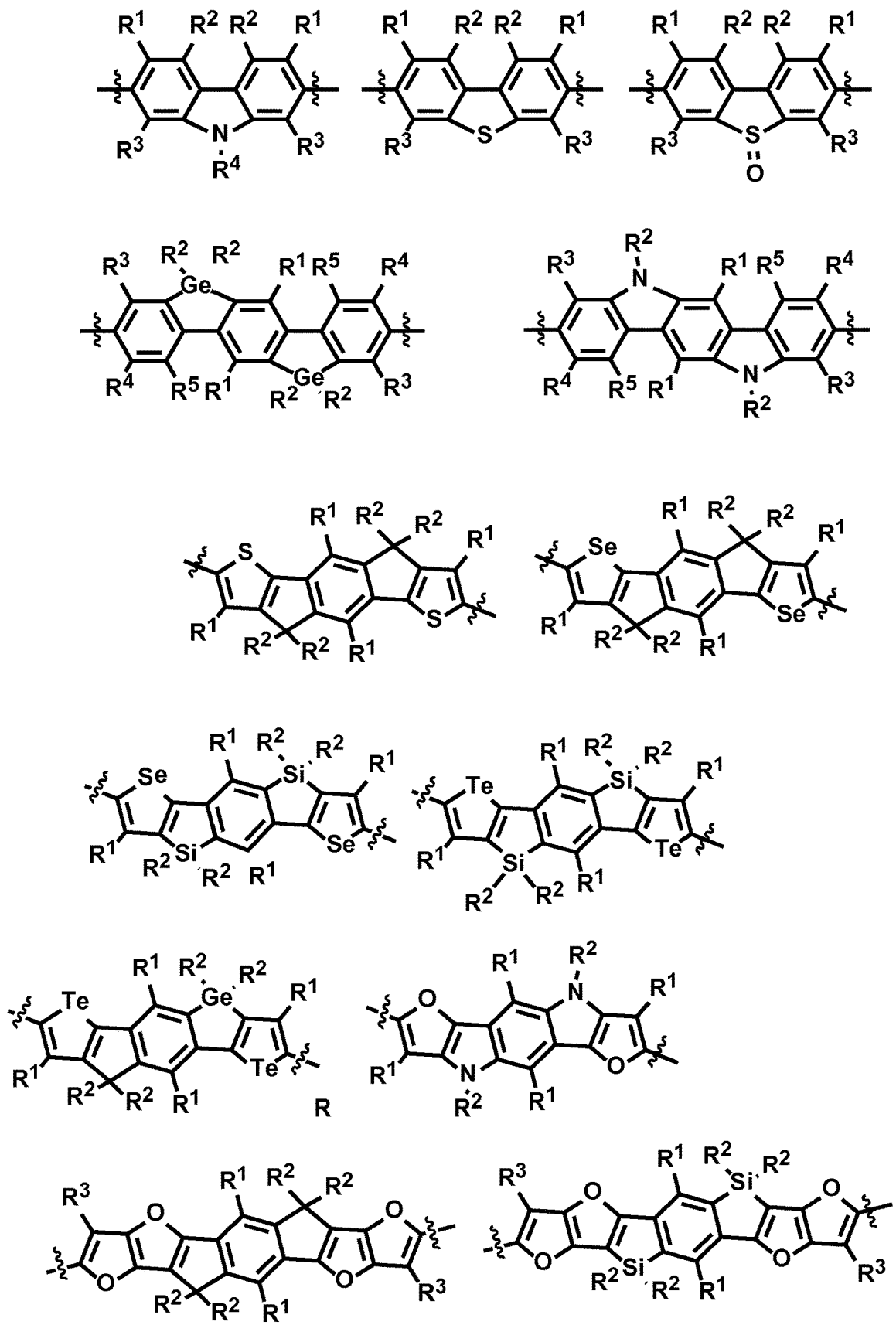
FIG. 28 (Cont. 1)

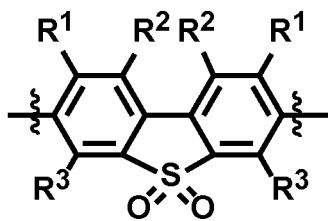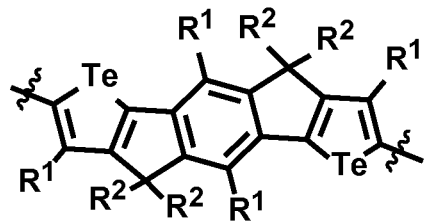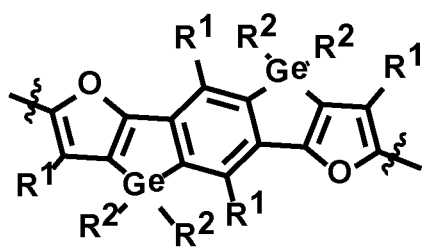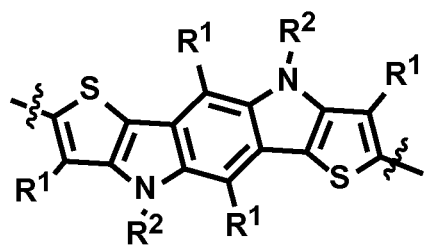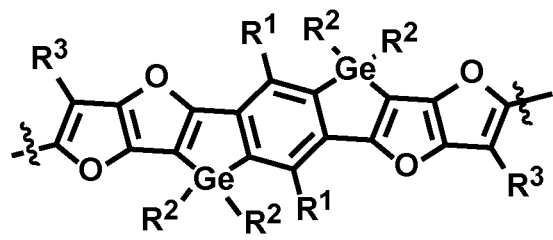
FIG. 28 (Cont. 2)

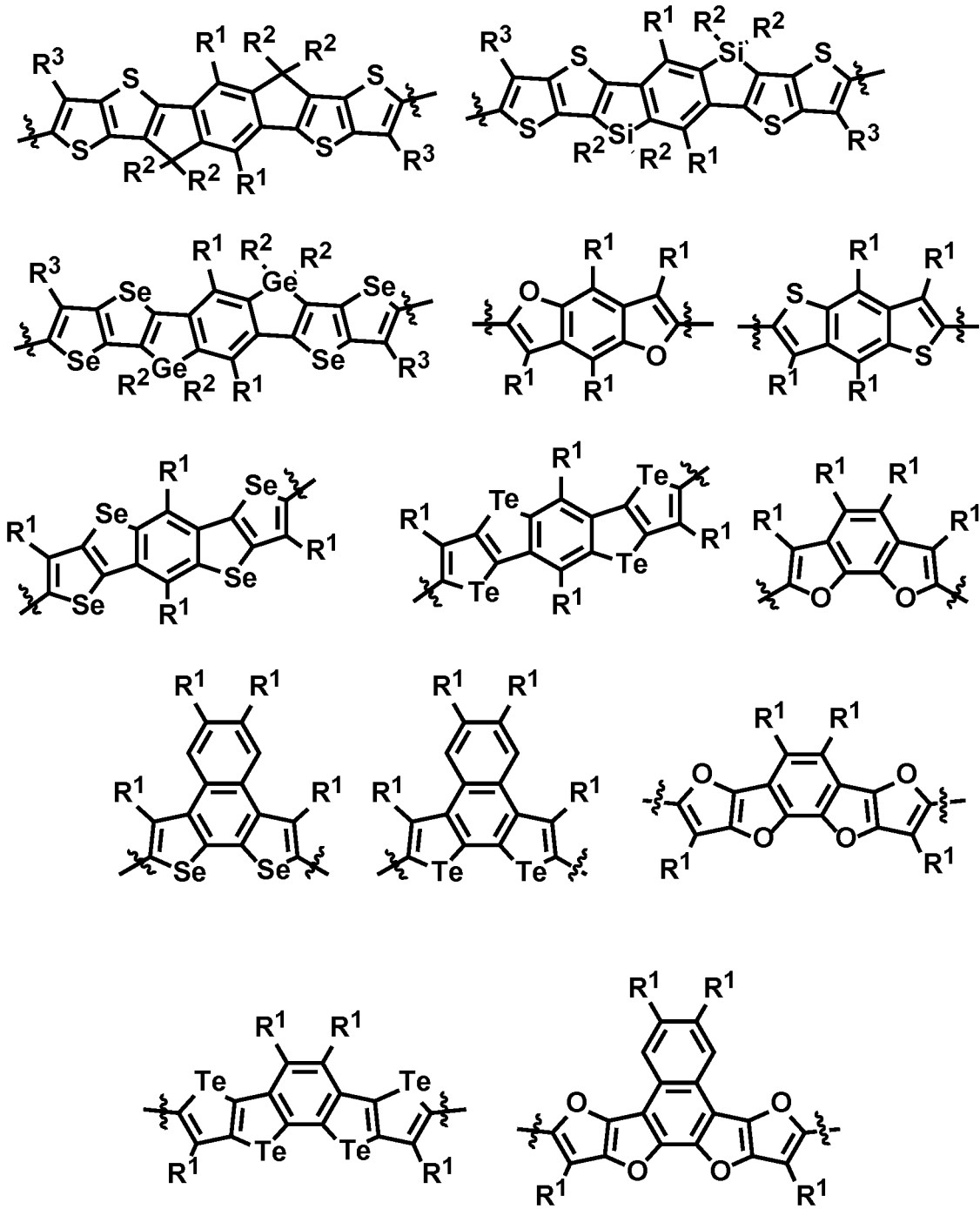
FIG. 28 (Cont. 3)

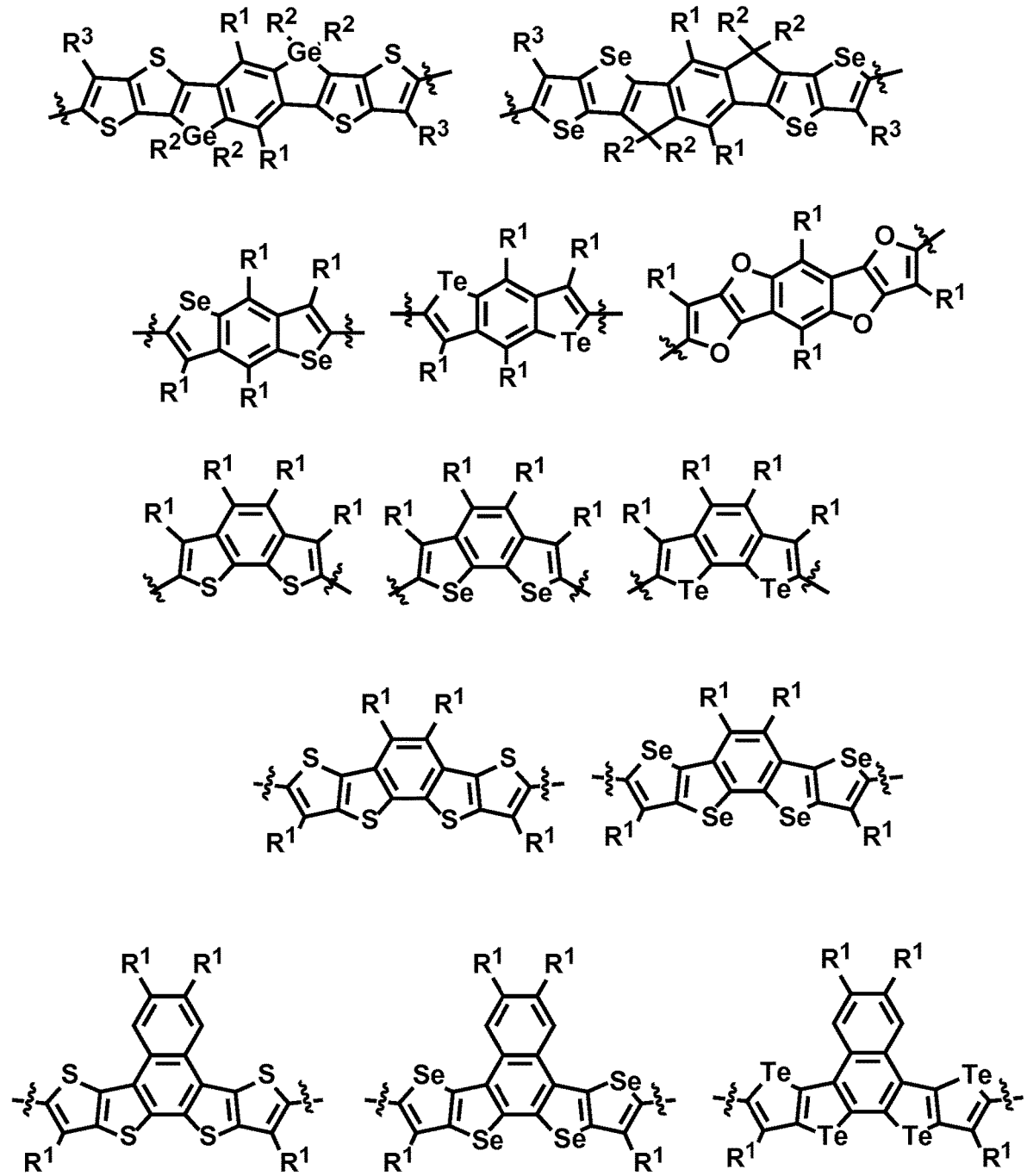
FIG. 28 (Cont. 4)

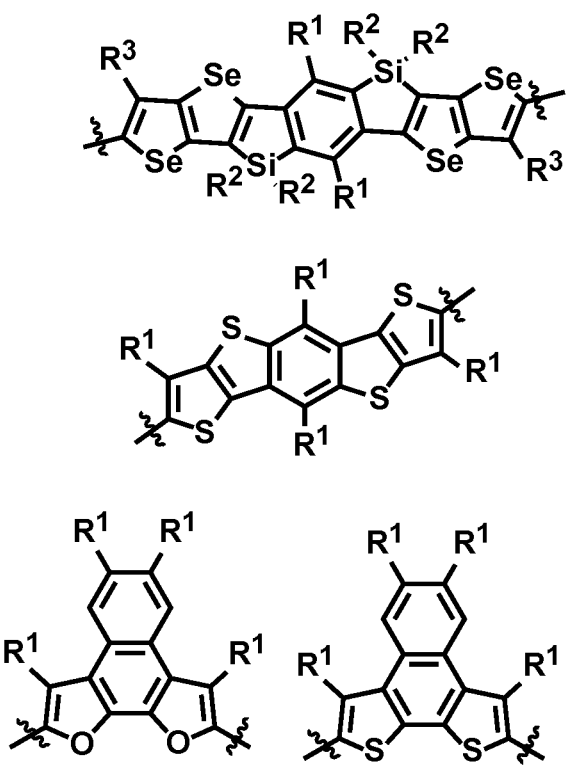
FIG. 28 (Cont. 5)

FLUORINATED POLYMER DOTS

CROSS-REFERENCE

This application is a U.S. National Phase Application under 35 U.S.C. § 371 of International Application No. PCT/US2014/046387, filed Jul. 11, 2014, which claims the benefit of U.S. Provisional Application Nos. 61/845,297, filed Jul. 11, 2013 and 61/879,630, filed Sep. 18, 2013, which applications are incorporated herein by reference in their entirety for all purposes.

STATEMENT AS TO FEDERALLY SPONSORED RESEARCH

This invention was made with government support under Grant No. W81XWH-11-1-0814 awarded by the Department of Defense and Grant No. GM085485 awarded by the National Institutes of Health. The government has certain rights in the invention.

BACKGROUND

Semiconducting polymer dots (Pdots) are nanometer-sized particles that often have good fluorescent properties. Pdots may be suitable for biological and biomedical applications, including in vitro and in vivo cellular imaging. Some characteristics of Pdots may include high photon-emission rates, tunable emission, and nontoxicity. Pdots may be synthesized using techniques such as nanoprecipitation.

SUMMARY

Described herein are methods and compositions for identifying an analyte in a sample, particularly using fluorinated semiconducting polymer dots. The composition may comprise a fluorinated semiconducting polymer dot wherein less than 50% of the total mass of the fluorinated semiconducting polymer dot is fluorine. The method may be used for identifying an analyte in a sample, the method further comprising; a) contacting the analyte with a fluorinated polymer dot, and b) detecting the polymer dot by irradiating the sample with a source of radiation.

In some cases, the composition may comprise a fluorinated polymer dot wherein a fluorine content of the fluorinated polymer dot is less than 50% of the total mass of the fluorinated polymer dot. This disclosure further provides compositions that may comprise a fluorinated polymer dot wherein nonspecific adsorption of the non-fluorinated polymer dot may be higher than nonspecific adsorption of the polymer dot of an analogous polymer dot that may be fluorinated. In some cases, a composition comprising a fluorinated polymer dot wherein the fluorinated polymer dot has a quantum yield that is greater than a quantum yield of an analogous polymer dot that is non-fluorinated is also provided herein. In some cases, the disclosure also provides for a composition comprising a fluorinated polymer dot wherein the fluorinated polymer dot has a non-spherical shape.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

DETAILED DESCRIPTION OF THE DISCLOSURE

Figure 1:
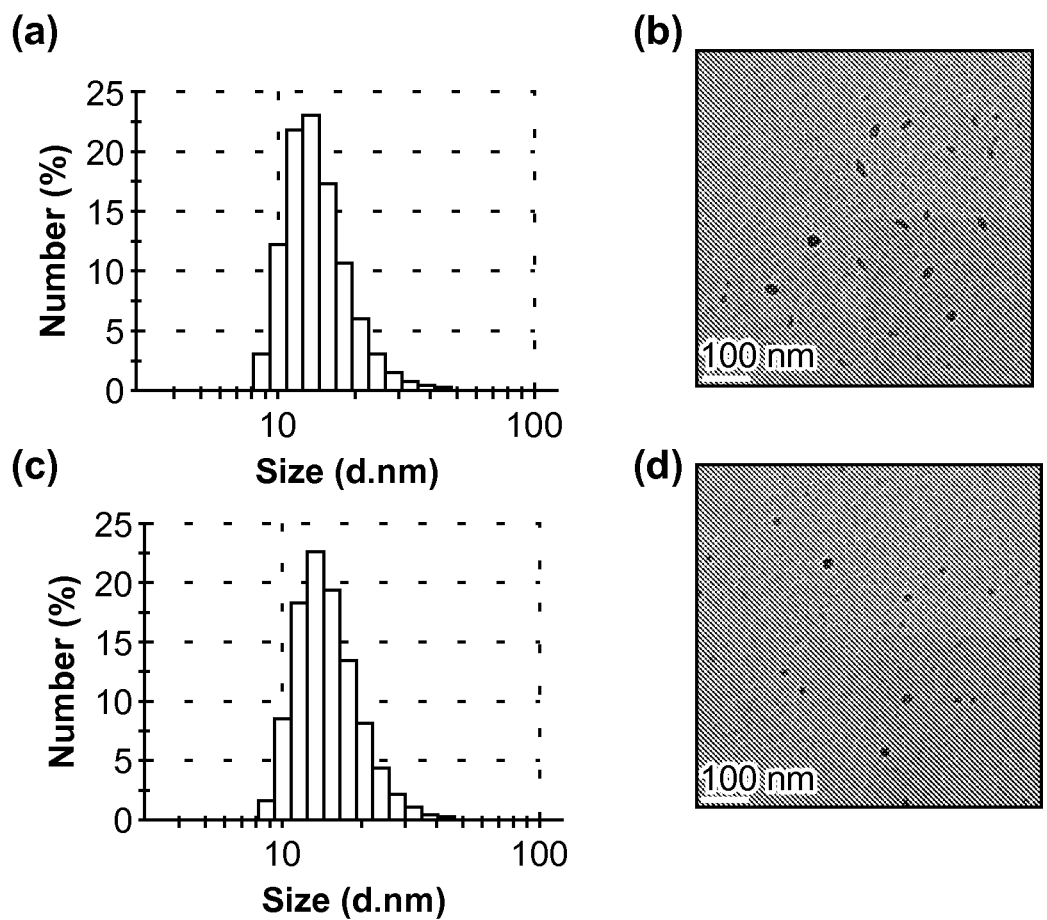
FIG. 1. The hydrodynamic diameter measured by dynamic light scattering and TEM images of (a, b) PFDPFBT and (c, d) PFDPBT Pdots.

The present disclosure relates to a new class of fluorescent nanoparticles, referred as fluorinated polymer dots and their biomolecular conjugates for a variety of biological applications. While not limited to any particular theory or concept, the present disclosure is based at least in-part on the concept that the fluorine content in the polymer dots can significantly improve the properties and performance of polymer dot in biological applications. For example, fluorine may influence the polymer properties by (1) affecting the polymer solubility as well as the nanoparticle preparation by nanoprecipitation method, (2) having a minimal effect on steric hindrance due to the small size of the fluorine atom, (3) being biocompatible, (4) increasing the quantum yield of the polymer both in solution and in the Pdot form, (5) reducing nonspecific labeling in biological applications as compared to the non-fluorinated polymer, (6) providing a micro-hydrophobic environment for blending and doping of different hydrophobic species, and (7) having a molar absorption coefficient that is higher than that of the non-fluorinated polymer.

This disclosure provides compositions of polymer dots made from polymers and particularly polymers with pi-conjugated structures. As used herein, "polymer" is a molecule composed of at least 2 repeating structural units typically connected by covalent chemical bonds. The repeating structural unit may be one type of monomer, and the resulting polymer is a homopolymer. In some cases, the polymers can include two different types of monomers, or three different types of monomers, or more types of monomers. Examples of monomers for synthesizing conjugated polymers include, but not limit to, benzene, fluorene, benzothiadiazole; thiophen, BODIPY; porphyrin, peryene, squaraine, and their derivatives. This disclosure also provides methods of using such polymers, methods of synthesizing such polymers, kits, and systems. A conjugated polymer may be in the shape of a dot. Conjugated polymer dots may also be referred to as Pdots. In some cases, halides (e.g., fluorine) are attached to or incorporated into the Pdot structure. The particle size of the Pdots may be comparable to that of a Qdot, for example, greater than 80% the size of a Qdot. The semiconducting polymers in Pdots may be present at a total volume that is at least 50% of the per-particle volume and preferably greater than 80%. The semiconducting polymers in Pdots may be present at a weight concentration that is at least 50% of the per-particle weight and preferably greater than 80%. Pdots can possess a hydrophobic polymer interior. In some cases, a Pdot has a halide (e.g., fluorine) content of less than 50% by mass. In some cases, the weight concentration is greater than 40%, 50%, 60%, 70%, 80%, 90% or 99%. In some cases, the weight concentration may be within the range of 40%-50%, 45%-55%, 50%-60%, 55%-65%, 60%-70%, 65%-75%, 70%-80%, 75%-85%, 80%-90%, 85%-95% or 90%-100%

Fluorinated Polymers and Polymer Dots

In some cases, the properties of conjugated polymers and/or Pdots provided in this disclosure can be significantly influenced by fluorine content. For example, the conjugated polymer may become insoluble in a general non-fluorous solvent when the content of fluorine is greater than 50% by mass. This disclosure, therefore, provides the composition of conjugated polymer with fluorine content less than 50% by mass, so that they can be easily prepared into fluorescent nanoparticles by nanoprecipitation method involving a general nonfluorous solvent such as tetrahydrofuran (THF). Often, the composition may comprise a fluorinated polymer dot wherein a fluorine content of the fluorinated polymer dot is less than 50% of the total mass of the fluorinated polymer dot.

In some cases, the fluorine content in the conjugated polymer is less than 50% by mass. In some cases, the fluorine content in the conjugated polymer is less than 45% by mass. In some cases, the fluorine content in the conjugated polymer is less than 40% by mass. In some cases, the fluorine content in the conjugated polymer is less than 35% by mass. In some cases, the fluorine content in the conjugated polymer is less than 30% by mass. In some cases, the fluorine content in the conjugated polymer is less than 25% by mass. In some cases, the fluorine content in the conjugated polymer is less than 20% by mass. In some cases, the fluorine content in the conjugated polymer is less than 15% by mass. In some cases, the fluorine content in the conjugated polymer is less than 10% by mass. In some cases, the fluorine content in the conjugated polymer is less than 5% by mass. In some cases, the fluorine content in the conjugated polymer is less than 4% by mass. In some cases, the fluorine content in the conjugated polymer is less than 3% by mass. In some cases, the fluorine content in the conjugated polymer is less than 2% by mass. In some cases, the fluorine content in the conjugated polymer is less than 1% by mass.

In some cases, the properties of conjugated polymers and/or Pdots in this disclosure can be significantly influenced by fluorine position, for example, in the polymer backbone or in the side chain of conjugated polymer. In some cases, the fluorine in the side chains of the conjugated polymer may affect the polymer solubility greater than the fluorine in polymer backbone. The fluorine in the polymer backbone can tune the Pdot properties such as the conjugation length, absorption, fluorescence, as well as nonspecific labeling of the Pdots. This disclosure, therefore, provides the composition of conjugated polymer with fluorine in the polymer backbone, so that they can be soluble in a nonfluorous solvent such as tetrahydrofuran (THF) for Pdot preparation.

Often, the fluorine is attached to a backbone of the polymer dot. In some cases, the fluorine is attached to a double bond of the polymer dot. In some cases, the fluorine is attached to an aromatic ring of the backbone of the polymer dot. In some cases, the fluorine content in the polymer backbone is less than 60% of the polymer by mass. In some cases, the fluorine content in the polymer backbone is less than 55% of the polymer by mass. In some cases, the fluorine content in the polymer backbone is less than 50% of the polymer by mass. In some cases, the fluorine content in the polymer backbone is less than 45% of the polymer by mass. In some cases, the fluorine content in the polymer backbone is less than 40% of the polymer by mass. In some cases, the fluorine content in the polymer backbone is less than 35% of the polymer by mass. In some cases, the fluorine content in the polymer backbone is less than 30% of the polymer by mass. In some cases, the fluorine content in the polymer backbone is less than 25% of the polymer by mass. In some cases, the fluorine content in the polymer backbone is less than 20% of the polymer by mass. In some cases, the fluorine content in the polymer backbone is less than 15% of the polymer by mass. In some cases, the fluorine content in the polymer backbone is less than 10% of the polymer by mass. In some cases, the fluorine content in the polymer backbone is less than 5% of the polymer by mass. In some cases, the fluorine content in the polymer backbone is less than 4% of the polymer by mass. In some cases, the fluorine content in the polymer backbone is less than 3% of the polymer by mass. In some cases, the fluorine content in the polymer backbone is less than 2% of the polymer by mass. In some cases, the fluorine content in the polymer backbone is less than 1% of the polymer by mass.

In some cases, the properties of conjugated polymers and/or Pdots in this disclosure can be significantly influenced by fluorine position in the polymer backbone. For example, the fluorine in the aromatic ring of the polymer backbone can tune the Pdot properties such as the conjugation length, absorption, fluorescence, as well as nonspecific labeling of the resulting Pdots. This disclosure includes the conjugated polymer with fluorine attached to the aromatic rings in the polymer backbone. In some cases, the fluorine content in aromatic ring is less than 50% of the polymer by mass. In some cases, the fluorine content in aromatic ring is less than 45% of the polymer by mass. In some cases, the fluorine content in aromatic ring is less than 40% of the polymer by mass. In some cases, the fluorine content in aromatic ring is less than 35% of the polymer by mass. In some cases, the fluorine content in aromatic ring is less than 30% of the polymer by mass. In some cases, the fluorine content in aromatic ring is less than 25% of the polymer by mass. In some cases, the fluorine content in aromatic ring is less than 20% of the polymer by mass. In some cases, the fluorine content in aromatic ring is less than 15% of the polymer by mass. In some cases, the fluorine content in aromatic ring is less than 10% of the polymer by mass. In some cases, the fluorine content in aromatic ring is less than 5% of the polymer by mass. In some cases, the fluorine content in aromatic ring is less than 4% of the polymer by mass. In some cases, the fluorine content in aromatic ring is less than 3% of the polymer by mass. In some cases, the fluorine content in aromatic ring is less than 2% of the polymer by mass. In some cases, the fluorine content in aromatic ring is less than 1% of the polymer by mass.

In some cases, the properties of conjugated polymers and/or Pdots in this disclosure can be significantly influenced by fluorine position in the polymer backbone. For example, the fluorine in the double bonds of the polymer backbone can tune the Pdot properties such as the conjugation length, absorption, fluorescence, as well as nonspecific labeling of the resulting Pdots. In some cases, the fluorine is mono-substituted. In some cases, the fluorine is di-substituted.

This disclosure includes the conjugated polymer with fluorine attached to the double bonds in the polymer backbone. In some cases, the fluorine content in double bonds is less than 50% of the polymer by mass. In some cases, the fluorine content in double bonds is less than 45% of the polymer by mass. In some cases, the fluorine content in double bonds is less than 40% of the polymer by mass. In some cases, the fluorine content in double bonds is less than 35% of the polymer by mass. In some cases, the fluorine content in double bonds is less than 30% of the polymer by mass. In some cases, the fluorine content in double bonds is less than 25% of the polymer by mass. In some cases, the fluorine content in double bonds is less than 20% of the polymer by mass. In some cases, the fluorine content in double bonds is less than 15% of the polymer by mass. In some cases, the fluorine content in double bonds is less than 10% of the polymer by mass. In some cases, the fluorine content in double bonds is less than 5% of the polymer by mass. In some cases, the fluorine content in double bonds is less than 4% of the polymer by mass. In some cases, the fluorine content in double bonds is less than 3% of the polymer by mass. In some cases, the fluorine content in double bonds is less than 2% of the polymer by mass. In some cases, the fluorine content in double bonds is less than 1% of the polymer by mass.

In some cases, the properties of conjugated polymers and/or Pdots in this disclosure can be significantly influenced by number of fluorine atoms in a repeating unit of the polymer backbone. For example, the number of fluorine atoms in the backbone repeating unit can tune the Pdot properties such as the conjugation length, absorption, fluorescence, as well as nonspecific labeling of the resulting Pdots. This disclosure includes the conjugated polymer with variable number of fluorine atoms attached to each backbone repeating unit. In some cases, each backbone repeating unit includes 1 fluorine atom. In some cases, each backbone repeating unit includes 2 fluorine atoms. In some cases, each backbone repeating unit includes 3 fluorine atoms. In some cases, each backbone repeating unit includes 4 fluorine atoms. In some cases, each backbone repeating unit includes 5 fluorine atoms. In some cases, each backbone repeating unit includes 6 fluorine atoms. In some cases, each backbone repeating unit includes 7 fluorine atoms. In some cases, each backbone repeating unit includes 8 fluorine atoms. In some cases, each backbone repeating unit includes 9 fluorine atoms. In some cases, each backbone repeating unit includes 10 fluorine atoms. In some cases, each backbone repeating unit includes 11 fluorine atoms. In some cases, each backbone repeating unit includes 12 fluorine atoms. In some cases, each backbone repeating unit includes 13 fluorine atoms. In some cases, each backbone repeating unit includes more than 5 fluorine atoms. However, the overall fluorine content in the polymer may be less than 50% of the polymer by mass.

In some cases, the fluorinated polymer dots include fluorinated conjugated polymer physically associated or chemically cross-linked with non-fluorinated polymers. The non-fluorinated polymer can be general fluorescent conjugated polymer or the optically-inert polymers such as polystyrene based polymers. The non-fluorinated polymer can be blended with the fluorinated polymer to form Pdots with desirable properties, for example increasing fluorescence quantum yield, reducing nonspecific adsorption in biological labeling, providing surface functional groups for bioconjugation, etc. The blending ratio of the non-fluorinated polymer relative the fluorinated polymer can vary from 1% to 99% by mass. In some cases, the blending ratio of the non-fluorinated polymer relative the fluorinated polymer varies can be greater than 10% by mass. In some cases, the blending ratio of the non-fluorinated polymer relative the fluorinated polymer varies can be greater than 20% by mass. In some cases, the blending ratio of the non-fluorinated polymer relative the fluorinated polymer varies can be greater than 30% by mass. In some cases, the blending ratio of the non-fluorinated polymer relative the fluorinated polymer varies can be greater than 40% by mass. In some cases, the blending ratio of the non-fluorinated polymer relative the fluorinated polymer varies can be greater than 50% by mass. In some cases, the blending ratio of the non-fluorinated polymer relative the fluorinated polymer varies can be greater than 60% by mass. In some cases, the blending ratio of the non-fluorinated polymer relative the fluorinated polymer varies can be greater than 70% by mass. In some cases, the blending ratio of the non-fluorinated polymer relative the fluorinated polymer varies can be greater than 80% by mass. In some cases, the blending ratio of the non-fluorinated polymer relative the fluorinated polymer varies can be greater than 90% by mass.

In some cases, a repeating subunit of a composition of the invention comprises no greater than 2 or no greater than 1 nitrogen atoms. In some cases, the repeating subunit has zero nitrogen atoms. The nitrogen atoms in a single repeating unit can be equivalent, inequivalent, symmetrical to one another, asymmetrical to one another, degenerate to one another, non-degenerate to one another, $sp^1$ hybridized, $sp^2$ hybridized, $sp^3$ hybridized, basic, neutral, have a localized electron pair, a delocalized electron pair, or have a single, double, or triple bond. A nitrogen atom can be bound to a hydrogen atom, a carbon atom, an oxygen atom, a sulfur atom, or another nitrogen atom. A nitrogen atom can be part of an aromatic, non-aromatic, saturated, or unsaturated ring.

Pdots may have certain characteristics such as a particular brightness, tunable emission, and a high photon emission rate. The Pdots may be able to resist photobleaching. In some cases, the Pdots may be non-toxic.

In some cases, the method provides for the synthesis of a highly fluorescent fluorinated semiconducting polymer dot (Pdot). The fluorinated Pdot can have a high quantum yield (e.g., up to 90%). The fluorinated Pdot may be brighter (e.g., up to 10 times) in cell-labeling applications than its non-fluorinated counterpart, and might have a unique shape (e.g., rod rather than spherical shape).

Pdots are useful for many detection and/or imaging applications. The detection and/or imaging applications may include single-cell labeling, multi-cell labeling, tissue labeling, organ labeling, in vitro labeling, and in vivo labeling. The detection and/or imaging of cells may include molecules expressed by the cells, such as, extracellular molecules or intracellular molecules. The detection and/or imaging may include molecules attached to the cells such as proteins, sugars, particulates. Cases of the present disclosure relate to the fluorinated polymer dots and their biomolecular conjugates for a variety of applications, including but not limited to flow cytometry, fluorescence activated sorting, immunofluorescence, immunohistochemistry, fluorescence multiplexing, single molecule imaging, single particle tracking, protein folding, protein rotational dynamics, DNA and gene analysis, protein analysis, metabolite analysis, lipid analysis, FRET based sensors, high throughput screening, cellular imaging, in vivo imaging, bioorthogonal labeling, click reactions, fluorescence-based biological assays such as immunoassays and enzyme-based assays (e.g., ELISA), western blot, and a variety of fluorescence techniques in biological assays and measurements.

The Pdots described herein can be used in a wide variety of applications including, medical diagnostics, medical prognostics, biological research, and water and soil testing. Similarly, the Pdots may be used to detect a wide variety of analytes, such as cells, microbes, bacteria, and viruses.

Polymer Structure

Polymer dots of the disclosure are pi-conjugated species with luminescent properties. The dots comprises polymers with one or more repeating units, which can be combined in fixed, ordered, or random configurations and ratios. A repeating unit can be a monomer or a chemical motif that occurs throughout the polymer, such as an aromatic or heterocyclic unit. The polymers can be halogenated, for example, fluorinated, chlorinated, brominated, or iodinated. A polymer, a repeating unit, or a monomer can be halogenated at one or multiple sites. A halogenated polymer, for example, a fluorinated polymer, can provide greater levels of fluorescence than can a non-halogenated analogous polymer.

A polymer, or a dot comprising the polymer, can be conjugated to another moiety with properties useful for therapy, diagnosis, imaging, or research. For example, a polymer or a dot can be conjugated to an additional moiety through a linker. The linker can be hydrophilic or hydrophobic. Non-limiting examples of linkers include a chemical bond, a small molecule, such as an amino acid, a functional group, such as an ester, and amide, a carbamate, an ether, an alkylene group, an alkenylene group, and alkynylene group, or an arylene group, or a polymer, such as a polyether, a polyester, a polyamide, a polycarbamate, a polyaryl, a polystyrene, or a polyolefin. In some cases, the linker is polyethylene glycol or polystyrene polyethylene glycol.

The polymer can be conjugated to a hydrophilic moiety, for example, a hydrophilic functional group. Non-limiting examples of hydrophilic functional groups include carboxyl groups, hydroxyl groups, amino groups, amido groups, sulfhydryl groups, sulfate groups phosphate groups, and any hydrogen bond donor or acceptor. The polymer can be conjugated to a biomolecule, for example, a peptide, protein, an aptamer, an antibody, an enzyme, carbohydrate, nucleic acid, deoxyribonucleic acid, ribonucleic acid, or lipid. In some cases, a polymer dot can be conjugated to a small molecule, a drug, a biomimetic, a pharmaceutical compound, an isotope, a radioisotope, or a chemical. In some cases, a polymer or dot is conjugated to streptavidin. In some cases, a polymer or dot is conjugated to biotin, or indirectly linked to biotin through streptavidin. In some cases, a polymer or dot is conjugated to a tag such as hemagglutanin (HA), vesicular stomatitis virus (VSV), glutathione S-transferase (GST), histadine, more than one histadine, six histadines (6×His) or c-myc.

The polymer can be conjugated to a reactive moiety, for example, an acid anhydride, an acid halide, a nucleophile, an electrophile, an electron donor, an electron acceptor, an olefin, an alkyne, an acidic group, a basic group, an oxidizing group, a reducing group, an electron transfer agent, or a photochemically-reactive species. Non-limiting examples of acid anhydrides include maleic anhydride and succinic anhydride, either of which being substituted or unsubstituted.

A polymer of the disclosure can aggregate with a suitable hydrophobic compound, thereby forming a complex in water held together by favorable hydrophobic interactions. Non-limiting examples of hydrophobic groups that can interact with a polymer of the disclosure include polystyrenes, polyaryls, polyolefins, peptides, hydrocarbons, and halogenated hydrocarbons, such as fluorocarbons. A hydrophobic group can be connected to another group. The aggregation of the polymer and the hydrophobic compound thus attaches the connected other group to the polymer dot. The other group can be a hydrophilic group, for example, polyethylene glycol, a carboxylic acid or a salt thereof. Non-limiting examples of compounds have a hydrophobic part that aggregates with a polymer dot, connected to a hydrophilic group include polystyrene polyethylene glycol carboxylic acid, or a salt thereof (PSPEGCOOH), polystyrene maelic anhydride (PSMA), and polystyrene polyethylene glycol (PSPEG).

A polymer of the disclosure can have a range of subunits, such as monomers or repeat units. The number of subunits in a polymer can be, for example, about 2 to about 100,000, about 2 to about 10,000, about 2 to about 1,000, about 2 to about 100, about 10 to about 100,000, about 10 to about 10,000, about 10 to about 1,000, about 100 to about 100,000, or about 100 to about 10,000. The number of subunits in a polymer can be, for example, greater than 2, greater than 10, greater than 100, greater than 1,000, greater than 10,000; or greater than 100,000.

A polymer of the disclosure can have different kinds of subunits, for example, 2, 3, 4, 5, 6, 7, 8, 9, or 10 different kinds of subunits. An individual subunit can provide as percentage of the overall mass or a percentage of the number of units or monomers of the polymer, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some cases, the conjugated polymers in this disclosure include benzene or a benzene derivative as a repeating unit in the polymer backbone. Fluorine substitution in the benzene repeating unit can tune the Pdot properties such as the conjugation length, absorption, fluorescence, as well as nonspecific labeling of the resulting Pdots. The benzene unit can have variable number of fluorine atoms. In some cases, each benzene unit includes 1 fluorine atom. In some cases, each benzene unit includes 2 fluorine atoms. In some cases, each benzene repeating unit can includes more than 2 fluorine atoms. However, the overall fluorine content in the polymer may be less than 50% of the polymer by mass.

In some cases, the conjugated polymers in this disclosure include fluorene or a fluorene derivative as a repeating unit in the polymer backbone. Fluorine substitution in the fluorene repeating unit can tune the Pdot properties such as the conjugation length, absorption, fluorescence, as well as nonspecific labeling of the resulting Pdots. The fluorene unit can have variable number of fluorine atoms. In some cases, each fluorene unit includes 1 fluorine atom. In some cases, each fluorene unit includes 2 fluorine atoms. In some cases, each fluorene unit can includes more than 2 fluorine atoms. However, the overall fluorine content in the polymer may be less than 50% of the polymer by mass.

In some cases, the conjugated polymers in this disclosure include benzoxadiazole or a benzoxadiazole derivative as a repeating unit in the polymer backbone. Fluorine substitution in the benzoxadiazole repeating unit can tune the Pdot properties such as the conjugation length, absorption, fluorescence, as well as nonspecific labeling of the resulting Pdots. The benzoxadiazole unit can have variable number of fluorine atoms. In some cases, each benzoxadiazole unit includes 1 fluorine atom. In some cases, each benzoxadiazole unit includes 2 fluorine atoms. In some cases, each backbone repeating unit includes 3 fluorine atoms. In some cases, each backbone repeating unit includes 4 fluorine atoms. In some cases, each backbone repeating unit includes 5 fluorine atoms. In some cases, each backbone repeating unit includes 6 fluorine atoms. In some cases, each backbone repeating unit includes 7 fluorine atoms. In some cases, each backbone repeating unit includes 13 fluorine atoms. In some cases, each backbone repeating unit includes more than 5 fluorine atoms. However, the overall fluorine content in the polymer may be less than 50% of the polymer by mass.

In some cases, the conjugated polymers in this disclosure include benzothiadiazole or a benzothiadiazole derivative as a repeating unit in the polymer backbone. Fluorine substitution in the benzothiadiazole repeating unit can tune the Pdot properties such as the conjugation length, absorption, fluorescence, as well as nonspecific labeling of the resulting Pdots. The benzothiadiazole unit can have variable number of fluorine atoms. In some cases, each benzothiadiazole unit includes 1 fluorine atom. In some cases, each benzothiadiazole unit includes 2 fluorine atoms. In some cases, each backbone repeating unit includes 3 fluorine atoms. In some cases, each backbone repeating unit includes 4 fluorine atoms. In some cases, each backbone repeating unit includes 5 fluorine atoms. In some cases, each backbone repeating unit includes 6 fluorine atoms. In some cases, each backbone repeating unit includes 7 fluorine atoms. In some cases, each backbone repeating unit includes 8 fluorine atoms. In some cases, each backbone repeating unit includes 9 fluorine atoms. In some cases, each backbone repeating unit includes 10 fluorine atoms. In some cases, each backbone repeating unit includes 11 fluorine atoms. In some cases, each backbone repeating unit includes 12 fluorine atoms. In some cases, each backbone repeating unit includes 13 fluorine atoms. In some cases, each backbone repeating unit includes more than 5 fluorine atoms. However, the overall fluorine content in the polymer may be less than 50% of the polymer by mass.

In some cases, the conjugated polymers in this disclosure include benzoselenadiazole or a benzoselenadiazole derivative as a repeating unit in the polymer backbone. Fluorine substitution in the benzoselenadiazole repeating unit can tune the Pdot properties such as the conjugation length, absorption, fluorescence, as well as nonspecific labeling of the resulting Pdots. The benzoselenadiazole unit can have variable number of fluorine atoms. In some cases, each benzoselenadiazole unit includes 1 fluorine atom. In some cases, each benzoselenadiazole unit includes 2 fluorine atoms. In some cases, each backbone repeating unit includes 3 fluorine atoms. In some cases, each backbone repeating unit includes 4 fluorine atoms. In some cases, each backbone repeating unit includes 5 fluorine atoms. In some cases, each backbone repeating unit includes more than 5 fluorine atoms. However, the overall fluorine content in the polymer may be less than 50% of the polymer by mass.

In some cases, the conjugated polymers in this disclosure include benzotelluradiazole or a benzotelluradiazole derivative as a repeating unit in the polymer backbone. Fluorine substitution in the benzotelluradiazole repeating unit can tune the Pdot properties such as the conjugation length, absorption, fluorescence, as well as nonspecific labeling of the resulting Pdots. The benzotelluradiazole unit can have variable number of fluorine atoms. In some cases, each benzotelluradiazole unit includes 1 fluorine atom. In some cases, each benzotelluradiazole unit includes 2 fluorine atoms. In some cases, each backbone repeating unit includes 3 fluorine atoms. In some cases, each backbone repeating unit includes 4 fluorine atoms. In some cases, each backbone repeating unit includes 5 fluorine atoms. In some cases, each backbone repeating unit includes more than 5 fluorine atoms. However, the overall fluorine content in the polymer may be less than 50% of the polymer by mass.

In some cases, the conjugated polymers in this disclosure include oxadiazolopyridine or a oxadiazolopyridine derivative as a repeating unit in the polymer backbone. Fluorine substitution in the oxadiazolopyridine repeating unit can tune the Pdot properties such as the conjugation length, absorption, fluorescence, as well as nonspecific labeling of the resulting Pdots. The oxadiazolopyridine unit can have variable number of fluorine atoms. In some cases, each oxadiazolopyridine unit includes 1 fluorine atom. In some cases, each oxadiazolopyridine unit includes 2 fluorine atoms. In some cases, each backbone repeating unit includes 3 fluorine atoms. In some cases, each backbone repeating unit includes 4 fluorine atoms. In some cases, each backbone repeating unit includes 5 fluorine atoms. In some cases, the backbone repeating unit includes 6 fluorine atoms. In some cases, each backbone repeating unit includes more than 6 fluorine atoms. However, the overall fluorine content in the polymer may be less than 50% of the polymer by mass.

In some cases, the conjugated polymers in this disclosure include thiadiazolopyridine or a thiadiazolopyridine derivative as a repeating unit in the polymer backbone. Fluorine substitution in the thiadiazolopyridine repeating unit can tune the Pdot properties such as the conjugation length, absorption, fluorescence, as well as nonspecific labeling of the resulting Pdots. The thiadiazolopyridine unit can have variable number of fluorine atoms. In some cases, each thiadiazolopyridine unit includes 1 fluorine atom. In some cases, each thiadiazolopyridine unit includes 2 fluorine atoms. In some cases, each backbone repeating unit includes 3 fluorine atoms. In some cases, each backbone repeating unit includes 4 fluorine atoms. In some cases, each backbone repeating unit includes 5 fluorine atoms. In some cases, the backbone repeating unit includes 6 fluorine atoms. In some cases, each backbone repeating unit includes more than 6 fluorine atoms. However, the overall fluorine content in the polymer may be less than 50% of the polymer by mass.

In some cases, the conjugated polymers in this disclosure include selenadiazolopyridine or a selenadiazolopyridine derivative as a repeating unit in the polymer backbone. Fluorine substitution in the selenadiazolopyridine repeating unit can tune the Pdot properties such as the conjugation length, absorption, fluorescence, as well as nonspecific labeling of the resulting Pdots. The selenadiazolopyridine unit can have variable number of fluorine atoms. In some cases, each selenadiazolopyridine unit includes 1 fluorine atom. In some cases, each selenadiazolopyridine unit includes 2 fluorine atoms. In some cases, each backbone repeating unit includes 3 fluorine atoms. In some cases, each backbone repeating unit includes 4 fluorine atoms. In some cases, each backbone repeating unit includes 5 fluorine atoms. In some cases, the backbone repeating unit includes 6 fluorine atoms. In some cases, each backbone repeating unit includes more than 6 fluorine atoms. However, the overall fluorine content in the polymer may be less than 50% of the polymer by mass.

In some cases, the conjugated polymers in this disclosure include naphthobisoxadiazole or a naphthobisoxadiazole derivative as a repeating unit in the polymer backbone. Fluorine substitution in the naphthobisoxadiazole repeating unit can tune the Pdot properties such as the conjugation length, absorption, fluorescence, as well as nonspecific labeling of the resulting Pdots. The naphthobisoxadiazole unit can have variable number of fluorine atoms. In some cases, each naphthobisoxadiazole unit includes 1 fluorine atom. In some cases, each naphthobisoxadiazole unit includes 2 fluorine atoms. In some cases, each backbone repeating unit includes 3 fluorine atoms. In some cases, each backbone repeating unit includes 4 fluorine atoms. In some cases, each backbone repeating unit includes 5 fluorine atoms. In some cases, the backbone repeating unit includes 6 fluorine atoms. In some cases, each backbone repeating unit includes more than 6 fluorine atoms. However, the overall fluorine content in the polymer may be less than 50% of the polymer by mass.

In some cases, the conjugated polymers in this disclosure include naphthobisthiadiazole or a naphthobisthiadiazole derivative as a repeating unit in the polymer backbone. Fluorine substitution in the naphthobisthiadiazole repeating unit can tune the Pdot properties such as the conjugation length, absorption, fluorescence, as well as nonspecific labeling of the resulting Pdots. The naphthobisthiadiazole unit can have variable number of fluorine atoms. In some cases, each naphthobisthiadiazole unit includes 1 fluorine atom. In some cases, each naphthobisthiadiazole unit includes 2 fluorine atoms. In some cases, each backbone repeating unit includes 3 fluorine atoms. In some cases, each backbone repeating unit includes 4 fluorine atoms. In some cases, each backbone repeating unit includes 5 fluorine atoms. In some cases, the backbone repeating unit includes 6 fluorine atoms. In some cases, each backbone repeating unit includes more than 6 fluorine atoms. However, the overall fluorine content in the polymer may be less than 50% of the polymer by mass.

In some cases, the conjugated polymers in this disclosure include furan or a furan derivative as a repeating unit in the polymer backbone. Fluorine substitution in the furan repeating unit can tune the Pdot properties such as the conjugation length, absorption, fluorescence, as well as nonspecific labeling of the resulting Pdots. The furan unit can have variable number of fluorine atoms. In some cases, each furan unit includes 1 fluorine atom. In some cases, each furan unit includes 2 fluorine atoms. In some cases, each furan unit can includes more than 2 fluorine atoms. However, the overall fluorine content in the polymer may be less than 50% of the polymer by mass.

In some cases, the conjugated polymers in this disclosure include thiophene or a thiophene derivative as a repeating unit in the polymer backbone. Fluorine substitution in the thiophene repeating unit can tune the Pdot properties such as the conjugation length, absorption, fluorescence, as well as nonspecific labeling of the resulting Pdots. The thiophene unit can have variable number of fluorine atoms. In some cases, each thiophene unit includes 1 fluorine atom. In some cases, each thiophene unit includes 2 fluorine atoms. In some cases, each thiophene unit can includes more than 2 fluorine atoms. In some cases, each backbone repeating unit includes 3 fluorine atoms. In some cases, each backbone repeating unit includes 4 fluorine atoms. In some cases, each backbone repeating unit includes 5 fluorine atoms. In some cases, the backbone repeating unit includes 6 fluorine atoms. In some cases, each backbone repeating unit includes more than 6 fluorine atoms. However, the overall fluorine content in the polymer may be less than 50% of the polymer by mass.

In some cases, the conjugated polymers in this disclosure include thienothiphene or a thienothiphene derivative as a repeating unit in the polymer backbone. Fluorine substitution in the thienothiphene repeating unit can tune the Pdot properties such as the conjugation length, absorption, fluorescence, as well as nonspecific labeling of the resulting Pdots. The thienothiphene unit can have variable number of fluorine atoms. In some cases, each thienothiphene unit includes 1 fluorine atom. In some cases, each thienothiphene unit includes 2 fluorine atoms. In some cases, each thienothiphene unit can includes more than 2 fluorine atoms. In some cases, each backbone repeating unit includes 3 fluorine atoms. In some cases, each backbone repeating unit includes 4 fluorine atoms. In some cases, each backbone repeating unit includes 5 fluorine atoms. In some cases, the backbone repeating unit includes 6 fluorine atoms. In some cases, each backbone repeating unit includes more than 6 fluorine atoms. However, the overall fluorine content in the polymer may be less than 50% of the polymer by mass.

In some cases, the conjugated polymers in this disclosure include cyclopentadithiophene or a cyclopentadithiophene derivative as a repeating unit in the polymer backbone. Fluorine substitution in the cyclopentadithiophene repeating unit can tune the Pdot properties such as the conjugation length, absorption, fluorescence, as well as nonspecific labeling of the resulting Pdots. The cyclopentadithiophene unit can have variable number of fluorine atoms. In some cases, each cyclopentadithiophene unit includes 1 fluorine atom. In some cases, each cyclopentadithiophene unit includes 2 fluorine atoms. In some cases, each cyclopentadithiophene unit can includes more than 2 fluorine atoms. In some cases, each backbone repeating unit includes 3 fluorine atoms. In some cases, each backbone repeating unit includes 4 fluorine atoms. In some cases, each backbone repeating unit includes 5 fluorine atoms. In some cases, the backbone repeating unit includes 6 fluorine atoms. In some cases, each backbone repeating unit includes more than 6 fluorine atoms. However, the overall fluorine content in the polymer may be less than 50% of the polymer by mass.

In some cases, the conjugated polymers in this disclosure include silolodithiophene or a silolodithiophene derivative as a repeating unit in the polymer backbone. Fluorine substitution in the silolodithiophene repeating unit can tune the Pdot properties such as the conjugation length, absorption, fluorescence, as well as nonspecific labeling of the resulting Pdots. The silolodithiophene unit can have variable number of fluorine atoms. In some cases, each silolodithiophene unit includes 1 fluorine atom. In some cases, each silolodithiophene unit includes 2 fluorine atoms. In some cases, each backbone repeating unit includes 3 fluorine atoms. In some cases, each backbone repeating unit includes 4 fluorine atoms. In some cases, each backbone repeating unit includes 5 fluorine atoms. In some cases, the backbone repeating unit includes 6 fluorine atoms. In some cases, each backbone repeating unit includes more than 6 fluorine atoms. In some cases, each silolodithiophene unit can includes more than 2 fluorine atoms. However, the overall fluorine content in the polymer may be less than 50% of the polymer by mass.

In some cases, the conjugated polymers in this disclosure include dithienopyrrole or a dithienopyrrole derivative as a repeating unit in the polymer backbone. Fluorine substitution in the dithienopyrrole repeating unit can tune the Pdot properties such as the conjugation length, absorption, fluorescence, as well as nonspecific labeling of the resulting Pdots. The dithienopyrrole unit can have variable number of fluorine atoms. In some cases, each dithienopyrrole unit includes 1 fluorine atom. In some cases, each dithienopyrrole unit includes 2 fluorine atoms. In some cases, each dithienopyrrole unit can includes more than 2 fluorine atoms. In some cases, each backbone repeating unit includes 3 fluorine atoms. In some cases, each backbone repeating unit includes 4 fluorine atoms. In some cases, each backbone repeating unit includes 5 fluorine atoms. In some cases, the backbone repeating unit includes 6 fluorine atoms. In some cases, each backbone repeating unit includes more than 6 fluorine atoms. However, the overall fluorine content in the polymer may be less than 50% of the polymer by mass.

In some cases, the conjugated polymers in this disclosure include quinoxaline or a quinoxaline derivative as a repeating unit in the polymer backbone. Fluorine substitution in the quinoxaline repeating unit can tune the Pdot properties such as the conjugation length, absorption, fluorescence, as well as nonspecific labeling of the resulting Pdots. The quinoxaline unit can have variable number of fluorine atoms. In some cases, each quinoxaline unit includes 1 fluorine atom. In some cases, each quinoxaline unit includes 2 fluorine atoms. In some cases, each quinoxaline unit can includes more than 2 fluorine atoms. In some cases, each backbone repeating unit includes 3 fluorine atoms. In some cases, each backbone repeating unit includes 4 fluorine atoms. In some cases, each backbone repeating unit includes 5 fluorine atoms. In some cases, the backbone repeating unit includes 6 fluorine atoms. In some cases, each backbone repeating unit includes more than 6 fluorine atoms. However, the overall fluorine content in the polymer may be less than 50% of the polymer by mass.

In some cases, the conjugated polymers in this disclosure include pyrazinoquinoxaline or a pyrazinoquinoxaline derivative as a repeating unit in the polymer backbone. Fluorine substitution in the pyrazinoquinoxaline repeating unit can tune the Pdot properties such as the conjugation length, absorption, fluorescence, as well as nonspecific labeling of the resulting Pdots. The pyrazinoquinoxaline unit can have variable number of fluorine atoms. In some cases, each pyrazinoquinoxaline unit includes 1 fluorine atom. In some cases, each pyrazinoquinoxaline unit includes 2 fluorine atoms. In some cases, each pyrazinoquinoxaline unit can includes more than 2 fluorine atoms. In some cases, each backbone repeating unit includes 3 fluorine atoms. In some cases, each backbone repeating unit includes 4 fluorine atoms. In some cases, each backbone repeating unit includes 5 fluorine atoms. In some cases, the backbone repeating unit includes 6 fluorine atoms. In some cases, each backbone repeating unit includes more than 6 fluorine atoms. However, the overall fluorine content in the polymer may be less than 50% of the polymer by mass.

In some cases, the conjugated polymers in this disclosure include benzo[c]thiophene or a benzo[c]thiophene derivative as a repeating unit in the polymer backbone. Fluorine substitution in the benzo[c]thiophene repeating unit can tune the Pdot properties such as the conjugation length, absorption, fluorescence, as well as nonspecific labeling of the resulting Pdots. The benzo[c]thiophene unit can have variable number of fluorine atoms. In some cases, each benzo[c]thiophene unit includes 1 fluorine atom. In some cases, each benzo[c]thiophene unit includes 2 fluorine atoms. In some cases, each benzo[c]thiophene unit can includes more than 2 fluorine atoms. In some cases, each backbone repeating unit includes 3 fluorine atoms. In some cases, each backbone repeating unit includes 4 fluorine atoms. In some cases, each backbone repeating unit includes 5 fluorine atoms. In some cases, the backbone repeating unit includes 6 fluorine atoms. In some cases, each backbone repeating unit includes more than 6 fluorine atoms. However, the overall fluorine content in the polymer may be less than 50% of the polymer by mass.

In some cases, the conjugated polymers in this disclosure include isobenzofuran or a isobenzofuran derivative as a repeating unit in the polymer backbone. Fluorine substitution in the isobenzofuran repeating unit can tune the Pdot properties such as the conjugation length, absorption, fluorescence, as well as nonspecific labeling of the resulting Pdots. The isobenzofuran unit can have variable number of fluorine atoms. In some cases, each isobenzofuran unit includes 1 fluorine atom. In some cases, each isobenzofuran unit includes 2 fluorine atoms. In some cases, each isobenzofuran unit can includes more than 2 fluorine atoms. In some cases, each backbone repeating unit includes 3 fluorine atoms. In some cases, each backbone repeating unit includes 4 fluorine atoms. In some cases, each backbone repeating unit includes 5 fluorine atoms. In some cases, the backbone repeating unit includes 6 fluorine atoms. In some cases, each backbone repeating unit includes more than 6 fluorine atoms. However, the overall fluorine content in the polymer may be less than 50% of the polymer by mass.

In some cases, the conjugated polymers in this disclosure include benzo[c]selenophene or a benzo[c]selenophene derivative as a repeating unit in the polymer backbone. Fluorine substitution in the benzo[c]selenophene repeating unit can tune the Pdot properties such as the conjugation length, absorption, fluorescence, as well as nonspecific labeling of the resulting Pdots. The benzo[c]selenophene unit can have variable number of fluorine atoms. In some cases, each benzo[c]selenophene unit includes 1 fluorine atom. In some cases, each benzo[c]selenophene unit includes 2 fluorine atoms. In some cases, each benzo[c]selenophene unit can includes more than 2 fluorine atoms. In some cases, each backbone repeating unit includes 3 fluorine atoms. In some cases, each backbone repeating unit includes 4 fluorine atoms. In some cases, each backbone repeating unit includes 5 fluorine atoms. In some cases, the backbone repeating unit includes 6 fluorine atoms. In some cases, each backbone repeating unit includes more than 6 fluorine atoms. However, the overall fluorine content in the polymer may be less than 50% of the polymer by mass.

In some cases, the conjugated polymers in this disclosure include pyrene or a pyrene derivative as a repeating unit in the polymer backbone. Fluorine substitution in the pyrene repeating unit can tune the Pdot properties such as the conjugation length, absorption, fluorescence, as well as nonspecific labeling of the resulting Pdots. The pyrene unit can have variable number of fluorine atoms. In some cases, each pyrene unit includes 1 fluorine atom. In some cases, each pyrene unit includes 2 fluorine atoms. In some cases, each backbone repeating unit includes 3 fluorine atoms. In some cases, each backbone repeating unit includes 4 fluorine atoms. In some cases, each backbone repeating unit includes 5 fluorine atoms. In some cases, the backbone repeating unit includes 6 fluorine atoms. In some cases, each backbone repeating unit includes more than 6 fluorine atoms. In some cases, each pyrene unit can includes more than 2 fluorine atoms. However, the overall fluorine content in the polymer may be less than 50% of the polymer by mass.

In some cases, the conjugated polymers in this disclosure include naphthelene or a naphthelene derivative as a repeating unit in the polymer backbone. Fluorine substitution in the naphthelene repeating unit can tune the Pdot properties such as the conjugation length, absorption, fluorescence, as well as nonspecific labeling of the resulting Pdots. The naphthelene unit can have variable number of fluorine atoms. In some cases, each naphthelene unit includes 1 fluorine atom. In some cases, each naphthelene unit includes 2 fluorine atoms. In some cases, each naphthelene unit can includes more than 2 fluorine atoms. In some cases, each backbone repeating unit includes 3 fluorine atoms. In some cases, each backbone repeating unit includes 4 fluorine atoms. In some cases, each backbone repeating unit includes 5 fluorine atoms. In some cases, the backbone repeating unit includes 6 fluorine atoms. In some cases, each backbone repeating unit includes more than 6 fluorine atoms. However, the overall fluorine content in the polymer may be less than 50% of the polymer by mass.

In some cases, the conjugated polymers in this disclosure include anthracene or an anthracene derivative as a repeating unit in the polymer backbone. Fluorine substitution in the anthracene repeating unit can tune the Pdot properties such as the conjugation length, absorption, fluorescence, as well as nonspecific labeling of the resulting Pdots. The anthracene unit can have variable number of fluorine atoms. In some cases, each anthracene unit includes 1 fluorine atom. In some cases, each anthracene unit includes 2 fluorine atoms. In some cases, each anthracene unit can includes more than 2 fluorine atoms. In some cases, each backbone repeating unit includes 3 fluorine atoms. In some cases, each backbone repeating unit includes 4 fluorine atoms. In some cases, each backbone repeating unit includes 5 fluorine atoms. In some cases, the backbone repeating unit includes 6 fluorine atoms. In some cases, each backbone repeating unit includes more than 6 fluorine atoms. However, the overall fluorine content in the polymer may be less than 50% of the polymer by mass.

In some cases, the conjugated polymers in this disclosure include vinyl unit or a vinyl derivative as a repeating unit in the polymer backbone. Fluorine substitution in the vinyl repeating unit can tune the Pdot properties such as the conjugation length, absorption, fluorescence, as well as nonspecific labeling of the resulting Pdots. The vinyl unit can have variable number of fluorine atoms. In some cases, each vinyl unit includes 1 fluorine atom. In some cases, each vinyl unit includes 2 fluorine atoms. In some cases, each backbone repeating unit includes 3 fluorine atoms. In some cases, each backbone repeating unit includes 4 fluorine atoms. In some cases, each backbone repeating unit includes 5 fluorine atoms. In some cases, each backbone repeating unit includes more than 5 fluorine atoms. However, the overall fluorine content in the polymer may be less than 50% of the polymer by mass.

In some cases, the conjugated polymers in this disclosure include boron-dipyrromethene (BODIPY) or a BODIPY derivative as a repeating unit in the polymer backbone. Fluorine substitution in the BODIPY repeating unit can tune the Pdot properties such as the conjugation length, absorption, fluorescence, as well as nonspecific labeling of the resulting Pdots. The BODIPY unit can have variable number of fluorine atoms. In some cases, each BODIPY unit includes 1 fluorine atom. In some cases, each BODIPY unit includes 2 fluorine atoms. In some cases, each BODIPY unit can includes more than 2 fluorine atoms. In some cases, each backbone repeating unit includes 3 fluorine atoms. In some cases, each backbone repeating unit includes 4 fluorine atoms. In some cases, each backbone repeating unit includes 5 fluorine atoms. In some cases, each backbone repeating unit includes 6 fluorine atoms. In some cases, each backbone repeating unit includes 7 fluorine atoms. In some cases, each backbone repeating unit includes 8 fluorine atoms. In some cases, each backbone repeating unit includes 9 fluorine atoms. In some cases, each backbone repeating unit includes 10 fluorine atoms. In some cases, each backbone repeating unit includes more than 10 fluorine atoms. However, the overall fluorine content in the polymer may be less than 50% of the polymer by mass.

In some cases, the conjugated polymers in this disclosure include porphyrin or a porphyrin derivative as a repeating unit in the polymer backbone. Fluorine substitution in the porphyrin repeating unit can tune the Pdot properties such as the conjugation length, absorption, fluorescence, as well as nonspecific labeling of the resulting Pdots. The porphyrin unit can have variable number of fluorine atoms. In some cases, each porphyrin unit includes 1 fluorine atom. In some cases, each porphyrin unit includes 2 fluorine atoms. In some cases, each backbone repeating unit includes 3 fluorine atoms. In some cases, each backbone repeating unit includes 4 fluorine atoms. In some cases, each backbone repeating unit includes 5 fluorine atoms. In some cases, the backbone repeating unit includes 6 fluorine atoms. In some cases, the backbone repeating unit includes 7 fluorine atoms. In some cases, the backbone repeating unit includes 8 fluorine atoms. In some cases, the backbone repeating unit includes 9 fluorine atoms. In some cases, the backbone repeating unit includes 10 fluorine atoms. In some cases, the backbone repeating unit includes 11 fluorine atoms. In some cases, the backbone repeating unit includes 12 fluorine atoms. In some cases, the backbone repeating unit includes 13 fluorine atoms. In some cases, each backbone repeating unit includes more than 13 fluorine atoms. However, the overall fluorine content in the polymer may be less than 50% of the polymer by mass.

In some cases, the conjugated polymers in this disclosure include benzophenanthroline or a benzophenanthroline derivative as a repeating unit in the polymer backbone. Fluorine substitution in the benzophenanthroline repeating unit can tune the Pdot properties such as the conjugation length, absorption, fluorescence, as well as nonspecific labeling of the resulting Pdots. The benzophenanthroline unit can have variable number of fluorine atoms. In some cases, each benzophenanthroline unit includes 1 fluorine atom. In some cases, each benzophenanthroline unit includes 2 fluorine atoms. In some cases, each benzophenanthroline unit includes 3 fluorine atoms. In some cases, each benzophenanthroline unit includes 4 fluorine atoms. In some cases, each benzophenanthroline unit can includes more than 4 fluorine atoms. However, the overall fluorine content in the polymer may be less than 50% of the polymer by mass.

In some cases, the conjugated polymers in this disclosure include anthradiisoquinoline or a anthradiisoquinoline derivative as a repeating unit in the polymer backbone. Fluorine substitution in the anthradiisoquinoline repeating unit can tune the Pdot properties such as the conjugation length, absorption, fluorescence, as well as nonspecific labeling of the resulting Pdots. The anthradiisoquinoline unit can have variable number of fluorine atoms. In some cases, each anthradiisoquinoline unit includes 1 fluorine atom. In some cases, each anthradiisoquinoline unit includes 2 fluorine atoms. In some cases, each anthradiisoquinoline unit includes 3 fluorine atoms. In some cases, each anthradiisoquinoline unit includes 4 fluorine atoms. In some cases, each anthradiisoquinoline unit can includes more than 4 fluorine atoms. However, the overall fluorine content in the polymer may be less than 50% of the polymer by mass.

In some cases, the conjugated polymers in this disclosure include squaraine or a squaraine derivative as a repeating unit in the polymer backbone. Fluorine substitution in the squaraine repeating unit can tune the Pdot properties such as the conjugation length, absorption, fluorescence, as well as nonspecific labeling of the resulting Pdots. The squaraine unit can have variable number of fluorine atoms. In some cases, each squaraine unit includes 1 fluorine atom. In some cases, each squaraine unit includes 2 fluorine atoms. In some cases, each squaraine unit includes 3 fluorine atoms. In some cases, each squaraine unit includes 4 fluorine atoms. In some cases, each squaraine unit can includes more than 4 fluorine atoms. However, the overall fluorine content in the polymer may be less than 50% of the polymer by mass.

In some cases, the polymer comprises a repeating subunit having the structure of Formula (I):

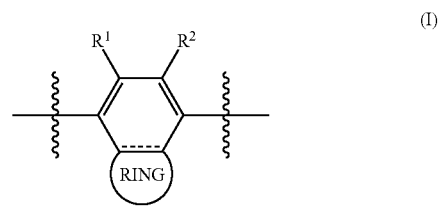

wherein:
    each of $R^1$ and $R^2$ is independently H, F, Cl, Br, or I;
    ------ is a single or double bond; and
    RING is a cyclic group.

In some aspects, each of $R^1$ and $R^2$ is independently H, F, or Cl. Non-limiting examples of cyclic groups include aromatic rings, non-aromatic rings, heterocyclic rings, and non-heterocyclic rings.

In some cases, the polymer comprises a repeating subunit having the structure of Formula (II):

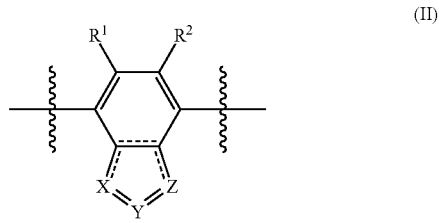

wherein:
    each of $R^1$ and $R^2$ is independently H, F, Cl, Br, or I;
    each of ------ is independently a single or double bond;
    each of X, Y, and Z is independently N, N(W), S, O, CW, or CWW; and
    each W is independently H, F, Cl, OH, SH, an amino group, a nitro group, a nitroso group, a cyano group, an azido group, a sulfoxide group, a sulfone group, a sulfonamide group, a carboxyl group, a carboxaldehyde group, an imine group, an alkyl group, a haloalkyl group, an alkenyl group, a halo-alkenyl group, an alkynyl group, a halo-alkynyl group, an alkoxy group, an aryl group, an aryloxy group, an aralkyl group, an arylalkoxy group, a heterocyclyl group, an acyl group, an acyloxy group, a carbonate group, a carbamate group, an amide group, a urethane group, or an ester group.

In some aspects, each of $R^1$ and $R^2$ is independently H, F, or Cl.

In some cases, the polymer comprises a repeating subunit having the structure of Formula (III):

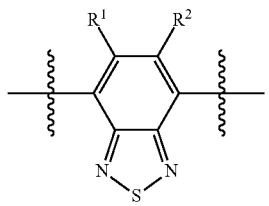

(III)

wherein each of $R^1$ and $R^2$ is independently H, F, Cl, Br, or I. In some cases, at least one of $R^1$ and $R^2$ is F.

In some aspects, each of $R^1$ and $R^2$ is F.

In some aspects, each of $R^1$ and $R^2$ is independently H, F, or Cl.

In some cases, the polymer comprises a repeating subunit having the structure of Formula (IV):

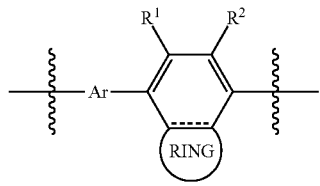

(IV)

wherein:

each of $R^1$ and $R^2$ is independently H, F, Cl, Br, or I;

------ is a single or double bond;

RING is a cyclic group; and

Ar is an aromatic group.

In some aspects, each of $R^1$ and $R^2$ is independently H, F, or Cl.

In some cases, the polymer comprises a repeating subunit having the structure of Formula (V):

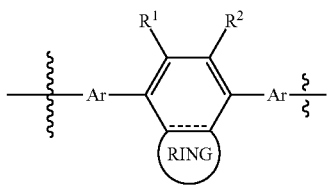

(V)

wherein:

each of $R^1$ and $R^2$ is independently H, F, Cl, Br, or I;

------ is a single or double bond;

RING is a cyclic group; and each Ar is independently an aromatic group.

In some aspects, each of $R^1$ and $R^2$ is independently H, F, or Cl.

In some cases, the polymer comprises a repeating subunit having the structure of Formula (VI):

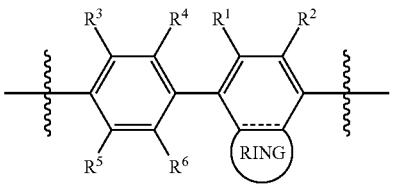

(VI)

wherein:

each of $R^1$, $R^2$, $R^3$, $R^4$, $R^5$, and $R^6$ is independently H, F, Cl, Br, or I;

------ is a single or double bond; and

RING is a cyclic group.

In some cases, the polymer comprises a repeating subunit having the structure of Formula (VII):

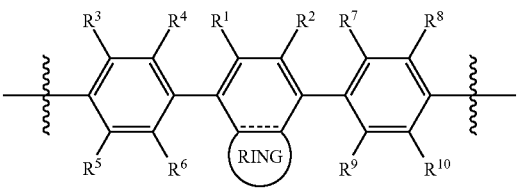

(VII)

wherein:

each of $R^1$, $R^2$, $R^3$, $R^4$, $R^5$, $R^6$, $R^7$, $R^8$, $R^9$, and $R^{10}$ is independently H, F, Cl, Br, or I;

------ is a single or double bond; and

RING is a cyclic group.

In some aspects, $R^1$, $R^2$, $R^3$, $R^4$, $R^5$, $R^6$, $R^7$, $R^8$, $R^9$, and $R^{10}$ is independently H, F, or Cl.

In some cases, the polymer comprises a repeating subunit having the structure of Formula (VIII):

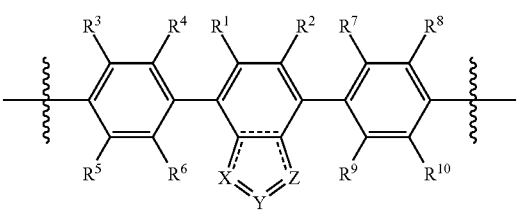

(VIII)

wherein:

each of $R^1$, $R^2$, $R^3$, $R^4$, $R^5$, $R^6$, $R^7$, $R^8$, $R^9$, and $R^{10}$ is independently H, F, Cl, Br, or I;

each ------ is independently a single or double bond;

each of X, Y, and Z is independently N, NW, S, O, CW, or CWW; and each W is independently H, F, Cl, OH, SH, an amino group, a nitro group, a nitroso group, a cyano group, an azido group, a sulfoxide group, a sulfone group, a sulfonamide group, a carboxyl group, a carboxaldehyde group, an imine group, an alkyl group, a halo-alkyl group, an alkenyl group, a halo-alkenyl group, an alkynyl group, a halo-alkynyl group, an alkoxy group, an aryl group, an aryloxy group, an aralkyl group, an arylalkoxy group, a heterocyclyl group, an acyl group, an acyloxy group, a carbonate group, a carbamate group, an amide group, a urethane group, or an ester group.

In some aspects, $R^1$, $R^2$, $R^3$, $R^4$, $R^5$, $R^6$, $R^7$, $R^8$, $R^9$, and $R^{10}$ is independently H, F, or Cl.

In some cases, the polymer comprises a repeating subunit having the structure of Formula (IX):

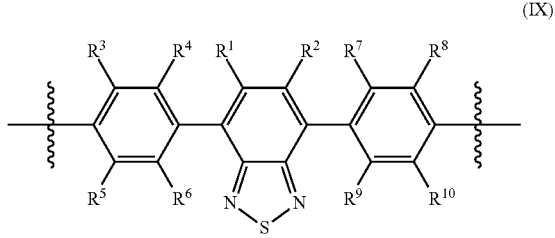

(IX)

wherein each of $R^1$, $R^2$, $R^3$, $R^4$, $R^5$, $R^6$, $R^7$, $R^8$, $R^9$, and $R^{10}$ is independently H, F, Cl, Br, or I.

In some aspects, $R^1$, $R^2$, $R^3$, $R^4$, $R^5$, $R^6$, $R^7$, $R^8$, $R^9$, and $R^{10}$ is independently H, F, or Cl.

In some cases, the polymer comprises a repeating subunit having the structure of Formula (X):

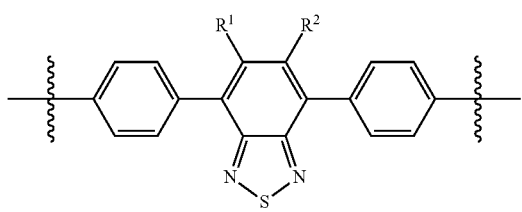

(X)

wherein at least one of $R^1$ and $R^2$ is F. In some cases, each of $R^1$ and $R^2$ is F.

In some cases, the polymer comprises a repeating subunit having the structure of Formula (XI):

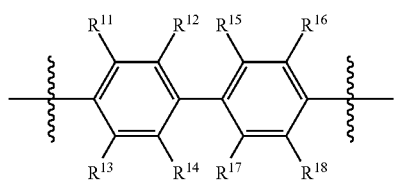

(XI)

wherein:
each of $R^{11}$, $R^{13}$, $R^{16}$, and $R^{18}$ is independently H, F, Cl, Br, or I;
each of $R^{12}$ and $R^{15}$ is independently H, F, Cl, Br, I, or $R^{12}$ and $R^{15}$ together with the atoms to which they are bound form a ring; and
each of $R^{14}$ and $R^{17}$ is independently H, F, Cl, Br, I, or $R^{14}$ and $R^{17}$ together with the atoms to which they are bound form a ring.

In some aspects, $R^{11}$, $R^{13}$, $R^{16}$, and $R^{18}$ is independently H, F, or Cl.

In some cases, the polymer comprises a repeating subunit having the structure of Formula (XII):

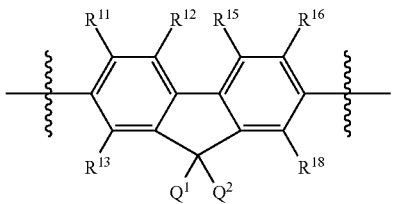

(XII)

wherein:
each of $R^{11}$, $R^{12}$, $R^{13}$, $R^{14}$, $R^{15}$, $R^{16}$, and $R^{18}$ is independently H, F, Cl, Br, or I; and
each of $Q^1$ and $Q^2$ is independently H, F, Cl, OH, SH, an amino group, a nitro group, a nitroso group, a cyano group, an azido group, an alkyl group, a halo-alkyl group, an alkenyl group, a halo-alkenyl group, an alkynyl group, a halo-alkynyl group, an alkoxy group, an aryl group, an aryloxy group, an aralkyl group, an arylalkoxy group, a heterocyclyl group, an acyl group, an acyloxy group, a carbonate group, a carbamate group, an amide group, a urethane group, or an ester group. In some cases, each of $Q^1$ and $Q^2$ is independently an alkyl group, an alkenyl group, an alkynyl group, an aryl group, an aralkyl group, or a heterocyclyl group. In some cases, each of $Q^1$ and $Q^2$ is independently an alkyl group. $Q^1$ and $Q^2$ can be the same or different.

In some aspects, $R^{11}$, $R^{12}$, $R^{13}$, $R^{14}$, $R^{15}$, $R^{16}$, and $R^{18}$ is independently H, F, or Cl.

In some cases, the polymer comprises a repeating subunit having the structure of Formula (XIII):

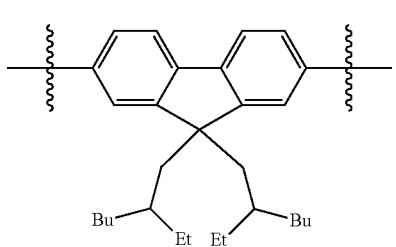

(XIII)

In some cases, the polymer comprises a repeating subunit having the structure of Formula (XIV):

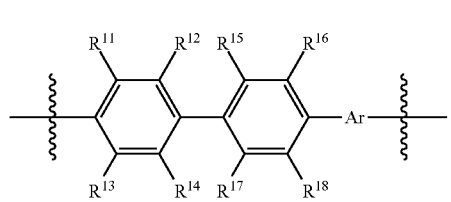

(XIV)

wherein:
each of $R^{11}$, $R^{13}$, $R^{16}$, and $R^{18}$ is independently H, F, Cl, Br, or I;
each of $R^{12}$ and $R^{15}$ is independently H, F, Cl, Br, I, or $R^{12}$ and $R^{15}$ together with the atoms to which they are bound form a ring; and
each of $R^{14}$ and $R^{17}$ is independently H, F, Cl, Br, I, or $R^{14}$ and $R^{17}$ together with the atoms to which they are bound form a ring; and Ar is an aromatic group.

In some aspects, $R^{11}$, $R^{12}$, $R^{13}$, $R^{14}$, $R^{15}$, $R^{16}$, $R^{17}$, and $R^{18}$ is independently H, F, or Cl.

In some cases, the polymer comprises a repeating subunit having the structure of Formula (XVA):

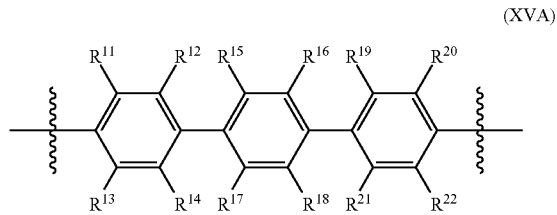

(XVA)

wherein:

each of $R^{11}$, $R^{13}$, $R^{16}$, $R^{18}$, $R^{19}$, $R^{20}$, $R^{21}$, and $R^{22}$ is independently H, F, Cl, Br, or I;

each of $R^{12}$ and $R^{15}$ is independently H, F, Cl, Br, I, or $R^{12}$ and $R^{15}$ together with the atoms to which they are bound form a ring; and each of $R^{14}$ and $R^{17}$ is independently H, F, Cl, Br, I, or $R^{14}$ and $R^{17}$ together with the atoms to which they are bound form a ring.

In some aspects, $R^{11}$, $R^{12}$, $R^{13}$, $R^{14}$, $R^{15}$, $R^{16}$, $R^{17}$, and $R^{18}$ is independently H, F, or Cl.

In some cases, the polymer comprises a repeating subunit having the structure of Formula (XVI):

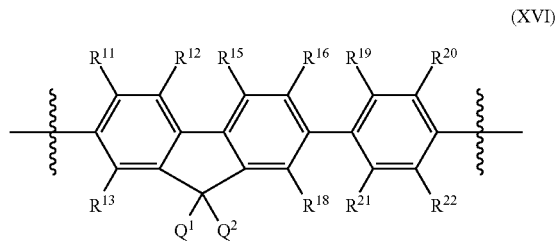

(XVI)

wherein:

each of $R^{11}$, $R^{12}$, $R^{13}$, $R^{15}$, $R^{16}$, $R^{18}$, $R^{19}$, $R^{20}$, $R^{21}$, and $R^{22}$ is independently H, F, or Cl; and each of $Q^1$ and $Q^2$ is independently H, F, Cl, OH, SH, an amino group, a nitro group, a nitroso group, a cyano group, an azido group, an alkyl group, a halo-alkyl group, an alkenyl group, a halo-alkenyl group, an alkynyl group, a halo-alkynyl group, an alkoxy group, an aryl group, an aryloxy group, an aralkyl group, an arylalkoxy group, a heterocyclyl group, an acyl group, an acyloxy group, a carbonate group, a carbamate group, an amide group, a urethane group, or an ester group.

In some aspects, $R^{11}$, $R^{12}$, $R^{13}$, $R^{14}$, $R^{15}$, $R^{16}$, $R^{17}$, and $R^{18}$ is independently H, F, or Cl.

In some cases, each of $Q^1$ and $Q^2$ is independently an alkyl group, an alkenyl group, an alkynyl group, an aryl group, an aralkyl group, or a heterocyclyl group. In some cases, each of $Q^1$ and $Q^2$ is independently an alkyl group. $Q^1$ and $Q^2$ can be the same or different.

In some cases, the polymer comprises a repeating subunit having the structure of Formula (XVIIA):

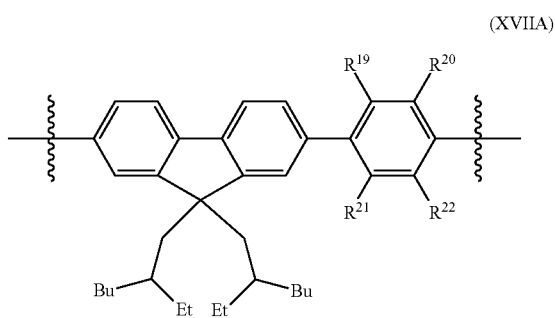

(XVIIA)

wherein:

each of $R^{19}$, $R^{20}$, $R^{21}$, and $R^{22}$ is independently H, F, Cl, Br, or I.

In some aspects, $R^{19}$, $R^{20}$, and $R^{22}$ is independently H, F, or Cl.

In some cases, at least one of $R^{19}$, $R^{20}$, and $R^{22}$ is F. In some cases, one, two, three, or four of $R^{19}$, $R^{20}$, $R^{21}$, and $R^{22}$ is F. In some cases, $R^{19}$ is H; $R^{20}$ is F; $R^{21}$ is F; and $R^{22}$ is H.

In some cases, the polymer comprises a repeating subunit having the structure of Formula (XVIII):

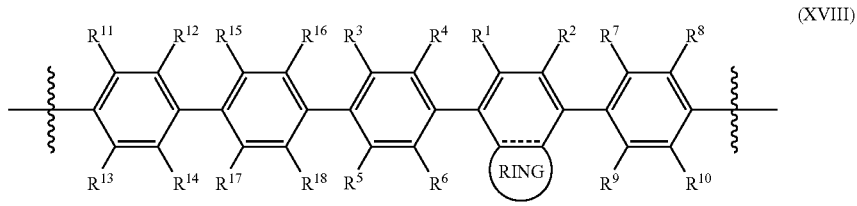

(XVIII)

wherein:

each of $R^1$, $R^2$, $R^3$, $R^4$, $R^5$, $R^6$, $R^7$, $R^8$, $R^9$, $R^{10}$, $R^{11}$, $R^{13}$, $R^{16}$, and $R^{18}$ independently H, F, Cl, Br, or I;

each of $R^{12}$ and $R^{15}$ is independently H, F, Cl, Br, or I, or $R^{12}$ and $R^{15}$ together with the atoms to which they are bound form a ring;

each of $R^{14}$ and $R^{17}$ is independently H, F, Cl, Br, or I, or $R^{14}$ and $R^{17}$ together with the atoms to which they are bound form a ring;

----- is a single or double bond; and

RING is a cyclic group.

In some aspects, each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently H, F, or Cl.

In some cases, at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is F.

In some cases, the polymer comprises a repeating subunit having the structure of Formula (XIV):

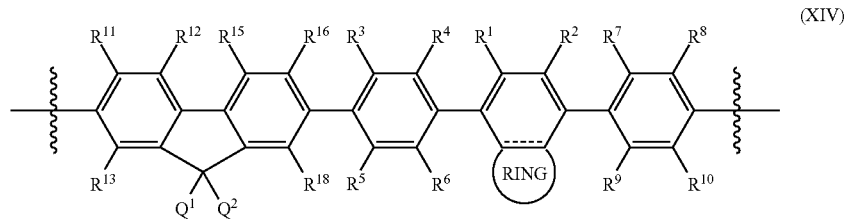

(XIV)

wherein:
each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{15}$, $R^{16}$, and $R^{18}$ is independently H, F, Cl, Br, or I;
------ is a single or double bond; and
RING is a cyclic group.

In some cases, at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{15}$, $R^{16}$, and $R^{18}$ is F.

In some cases, the polymer comprises a repeating subunit having the structure of Formula (XVB):

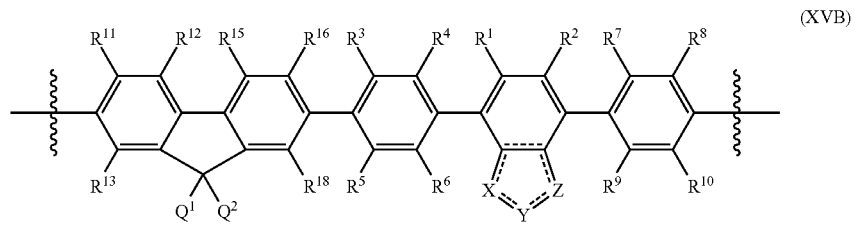

(XVB)

wherein:
each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{15}$, $R^{16}$, and $R^{18}$ is independently H, F, Cl, Br, or I;
each ------ is independently a single or double bond;
each of X, Y, and Z is independently N, NW, S, O, CW, or CWW;
each of $Q^1$ and $Q^2$ is independently H, F, Cl, Br, I, OH, SH, an amino group, a nitro group, a nitroso group, a cyano group, an azido group, an alkyl group, a halo-alkyl group, an alkenyl group, a halo-alkenyl group, an alkynyl group, a halo-alkynyl group, an alkoxy group, an aryl group, an aryloxy group, an aralkyl group, an arylalkoxy group, a heterocyclyl group, an acyl group, an acyloxy group, a carbonate group, a carbamate group, an amide group, a urethane group, or an ester group; and each W is independently H, F, Cl, Br, I, OH, SH, an amino group, a nitro group, a nitroso group, a cyano group, an azido group, a sulfoxide group, a sulfone group, a sulfonamide group, a carboxyl group, a carboxaldehyde group, an imine group, an alkyl group, a halo-alkyl group, an alkenyl group, a halo-alkenyl group, an alkynyl group, a halo-alkynyl group, an alkoxy group, an aryl group, an aryloxy group, an aralkyl group, an arylalkoxy group, a heterocyclyl group, an acyl group, an acyloxy group, a carbonate group, a carbamate group, an amide group, a urethane group, or an ester group.

In some aspects, each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently H, F, or Cl.

In some cases, at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{15}$, $R^{16}$, and $R^{18}$ is F. In some cases, each of $Q^1$ and $Q^2$ is independently an alkyl group, an alkenyl group, an alkynyl group, an aryl group, an aralkyl group, or a heterocyclyl group. In some cases, each of $Q^1$ and $Q^2$ is independently an alkyl group. $Q^1$ and $Q^2$ can be the same or different.

In some cases, the polymer comprises a repeating subunit having the structure of Formula (XVIB):

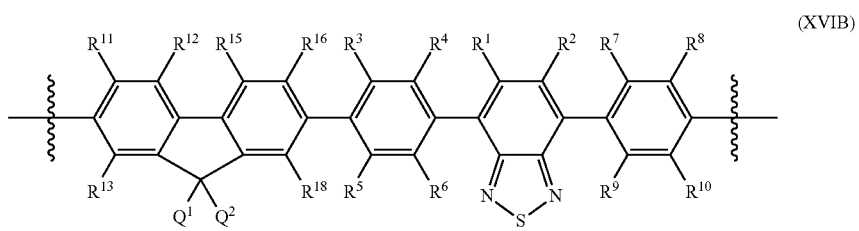

(XVIB)

wherein:
each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{15}$, $R^{16}$, $R^{18}$ is independently H, F, Cl, Br, or I; and each of $Q^1$ and $Q^2$ is independently H, F, Cl, Br, I, OH, SH, an amino group, a nitro group, a nitroso group, a cyano group, an azido group, an alkyl group, a halo-alkyl group, an alkenyl group, a halo-alkenyl group, an alkynyl group, a halo-alkynyl group, an alkoxy group, an aryl group, an aryloxy group, an aralkyl group, an arylalkoxy group, a heterocyclyl group, an acyl group, an acyloxy group, a carbonate group, a carbamate group, an amide group, a urethane group, or an ester group.

In some aspects, each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently H, F, or Cl.

In some cases, at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{15}$, $R^{16}$, and $R^{18}$ is F. In some cases, each of $Q^1$ and $Q^2$ is independently an alkyl group, an alkenyl group, an alkynyl group, an aryl group, an aralkyl group, or a heterocyclyl group. In some cases, each of $Q^1$ and $Q^2$ is independently an alkyl group. $Q^1$ and $Q^2$ can be the same or different.

In some cases, the polymer comprises a repeating subunit having the structure of Formula (XVIIB):

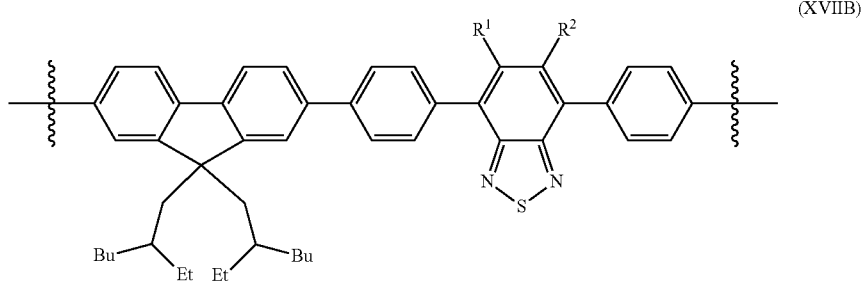

(XVIIB)

wherein:

each of $R^1$ and $R^2$ is independently H, F, Cl, Br, or I.

In some aspects, each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently H, F, or Cl.

In some cases, at least one of $R^1$ and $R^2$ is F. In some cases, each of $R^1$ and $R^2$ is F.

Non-limiting examples of rings formed by $R^{12}$ and $R^{15}$ groups, or $R^{14}$ and $R^{17}$ groups include 5, 6, 7, 8, 9, 10, 11, and 12-membered rings, aromatic rings, non-aromatic rings, heterocycles, and carbocycles. Rings can contain a bridging heteroatom, such as oxygen, nitrogen, or sulfur. The ring can be substituted, for example, by any substituent described herein.

In some cases, a Q group of any formula herein can be a moiety having the structure of Formula (XVIII) or (XIX):

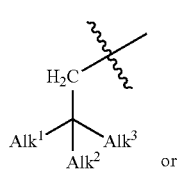

(XVIII)

or

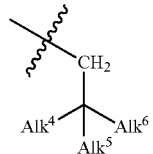

(XIX)

wherein each of $Alk^1$, $Alk^2$, $Alk^3$, $Alk^4$, $Alk^5$, and $Alk^6$ is independently H or any alkyl, alkenyl, or alkynyl group described herein In some cases, $Alk^2$ and $Alk^5$ are H, and $Alk^1$, $Alk^3$, $Alk^4$, and $Alk^6$ are independently alkyl groups. In some cases, $Alk^2$ and $Alk^5$ are H, $Alk^1$ and $Alk^6$ are butyl groups, and $Alk^3$ and $Alk^4$ are ethyl groups.

The groups described herein are substituted or unsubstituted. Substituents for the alkyl and heteroalkyl radicals (including those groups in various aspects referred to as alkylene, alkenyl, heteroalkylene, heteroalkenyl, alkynyl, cycloalkyl, heterocycloalkyl, cycloalkenyl, and heterocycloalkenyl) can be a variety of groups, such as alkyl, aryl, cyano (—CN), amino, sulfide, aldehyde, ester, ether, acid, hydroxyl or halide. Substituents can have a reactive group, such as but not limited to chloro, bromo, iodo, hydroxyl, or amino. Suitable substituents are selected from: —OR', =O, =NR', =N—OR', —NR'R", —SR', -halogen, —SiR'R"R"', —OC(O)R', —C(O)R', —CO$_2$R', —CONR'R,"—OC(O)NR'R", —NR"C(O)R', —NR'—C(O)NR"R"', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R," —CN and —NO$_2$ in a number ranging from zero to (2m'+1), where m' is the total number of carbon atoms in such radical. R', R" and R"' each independently refer to hydrogen, unsubstituted (C$_1$-C$_8$)alkyl and heteroalkyl, unsubstituted aryl, alkoxy or thioalkoxy groups, or aryl-(C$_1$-C$_4$)alkyl groups. When R' and R" are attached to the same nitrogen atom, they are combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

In other aspects, non-limiting examples of optional substituents include hydroxyl groups, sulfhydryl groups, halogens, amino groups, nitro groups, nitroso groups, cyano groups, azido groups, sulfoxide groups, sulfone groups, sulfonamide groups, carboxyl groups, carboxaldehyde groups, imine groups, alkyl groups, halo-alkyl groups, alkenyl groups, halo-alkenyl groups, alkynyl groups, halo-alkynyl groups, alkoxy groups, aryl groups, aryloxy groups, aralkyl groups, arylalkoxy groups, heterocyclyl groups, acyl groups, acyloxy groups, carbamate groups, amide groups, urethane groups, and ester groups.

As used herein, the term "alkyl" refers to a straight or branched, saturated, aliphatic radical having the number of carbon atoms indicated. For example, $C_1$-$C_6$ alkyl includes, but is not limited to, methyl, ethyl, propyl, isopropyl, butyl, isobutyl, sec-butyl, tert-butyl, pentyl, isopentyl, hexyl, etc. Other alkyl groups include, but are not limited to heptyl, octyl, nonyl, decyl, etc. Alkyl can include any number of carbons, such as 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 and 5-6. The alkyl group is typically monovalent, but is divalent, such as when the alkyl group links two moieties together. Non-limiting examples of alkyl groups include straight, branched, and cyclic alkyl groups. Alkyl groups can have, for example, 1, 2, 3, 4, 5, 6, 7, 8, 9, 10, 11, 12, 13, 14, 15, 16, 17, 18, 19, or 20 carbon atoms, from 1 to 20 carbon atoms ($C_1$-$C_{20}$ alkyl), from 1 to 10 carbon atoms ($C_1$-$C_{10}$ alkyl), from 1 to 6 carbon atoms ($C_1$-$C_6$ alkyl), from 1 to 3 carbon atoms ($C_1$-$C_3$ alkyl), from 3 to 10 carbon atoms ($C_3$-$C_{10}$ alkyl), or from 6 to 10 carbon atoms ($C_6$-$C_{10}$ alkyl). Non-limiting examples of straight alkyl groups include methyl, ethyl, propyl, butyl, pentyl, hexyl, heptyl, octyl, nonyl, and decyl.

Branched alkyl groups include any straight alkyl group substituted with any number of alkyl groups. Non-limiting examples of branched alkyl groups include isopropyl, isobutyl, sec-butyl, and t-butyl. Non-limiting examples of cyclic alkyl groups include cyclopropyl, cyclobutyl, cyclopentyl, cyclohexyl, cycloheptyl, and cyclooctyl groups. Cyclic alkyl groups also include fused-, bridged-, and spiro-bicycles and higher fused-, bridged-, and spiro-systems. A cyclic alkyl group can be substituted with any number of straight, branched, or cyclic alkyl groups.

As used herein, the term "alkenyl" refers to either a straight chain or branched hydrocarbon of 2 to 6 carbon atoms, having at least one double bond. Non-limiting examples of alkenyl groups include straight, branched, and cyclic alkenyl groups. The olefin or olefins of an alkenyl group can be, for example, E, Z, cis, trans, terminal, or exo-methylene. Alkenyl groups can have, for example, 2, 3, 4, 5, 6, 7, 8, 9, 10, 11, 12, 13, 14, 15, 16, 17, 18, 19, or 20 carbon atoms, from 2 to 20 carbon atoms ($C_2$-$C_{20}$ alkenyl), from 2 to 10 carbon atoms ($C_2$-$C_{10}$ alkenyl), from 2 to 6 carbon atoms ($C_2$-$C_6$ alkenyl), from 2 to 3 carbon atoms ($C_2$-$C_3$ alkenyl), from 3 to 10 carbon atoms ($C_3$-$C_{10}$ alkenyl), or from 6 to 10 carbon atoms ($C_6$-$C_{10}$ alkenyl).

As used herein, the term "alkynyl" refers to either a straight chain or branched hydrocarbon of 2 to 6 carbon atoms, having at least one triple bond. Non-limiting examples of alkynyl groups include straight, branched, and cyclic alkynyl groups. The triple bond of an alkynyl group can be internal or terminal. Alkynyl groups can have, for example, 2, 3, 4, 5, 6, 7, 8, 9, 10, 11, 12, 13, 14, 15, 16, 17, 18, 19, or 20 carbon atoms, from 2 to 20 carbon atoms ($C_2$-$C_{20}$ alkynyl), from 2 to 10 carbon atoms ($C_2$-$C_{10}$ alkynyl), from 2 to 6 carbon atoms ($C_2$-$C_6$ alkynyl), from 2 to 3 carbon atoms ($C_2$-$C_3$ alkynyl), from 3 to 10 carbon atoms ($C_3$-$C_{10}$ alkynyl), or from 6 to 10 carbon atoms ($C_6$-$C_{10}$ alkynyl).

As used herein, the term "alkenylene" refers to an alkenyl group, as defined above, linking at least two other groups, i.e., a divalent hydrocarbon radical. The two moieties linked to the alkenylene are linked to the same atom or different atoms of the alkenylene. Alkenylene groups include, but are not limited to, ethenylene, propenylene, isopropenylene, butenylene, isobutenylene, sec-butenylene, pentenylene and hexenylene.

As used herein, the term "alkynylene" refers to an alkynyl group, as defined above, linking at least two other groups, i.e., a divalent hydrocarbon radical. The two moieties linked to the alkynylene are linked to the same atom or different atoms of the alkynylene. Alkynylene groups include, but are not limited to, ethynylene, propynylene, isopropynylene, butynylene, sec-butynylene, pentynylene and hexynylene.

As used herein, the term "alkyl amine" refers to an alkyl groups as defined within, having one or more amino groups. The amino groups are primary, secondary or tertiary. The alkyl amine is further substituted with a hydroxy group. Alkyl amines can include, but are not limited to, ethyl amine, propyl amine, isopropyl amine, ethylene diamine and ethanolamine. The amino group can link the alkyl amine to the point of attachment with the rest of the compound, be at the omega position of the alkyl group, or link together at least two carbon atoms of the alkyl group.

As used herein, the term "cycloalkyl" refers to a saturated or partially unsaturated, monocyclic, fused bicyclic or bridged polycyclic ring assembly containing from 3 to 12 ring atoms, or the number of atoms indicated. Monocyclic rings include, for example, cyclopropyl, cyclobutyl, cyclopentyl, cyclohexyl, and cyclooctyl. Bicyclic and polycyclic rings include, for example, norbornane, decahydronaphthalene and adamantane. For example, $C_3$-$C_8$ cycloalkyl includes cyclopropyl, cyclobutyl, cyclopentyl, cyclohexyl, cyclooctyl, and norbornane.

As used herein, the term "cycloalkylene" refers to a cycloalkyl group, as defined above, linking at least two other groups, i.e., a divalent hydrocarbon radical. The two moieties linked to the cycloalkylene can be linked to the same atom or different atoms of the cycloalkylene. Cycloalkylene groups include, but are not limited to, cyclopropylene, cyclobutylene, cyclopentylene, cyclohexylene, and cyclooctylene.

As used herein, the term "heterocycloalkyl" refers to a ring system having from 3 ring members to about 20 ring members and from 1 to about 5 heteroatoms such as N, O and S. Additional heteroatoms are contemplated, including, but not limited to, B, Al, Si and P. In certain aspects, the heteroatoms are oxidized, such as, but not limited to, —S(O)— and —S(O)$_2$—.

As used herein, the term "heterocycloalkylene" refers to a heterocycloalkyl group, as defined above, linking at least two other groups. The two moieties linked to the heterocycloalkylene are linked to the same atom or different atoms of the heterocycloalkylene.

A heterocycle can be any ring containing a ring atom that is not carbon. A heterocycle can be substituted with any number of substituents, for example, alkyl groups and halogen atoms. A heterocycle can be aromatic or non-aromatic. Non-limiting examples of heterocycles include pyrrole, pyrrolidine, pyridine, piperidine, succinamide, maleimide, morpholine, imidazole, thiophene, furan, tetrahydrofuran, pyran, and tetrahydropyran.

As used herein, the term "halo," "halogen" or "halide" refers to fluorine, chlorine, bromine and iodine. In certain aspects, halogen (halo) is chloro or fluoro. In further aspects, halogen (halo) is chloro, fluro, bromo or iodo. As used herein, the term "halo-alkoxy" refers to an alkoxy group having at least one halogen. Halo-alkoxy is as defined for alkoxy where some or all of the hydrogen atoms are substituted with halogen atoms. In certain aspects, the alkoxy groups are substituted with 1, 2, 3, or more halogens. When all the hydrogens are replaced with a halogen, for example by fluorine, the compounds are per-substituted, for example, perfluorinated. Halo-alkoxy includes, but is not limited to, trifluoromethoxy, 2,2,2,-trifluoroethoxy, perfluoroethoxy, and the like.

A halo-alkyl group can be any alkyl group substituted with any number of halogen atoms, for example, fluorine, chlorine, bromine, and iodine atoms. A halo-alkenyl group can be any alkenyl group substituted with any number of halogen atoms. A halo-alkynyl group can be any alkynyl group substituted with any number of halogen atoms.

As used herein, the term "alkoxy" refers to an alkyl group having an oxygen atom that either connects the alkoxy group to the point of attachment or is linked to two carbons of the alkoxy group. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups are further substituted with a variety of substituents described within. For example, the alkoxy groups are substituted with halogens to form a "halo-alkoxy" group. An alkoxy group can be, for example, an oxygen atom substituted with any alkyl, alkenyl, or alkynyl group. An ether or an ether group comprises an alkoxy group. Non-limiting examples of alkoxy groups include methoxy, ethoxy, propoxy, isopropoxy, and isobutoxy.

As used herein, the term "aryl" refers to a monocyclic or fused bicyclic, tricyclic or greater, aromatic ring assembly containing 6 to 16 ring carbon atoms. "Arylene" means a divalent radical derived from an aryl group. Aryl groups are mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g., methylenedioxy or ethylenedioxy. Oxy-$C_2$-$C_3$-alkylene is also a divalent substituent attached to two adjacent carbon atoms of phenyl, e.g., oxyethylene or oxypropylene. An example for oxy-$C_2$-$C_3$-alkylene-phenyl is 2,3-dihydrobenzofuran-5-yl.

An aryl group can be heterocyclic or non-heterocyclic. An aryl group can be monocyclic or polycyclic. An aryl group can be substituted with any number of substituents, for example, hydrocarbyl groups, alkyl groups, alkoxy groups, and halogen atoms. Non-limiting examples of aryl groups include phenyl, toluyl, naphthyl, pyrrolyl, pyridyl, imidazolyl, thiophenyl, and furyl.

As used herein, the terms "alkoxy-aryl" or "aryloxy" refers to an aryl group, as defined above, where one of the moieties linked to the aryl is linked through an oxygen atom. Alkoxy-aryl groups include, but are not limited to, phenoxy ($C_6H_5O^-$). The present disclosure also includes alkoxy-heteroaryl or heteroaryloxy groups. In some aspects, an aryloxy group can be, for example, an oxygen atom substituted with any aryl group, such as phenoxy.

As used herein, the term "heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g., alkyl, nitro or halogen. Suitable groups for the present disclosure also include heteroarylene and heteroarylene-oxy groups similar to the description above for arylene and arylene-oxy groups.

Similarly, aryl and heteroaryl groups described herein are substituted or unsubstituted. Substituents for the aryl and heteroaryl groups are varied, such as alkyl, aryl, CN, amino, sulfide, aldehyde, ester, ether, acid, hydroxyl or halide. In some aspects, a substituent is a reactive group, such as but not limited to chloro, bromo, iodo, hydroxyl, or amino. In certain aspects, a substituent is selected from: -halogen, —OR', —OC(O)R', —NR'R",-SR', —R', —CN, —NO$_2$, —CO$_2$R', —CONR'R,"-C(O)R', —OC(O)NR'R,"—NR"C(O)R', —NR"C(O)2R', —NR'—C(O)NR"R'", —NH—C(NH$_2$)═NH, —NR'C(NH$_2$)═NH, —NH—C(NH$_2$)═NR', —S(O)R', —S(O)$_2$R', —S(O)$_2$NR'R,"-N$_3$, —CH(Ph)$_2$, in a number ranging from zero to the total number of open valences on the aromatic ring system; and where R', R" and R'" are independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

As used herein, the term "alkyl-aryl" refers to a radical having an alkyl component and an aryl component, where the alkyl component links the aryl component to the point of attachment. The alkyl component is as defined above, except that the alkyl component is at least divalent in order to link to the aryl component and to the point of attachment. In some aspects, the alkyl component is absent. The aryl component is as defined above. Examples of alkyl-aryl groups include, but are not limited to, benzyl. The present disclosure also includes alkyl-heteroaryl groups.

As used herein, the term "alkenyl-aryl" refers to a radical having both an alkenyl component and an aryl component, where the alkenyl component links the aryl component to the point of attachment. The alkenyl component is as defined above, except that the alkenyl component is at least divalent in order to link to the aryl component and to the point of attachment. The aryl component is as defined above. Examples of alkenyl-aryl include ethenyl-phenyl, among others. The present disclosure also includes alkenyl-heteroaryl groups.

As used herein, the term "alkynyl-aryl" refers to a radical having both an alkynyl component and an aryl component, where the alkynyl component links the aryl component to the point of attachment. The alkynyl component is as defined above, except that the alkynyl component is at least divalent in order to link to the aryl component and to the point of attachment. The aryl component is as defined above. Examples of alkynyl-aryl include ethynyl-phenyl, among others. The present disclosure also includes alkynyl-heteroaryl groups.

An aralkyl group can be, for example, any alkyl group substituted with any aryl group, such as benzyl.

An arylalkoxy group can be, for example, an oxygen atom substituted with any aralkyl group, such as benzyloxy.

An acyl group can be, for example, a carbonyl group substituted with hydrocarbyl, alkyl, hydrocarbyloxy, alkoxy, aryl, aryloxy, aralkyl, arylalkoxy, or a heterocycle. Non-limiting examples of acyl include acetyl, benzoyl, benzyloxycarbonyl, phenoxycarbonyl, methoxycarbonyl, and ethoxycarbonyl.

An acyloxy group can be an oxygen atom substituted with an acyl group. An ester or an ester group comprises an acyloxy group. A non-limiting example of an acyloxy group, or an ester group, is acetate.

A carbamate group can be an oxygen atom substituted with a carbamoyl group, wherein the nitrogen atom of the carbamoyl group is unsubstituted, monosubstituted, or disubstituted with one or more of hydrocarbyl, alkyl, aryl, heterocyclyl, or aralkyl. When the nitrogen atom is disubstituted, the two substituents together with the nitrogen atom can form a heterocycle.

The disclosure provides the use of salts of any compound described herein. Salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some cases, a salt is a metal salt. In some cases, a salt is an ammonium salt.

Metal salts can arise from the addition of an inorganic base to a compound of the disclosure. The inorganic base consists of a metal cation paired with a basic counterion, such as, for example, hydroxide, carbonate, bicarbonate, or phosphate. The metal can be an alkali metal, alkaline earth metal, transition metal, or main group metal. In some cases, the metal is lithium, sodium, potassium, cesium, cerium, magnesium, manganese, iron, calcium, strontium, cobalt, titanium, aluminum, copper, cadmium, or zinc.

In some cases, a metal salt is a lithium salt, a sodium salt, a potassium salt, a cesium salt, a cerium salt, a magnesium salt, a manganese salt, a iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound of the disclosure. In some cases, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrrazole, pipyrrazole, imidazole, pyrazine, or pipyrazine.

In some cases, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrrazole salt, a pipyrrazole salt, an imidazole salt, a pyrazine salt, or a pipyrazine salt.

Acid addition salts can arise from the addition of an acid to a compound of the disclosure. In some cases, the acid is organic. In some cases, the acid is inorganic. In some cases, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some cases, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a methanesulfonate (mesylate) salt, an ethanesulfonate salt, a benzenesulfonate salt, a p-toluenesulfonate salt, a citrate salt, an oxalate salt, or a maleate salt.

Solubility

Polymer dots of the disclosure, or fragments or chemical precursors thereof, can be soluble or insoluble in various solvents. Types of solvents include, for example, polar solvents, non-polar solvents, aqueous solvents, non-aqueous solvents, ionic liquids, organic solvents, and polymeric solvents. Non-limiting examples of solvents include: water; tetrahydrofuran (THF); morpholine; N-methylmorpholine; methanol (MeOH); ethanol (EtOH); propanol (PrOH); isopropanol (iPrOH); t-butanol (tBuOH); acetic acid (AcOH); ethylene glycol; propylene glycol; methyl acetate (MeOAc); ethyl acetate (EtOAc); ether ($Et_2O$); methyl-tert-butyl ether (MTBE); dimethoxyethane (DME); glyme; diglyme; tetraglyme; methylene chloride ($CH_2Cl_2$); chloroform ($CHCl_3$); carbon tetrachloride ($CCl_4$); 1,1-dichloroethane ($CHCl_2CH_3$); 1,2-dichloroethane ($CH_2ClCH_2Cl$); carbon disulfide ($CS_2$); dimethyl sulfoxide (DMSO); dimethylformamide (DMF); acetone (MeAc); 2-butanone (EtAc); pentane, hexane, hexanes, cyclohexane; benzene; toluene; xylene; xylenes; and pyridine.

Polymer dots of the disclosure, or fragments or chemical precursors thereof, can be physically associated or chemically linked with polyethylene glycol (PEG) groups. A PEG group can include, for example, about 2, about 4, about 6, about 8, about 10, about 20, about 30, about 40, about 50, about 60, about 70, about 80, about 90, about 100, about 150, about 200, about 250, about 300, about 350, about 400, about 450, about 500, about 550, about 600, about 650, about 700, about 750, about 800, about 850, about 900, about 950, about 1000, about 1250, about 1500, about 1750, about 2000, about 2250, about 2500, about 2750, about 3000, about 3250, about 3500, about 3750, about 4000, about 4250, about 4500, about 4750, or about 5000 ethylene glycol subunits. One or more ethylene glycol submits can be modified with any substituent described herein, for example, hydroxyl groups, sulfhydryl groups, halogens, amino groups, nitro groups, nitroso groups, cyano groups, azido groups, sulfoxide groups, sulfone groups, sulfonamide groups, carboxyl groups, carboxaldehyde groups, imine groups, alkyl groups, halo-alkyl groups, alkenyl groups, halo-alkenyl groups, alkynyl groups, halo-alkynyl groups, alkoxy groups, aryl groups, aryloxy groups, aralkyl groups, arylalkoxy groups, heterocyclyl groups, acyl groups, acyloxy groups, carbamate groups, amide groups, urethane groups, and ester groups.

Pdot Features

In some cases, fluorine may be used to enhance characteristics of polymer chains for use in various applications. Fluorine may influence the polymer properties by (1) affecting the polymer solubility as well as the Pdot preparation by nanoprecipitation method, (2) having a minimal effect on steric hindrance due to the small size of the fluorine atom, (3) being biocompatible, (4) increasing the quantum yield of the polymer both in solution and in the Pdot form, (5) reducing nonspecific adsorption in biological applications as compared to the non-fluorinated polymer, (6) providing a micro-hydrophobic environment for blending and doping of different hydrophobic species, and (7) having a molar absorption coefficient that is higher than that of the non-fluorinated polymer. In some cases, the composition may comprise a fluorinated polymer dot wherein a nonspecific adsorption of the non-fluorinated polymer dot is higher than a nonspecific adsorption of the polymer dot of an analogous polymer dot that is fluorinated. For example, the nonspecific adsorption of the non-fluorinated polymer dot may be greater than five-fold higher than a nonspecific adsorption of the polymer dot of an analogous polymer dot that is fluorinated.

In some cases, the solubility of fluorinated Pdots is affected by the fluorine content in the conjugated polymers. In a preferable case, the fluorine content is less than 50% by mass so that the fluorinated polymer is highly soluble in a general non-fluorous organic solvent, such as tetrahydrofuran (THF). As a result, the Pdots can be prepared by a nanoprecipitation method involving mixing the polymer in THF solution with water. The fluorine content can be varied from 0 to 50% by mass to tune the solubility of the fluorinated polymer. In some cases, the polymer has a solubility in a non-fluorous solvent higher than 0.001 mg/mL. In some cases, the polymer has a solubility in a non-fluorous solvent higher than 0.01 mg/mL. In some cases, the polymer has a solubility in a non-fluorous solvent higher than 0.1 mg/mL. In some cases, the polymer has a solubility in a non-fluorous solvent higher than 1 mg/mL. In some cases, the polymer has a solubility in a non-fluorous solvent higher than 10 mg/mL, or higher.

In some cases, the nonspecific adsorption properties of fluorinated Pdots is affected by the fluorine content in the conjugated polymers. In a preferable case, the fluorine content is less than 50% by mass so that the fluorinated Pdots so that can be prepared by a nanoprecipitation method involving mixing the polymer in THF solution with water. The fluorine content can be varied from 0 to 50% by mass to tune the nonspecific adsorption of the fluorinated Pdots in biological applications. In some cases, the fluorinated Pdots has nonspecific labeling brightness that is 2 times less than that of the non-fluorinated Pdots. In some cases, the fluorinated Pdots has nonspecific labeling brightness that is 3 times less than that of the non-fluorinated Pdots. In some cases, the fluorinated Pdots has nonspecific labeling brightness that is 4 times less than that of the non-fluorinated Pdots. In some cases, the fluorinated Pdots has nonspecific labeling brightness that is 5 times less than that of the non-fluorinated Pdots. In some cases, the fluorinated Pdots has nonspecific labeling brightness that is 6 times less than that of the non-fluorinated Pdots. In some cases, the fluorinated Pdots has nonspecific labeling brightness that is 7 times less than that of the non-fluorinated Pdots. In some cases, the fluorinated Pdots has nonspecific labeling brightness that is 8 times less than that of the non-fluorinated Pdots. In some cases, the fluorinated Pdots has nonspecific labeling brightness that is 9 times less than that of the non-fluorinated Pdots. In some cases, the fluorinated Pdots has nonspecific labeling brightness that is 10 times less than that of the non-fluorinated Pdots. In some cases, the fluorinated Pdots has nonspecific labeling brightness that is 10 to 15 times less than that of the non-fluorinated Pdots. In some cases, the fluorinated Pdots has nonspecific labeling brightness that is 15 to 20 times less than that of the non-fluorinated Pdots. In some cases, the fluorinated Pdots has nonspecific labeling brightness that is more than 10 times less than that of the non-fluorinated Pdots.

This disclosure provides Pdots with different shapes and sizes. In some cases, the shape and size of fluorinated Pdots is affected by the fluorine content in the conjugated polymers. In a preferable case, the fluorine content can be varied from 0 to 50% by mass to tune the shape and size of the fluorinated Pdots. In some cases, the composition may comprise a fluorinated polymer dot wherein the fluorinated polymer dot has a non-spherical shape. In some cases, Pdots may have a spheroid shape. In other cases, Pdots may have an ellipsoid shape. In other cases, Pdots may have a rod shape. In other cases, Pdots may have a cylinder shape. In other cases, Pdots may have a tube shape. In other cases, Pdots may have any of, but are not limited to, the following shapes, helix, ellipse, parabola, hyperbola, polygon, apeirogon, chiliagon, decagon, enneagon, googolgon, hectagon, heptagon, hendecagon, hexagon, megagon, myraigon, octagon, pentagon, quadrilateral, triangle, trapezium, cylinder, hyperplane, plane, platonic solid, dodecahedron, hexahedron, icosahedrons, octahedron, tetrahedron, torus, quadric, done, cylinder, sphere, hyperboloid, paraboloid, polychoron, hecatonicosachoron, hexacosichoron, hexadecachoron, icositetrachoron, pentachoron, tesseract or a spherical cone.

The shape may be a function of the case ratio. In one case, the Pdot may be a fluorinated Pdot. In this case, the fluorinated Pdot is PFDPFBT and can be mixed with PSPEGCOOH. In this case, the shape of PFDPFBT may be a rod or ellipsoidal shapes (FIG. 1B). The case ratio can be greater than 1.0 and less than 4.0. The length can be greater than 10 nm and less than 50 nm. In the case of PFDPFBT and PSPEGCOOH, the case ratio can be between 1.6 and 3. In this case, the length of PFDPFBT and PSPEGCOOH can be between 20 and 40 nm.

The shape of the Pdot may change. In some cases, the shape may change depending on the material that is blended with the Pdot. The Pdot may have a first shape in a first material and a second shape in a second material. For example, the Pdot may be spheroid in a first solvent or first material and in a second material, the Pdot may be ellipsoid. In some cases, the first solvent is tetrahydrafuran and the second material is PSPEGCOOH. In particular cases, the Pdot is PFDPFBT and it has a spheroid shape in certain solvents such as tetrahydrafuran and an ellipsoidal shape in materials such as PSPEGCOOH.

Sizes of Pdots

In some cases, the size of the Pdot may be a function of the chemical structure. In these cases, the number of substitutions to the Pdot backbone can affect the size of the Pdot. In some cases, the Pdot is mixed with a solid substance. In these cases, the solid substance may affect the size of the Pdot. The size of the Pdot can be measured by the diameter. Pdots without a fluorine substitution may have a diameter less than or equal to about 25 nm, about 20 nm, about 15 nm, about 14 nm, about 13 nm, about 12 nm, about 11 nm, about 10 nm, about 5 nm, or about 4 nm. Pdots with fluorine atom substitutions may have a diameter less than or equal to about 100 nm, 75 nm, 60 nm, 55 nm, 50 nm, 45 nm, 40 nm, 35 nm, 30 nm, 25 nm, 20 nm, 15 nm, 10 nm, 5 nm or 4 nm.

In some cases, the Pdot without a fluorine substitution may be PFDPBT. In some cases, the Pdot is mixed with a chemical conjugate such as PS-PEG-COOH and the diameter may be less than 30 nm, 25 nm, 20 nm, 15 nm, 14 nm, 12 nm, 10 nm, 5 nm, etc. For example, the diameter may be about 14 nm (see, e.g., FIG. 1A).

In some cases, the Pdot with a fluorine substitution may be PFDPFBT. The Pdot may be mixed with PS-PEG-COOH and the diameter may be at least 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm or 30 nm. In some cases, the Pdot has a diameter of at most 20 nm, 21 nm, 22 nm, 23 nm, 24 nm, 25 nm, 26 nm, 27 nm, 28 nm, 29 nm, 30 nm, 31 nm, 32 nm, 33 nm, 34 nm, 35 nm, 36 nm, 37 nm, 38 nm, 39 nm, 40 nm, 41 nm, 42 nm, 43 nm, 44 nm, 45 nm, 46 nm, 47 nm, 48 nm, 49 nm, 50 nm, 51 nm, 52 nm, 53 nm, 54 nm, 55 nm, 56 nm, 57 nm, 58 nm, 59 nm or 60 nm. In some cases, the Pdot has a diameter within the following ranges, 4-10 nm, 5-15 nm, 10-20 nm, 15-25 nm, 20-30 nm, 25-35 nm, 30-40 nm, 35-45 nm, 40-50 nm, 45-55 nm or 50-60 nm (see, e.g., FIG. 1C).

In some cases, the Pdot (e.g., PFDPDFBT) is mixed with PSPEG and the diameter is about 12 nm, about 13 nm, about 14 nm, about 15 nm, about 16 nm, about 17 nm, about 18 nm, about 19 nm, or about 20 nm. In some cases, the Pdot (e.g., PFDPDFBT) is mixed with PSMA and the diameter is may be at least 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm or 30 nm. In some cases, the Pdot has a diameter of at most 20 nm, 21 nm, 22 nm, 23 nm, 24 nm, 25 nm, 26 nm, 27 nm, 28 nm, 29 nm, 30 nm, 31 nm, 32 nm, 33 nm, 34 nm, 35 nm, 36 nm, 37 nm, 38 nm, 39 nm, 40 nm, 41 nm, 42 nm, 43 nm, 44 nm, 45 nm, 46 nm, 47 nm, 48 nm, 49 nm, 50 nm, 51 nm, 52 nm, 53 nm, 54 nm, 55 nm, 56 nm, 57 nm, 58 nm, 59 nm or 60 nm. In some cases, the Pdot has a diameter within the following ranges, 4-10 nm, 5-15 nm, 10-20 nm, 15-25 nm, 20-30 nm, 25-35 nm, 30-40 nm, 35-45 nm, 40-50 nm, 45-55 nm or 50-60 nm. In some cases, the Pdot (e.g., PFDPDFBT) is not mixed with a chemical conjugate and the diameter is may be at least 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm or 30 nm. In some cases, the Pdot has a diameter of at most 20 nm, 21 nm, 22 nm, 23 nm, 24 nm, 25 nm, 26 nm, 27 nm, 28 nm, 29 nm, 30 nm, 31 nm, 32 nm, 33 nm, 34 nm, 35 nm, 36 nm, 37 nm, 38 nm, 39 nm, 40 nm, 41 nm, 42 nm, 43 nm, 44 nm, 45 nm, 46 nm, 47 nm, 48 nm, 49 nm, 50 nm, 51 nm, 52 nm, 53 nm, 54 nm, 55 nm, 56 nm, 57 nm, 58 nm, 59 nm or 60 nm. In some cases, the Pdot has a diameter within the following ranges, 4-10 nm, 5-15 nm, 10-20 nm, 15-25 nm, 20-30 nm, 25-35 nm, 30-40 nm, 35-45 nm, 40-50 nm, 45-55 nm or 50-60 nm.

In some cases, the Pdot (e.g., PFB) is mixed with PSMA and the diameter may be at least 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm or 30 nm. In some cases, the Pdot has a diameter of at most 20 nm, 21 nm, 22 nm, 23 nm, 24 nm, 25 nm, 26 nm, 27 nm, 28 nm, 29 nm, 30 nm, 31 nm, 32 nm, 33 nm, 34 nm, 35 nm, 36 nm, 37 nm, 38 nm, 39 nm, 40 nm, 41 nm, 42 nm, 43 nm, 44 nm, 45 nm, 46 nm, 47 nm, 48 nm, 49 nm, 50 nm, 51 nm, 52 nm, 53 nm, 54 nm, 55 nm, 56 nm, 57 nm, 58 nm, 59 nm or 60 nm. In some cases, the Pdot has a diameter within the following ranges, 4-10 nm, 5-15 nm, 10-20 nm, 15-25 nm, 20-30 nm, 25-35 nm, 30-40 nm, 35-45 nm, 40-50 nm, 45-55 nm or 50-60 nm.

In some cases, the Pdot (e.g., PFDFB) is mixed with PSMA and the diameter may be at least 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm or 30 nm. In some cases, the Pdot has a diameter of at most 20 nm, 21 nm, 22 nm, 23 nm, 24 nm, 25 nm, 26 nm, 27 nm, 28 nm, 29 nm, 30 nm, 31 nm, 32 nm, 33 nm, 34 nm, 35 nm, 36 nm, 37 nm, 38 nm, 39 nm, 40 nm, 41 nm, 42 nm, 43 nm, 44 nm, 45 nm, 46 nm, 47 nm, 48 nm, 49 nm, 50 nm, 51 nm, 52 nm, 53 nm, 54 nm, 55 nm, 56 nm, 57 nm, 58 nm, 59 nm or 60 nm. In some cases, the Pdot has a diameter within the following ranges, 4-10 nm, 5-15 nm, 10-20 nm, 15-25 nm, 20-30 nm, 25-35 nm, 30-40 nm, 35-45 nm, 40-50 nm, 45-55 nm or 50-60 nm. In some cases the Pdot is (e.g. PFDFB). In this case, the Pdot is mixed with PSPEG and the diameter may be at least 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm or 30 nm. In some cases, the Pdot has a diameter of at most 20 nm, 21 nm, 22 nm, 23 nm, 24 nm, 25 nm, 26 nm, 27 nm, 28 nm, 29 nm, 30 nm, 31 nm, 32 nm, 33 nm, 34 nm, 35 nm, 36 nm, 37 nm, 38 nm, 39 nm, 40 nm, 41 nm, 42 nm, 43 nm, 44 nm, 45 nm, 46 nm, 47 nm, 48 nm, 49 nm, 50 nm, 51 nm, 52 nm, 53 nm, 54 nm, 55 nm, 56 nm, 57 nm, 58 nm, 59 nm or 60 nm. In some cases, the Pdot has a diameter within the following ranges, 4-10 nm, 5-15 nm, 10-20 nm, 15-25 nm, 20-30 nm, 25-35 nm, 30-40 nm, 35-45 nm, 40-50 nm, 45-55 nm or 50-60 nm.

In some cases the Pdot is (e.g., PFDFB). In this case, the Pdot is mixed with PSPEG and the diameter may be at least 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm or 30 nm. In some cases, the Pdot has a diameter of at most 20 nm, 21 nm, 22 nm, 23 nm, 24 nm, 25 nm, 26 nm, 27 nm, 28 nm, 29 nm, 30 nm, 31 nm, 32 nm, 33 nm, 34 nm, 35 nm, 36 nm, 37 nm, 38 nm, 39 nm, 40 nm, 41 nm, 42 nm, 43 nm, 44 nm, 45 nm, 46 nm, 47 nm, 48 nm, 49 nm, 50 nm, 51 nm, 52 nm, 53 nm, 54 nm, 55 nm, 56 nm, 57 nm, 58 nm, 59 nm or 60 nm. In some cases, the Pdot has a diameter within the following ranges, 4-10 nm, 5-15 nm, 10-20 nm, 15-25 nm, 20-30 nm, 25-35 nm, 30-40 nm, 35-45 nm, 40-50 nm, 45-55 nm or 50-60 nm.

In some cases the Pdot is (e.g., PFDFB). In this case, the diameter is may be at least 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm or 30 nm. In some cases, the Pdot has a diameter of at most 20 nm, 21 nm, 22 nm, 23 nm, 24 nm, 25 nm, 26 nm, 27 nm, 28 nm, 29 nm, 30 nm, 31 nm, 32 nm, 33 nm, 34 nm, 35 nm, 36 nm, 37 nm, 38 nm, 39 nm, 40 nm, 41 nm, 42 nm, 43 nm, 44 nm, 45 nm, 46 nm, 47 nm, 48 nm, 49 nm, 50 nm, 51 nm, 52 nm, 53 nm, 54 nm, 55 nm, 56 nm, 57 nm, 58 nm, 59 nm or 60 nm. In some cases, the Pdot has a diameter within the following ranges, 4-10 nm, 5-15 nm, 10-20 nm, 15-25 nm, 20-30 nm, 25-35 nm, 30-40 nm, 35-45 nm, 40-50 nm, 45-55 nm or 50-60 nm.

In some cases the Pdot is (e.g., PFB). In this case, the diameter may be at least 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm or 30 nm. In some cases, the Pdot has a diameter of at most 20 nm, 21 nm, 22 nm, 23 nm, 24 nm, 25 nm, 26 nm, 27 nm, 28 nm, 29 nm, 30 nm, 31 nm, 32 nm, 33 nm, 34 nm, 35 nm, 36 nm, 37 nm, 38 nm, 39 nm, 40 nm, 41 nm, 42 nm, 43 nm, 44 nm, 45 nm, 46 nm, 47 nm, 48 nm, 49 nm, 50 nm, 51 nm, 52 nm, 53 nm, 54 nm, 55 nm, 56 nm, 57 nm, 58 nm, 59 nm or 60 nm. In some cases, the Pdot has a diameter within the following ranges, 4-10 nm, 5-15 nm, 10-20 nm, 15-25 nm, 20-30 nm, 25-35 nm, 30-40 nm, 35-45 nm, 40-50 nm, 45-55 nm or 50-60 nm.

The size of a Pdot may also be a function of the affinity for aqueous solutions. The number of substitutions to the Pdot backbone may affect the size of the Pdot. The effect of aqueous solutions on the size of the Pdot can be to reduce or increase hydrodynamic diameter. Pdots without a fluorine substitution may have a hydrodynamic diameter less than or equal to about 25 nm, about 20 nm, about 15 nm, about 14 nm, about 13 nm, about 12 nm, about 11 nm, about 10 nm, about 5 nm, about 2 nm, or about 1 nm. Pdots with fluorine atom substitutions may have a hydrodynamic diameter less than or equal to 100 nm, 75 nm, 60 nm, 55 nm, 50 nm, 45 nm, 40 nm, 35 nm, 30 nm, 25 nm, 20 nm, 15 nm, 10 nm, 5 nm, 4 nm, 3 nm, 2 nm or 1 nm.

In some cases, the Pdot without a fluorine substitution may be PFDPBT and the hydrodynamic diameter may be at least 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm or 30 nm. In some cases, the Pdot has a diameter of at most 20 nm, 21 nm, 22 nm, 23 nm, 24 nm, 25 nm, 26 nm, 27 nm, 28 nm, 29 nm, 30 nm, 31 nm, 32 nm, 33 nm, 34 nm, 35 nm, 36 nm, 37 nm, 38 nm, 39 nm, 40 nm, 41 nm, 42 nm, 43 nm, 44 nm, 45 nm, 46 nm, 47 nm, 48 nm, 49 nm, 50 nm, 51 nm, 52 nm, 53 nm, 54 nm, 55 nm, 56 nm, 57 nm, 58 nm, 59 nm or 60 nm. In some cases, the Pdot has a diameter within the following ranges, 5-25 nm, 10-30 nm, 25-35 nm, 25-45 nm, 30-50 nm, 35-55 nm or 40-60 nm (see, e.g., FIG. 1A).

In some cases, the Pdot with a fluorine substitution may be (e.g., PFDPFBT) and the hydrodynamic diameter may be at least 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm or 30 nm. In some cases, the Pdot has a diameter of at most 20 nm, 21 nm, 22 nm, 23 nm, 24 nm, 25 nm, 26 nm, 27 nm, 28 nm, 29 nm, 30 nm, 31 nm, 32 nm, 33 nm, 34 nm, 35 nm, 36 nm, 37 nm, 38 nm, 39 nm, 40 nm, 41 nm, 42 nm, 43 nm, 44 nm, 45 nm, 46 nm, 47 nm, 48 nm, 49 nm, 50 nm, 51 nm, 52 nm, 53 nm, 54 nm, 55 nm, 56 nm, 57 nm, 58 nm, 59 nm or 60 nm. In some cases, the Pdot has a diameter within the following ranges, 5-25 nm, 10-30 nm, 25-35 nm, 25-45 nm, 30-50 nm, 35-55 nm or 40-60 nm. (see, e.g., FIG. 1C).

The shape and size of the Pdot can be determined using specific methods. These methods may include light scattering (DLS) and transmission electron microscopy (TEM). Other methods may include but are not limited to scanning electron microscopy (SEM), atomic force microscopy (AFM).

Quantum Yield

In some cases, the fluorescence quantum yield of fluorinated Pdots is affected by the fluorine content in the conjugated polymers. The quantum yield, for example, can be the ratio of photons emitted relative to the photons absorbed by a molecule. Often the percentage of the quantum yield can be measured by the fraction that relaxes by emitting photon over the total number that relaxes to the ground state. In some cases, when a Pdot or any dye is excited to an excited state, it can relax down to the ground state by emitting a photon or not. Often, the composition may comprise a fluorinated polymer dot wherein the fluorinated polymer dot has a quantum yield that is greater than a quantum yield of an analogous polymer dot that is non-fluorinated. For example, the quantum yield of the non-fluorinated polymer dot is greater than five-fold higher than a quantum yield of an analogous polymer dot that is fluorinated.

In some cases, the fluorine content is less than 50% by mass so that the fluorinated Pdots so that can be prepared by a nanoprecipitation method involving mixing the polymer in THF solution with water. The fluorine content can be varied from 0 to 50% by mass to increase the fluorescence quantum yield of the fluorinated Pdots in biological applications. The fluorescence quantum yield of the fluorinated Pdots can vary from 1% to 100%. In some cases, the fluorinated Pdots has a fluorescence quantum yield higher than 90%, higher than 80%, higher than 70%, higher than 60%, higher than 50%, higher than 40%, higher than 30%, higher than 20%, higher than 10%, higher than 50%. In some cases, the fluorinated Pdots has a fluorescence quantum yield that equal to or is higher than that of the non-fluorinated Pdots. In some cases, the fluorinated Pdots has a fluorescence quantum yield that is 1.5 times higher than that of the non-fluorinated Pdots. In some cases, the fluorinated Pdots has a fluorescence quantum yield that is 2 times higher than that of the non-fluorinated Pdots. In some cases, the fluorinated Pdots has a fluorescence quantum yield that is 2.5 times higher than that of the non-fluorinated Pdots. In some cases, the fluorinated Pdots has a fluorescence quantum yield that is 3 times higher than that of the non-fluorinated Pdots. In some cases, the fluorinated Pdots has a fluorescence quantum yield that is 3.5 times higher than that of the non-fluorinated Pdots. In some cases, the fluorinated Pdots has a fluorescence quantum yield that is 4 times higher than that of the non-fluorinated Pdots. In some cases, the fluorinated Pdots has a fluorescence quantum yield that is 4.5 times higher than that of the non-fluorinated Pdots. In some cases, the fluorinated Pdots has a fluorescence quantum yield that is 5 times higher than that of the non-fluorinated Pdots. In some cases, the fluorinated Pdots has a fluorescence quantum yield that is more than 5 times higher than that of the non-fluorinated Pdots.

In some cases, the quantum yield of the Pdot may be a function of the chemical structure. Pdots without a fluorine substitution may have a quantum yield greater than or equal to about 30%, about 20%, about 10%, or about 1%. In some cases, the Pdot (e.g., PFDPBT) may be bare in aqueous solution and the quantum yield may be greater than 40%, 30%, 20%, 10% or 1%. In some cases, the Pdot may have a quantum yield within the following ranges, 1-10%, 5-15%, 10-20%, 15-25%, 20-30%, 25-35%, 30-40% or greater than 40%. In some cases, the Pdot is mixed with a solid substance. In some cases, the solid substance may affect the quantum yield of the Pdot. In another case, the PFDPBT may be mixed with solid substance (e.g., PS-PEG-COOH) and the quantum yield may be greater than 10%, or 1%. In some cases, the Pdot may have a quantum yield within the following ranges, 1-10% or greater than 10%.

In some cases, the number of substitutions to the Pdot backbone can affect the quantum yield of the Pdot. Pdots with fluorine atom substitutions may have a quantum yield greater than or equal to about 40%, about 30%, about 20% about 10%, or about 1%. In some cases, the Pdot with a fluorine substitution (e.g., PFDPFBT) may be mixed with solid substance PS-PEG-COOH and the quantum yield may be greater than 50%, 40%, 30%, 20%, 10%, or 1%. In some cases, the Pdot may have a quantum yield within the following ranges, 1-10%, 5-15%, 10-20%, 15-25%, 20-30%, 25-35%, 30-40%, 35-45%, 40-50%, or greater than 50%. In some cases, the Pdot (e.g., PFDPDFBT) may be mixed with solid substance PSPEG and the quantum yield may be greater than 40%, 30%, 20%, 10%, or 1%. In some cases, the Pdot may have a quantum yield within the following ranges, 1-10%, 5-15%, 10-20%, 15-25%, 20-30%, 25-35%, 30-40% or greater than 40%. In some cases, the Pdot (e.g., PFDPDFBT) may be mixed with solid substance PSMA and the quantum yield may be greater than 40%, 30%, 20%, 10%, or 1%. In some cases, the Pdot may have a quantum yield within the following ranges, 1-10%, 5-15%, 10-20%, 15-25%, 20-30%, 25-35%, 30-40% or greater than 40%. In some cases, the Pdot (e.g., PFDPDFBT) may be bare and the quantum yield may be greater than 40%, 30%, 20%, 10%, or 1%. In some cases, the Pdot may have a quantum yield within the following ranges, 1-10%, 5-15%, 10-20%, 15-25%, 20-30%, 25-35%, 30-40% or greater than 40%.

In some cases, the Pdot (e.g., PFDFB) may be mixed with solid substance PSMA and the quantum yield may be greater than 30%, 20%, 10%, or 1%. In some cases, the Pdot may have a quantum yield within the following ranges, 1-10%, 5-15%, 10-20%, 15-25%, 20-30%, or greater than 30%. In some cases, the Pdot (e.g., PFDFB) may be mixed with solid substance PSPEG and the quantum yield may be greater than 40%, 30%, 20%, 10%, or 1%. In some cases, the Pdot may have a quantum yield within the following ranges, 1-10%, 5-15%, 10-20%, 15-25%, 20-30%, 25-35%, 30-40% or greater than 40%. In some cases, the Pdot (e.g., PFDFB) quantum yield may be greater than 40%, 30%, 20%, 10%, or 1%. In some cases, the Pdot may have a quantum yield within the following ranges, 1-10%, 5-15%, 10-20%, 15-25%, 20-30%, 25-35%, 30-40% or greater than 40%.

In some cases, Pdots may not have any substitutions. In some cases, Pdots without any substitutions may have a quantum yield greater than or equal to about 40%, 30%, 20%, 10%, or 1%. In some cases, the quantum yield of the Pdot (e.g., PFB) may be greater than 30%, 20%, 10%, or 1%. In some cases, the Pdot may have a quantum yield within the following ranges, 1-10%, 5-15%, 10-20%, 15-25%, 20-30% or greater than 30%. In some cases the Pdot (e.g., PFB) may be mixed with solid substance PSMA and the quantum yield may be greater than 20%, 10%, or 1%. In some cases, the Pdot may have a quantum yield within the following ranges, 1-10%, 5-15%, 10-20%, or greater than 20%. In some cases, the Pdot (e.g., PFB) may be mixed with solid substance PSPEG and the quantum yield may be greater than 30%, 20%, 10%, or 1%. In some cases, the Pdot may have a quantum yield within the following ranges, 1-10%, 5-15%, 10-20%, 15-25%, 20-30%, or greater than 30%.

In some cases, the fluorinated Pdots can simultaneously have all the desirable properties for highly bright Pdots with less nonspecific labeling in biological applications. For example, the fluorinated Pdots can simultaneously have a fluorescence quantum yield higher than that of the non-fluorinated Pdots, but nonspecific labeling less than that of the non-fluorinated Pdots. In some cases, the fluorinated Pdots can simultaneously have a fluorescence quantum yield 2 times higher than that of the non-fluorinated Pdots, but nonspecific labeling 2 times less than that of the non-fluorinated Pdots. In some cases, the fluorinated Pdots can simultaneously have a fluorescence quantum yield 3 times higher than that of the non-fluorinated Pdots, but nonspecific labeling 3 times less than that of the non-fluorinated Pdots. In some cases, the fluorinated Pdots can simultaneously have a fluorescence quantum yield 4 times higher than that of the non-fluorinated Pdots, but nonspecific labeling 4 times less than that of the non-fluorinated Pdots. In some cases, the fluorinated Pdots can simultaneously have a fluorescence quantum yield 5 times higher than that of the non-fluorinated Pdots, but nonspecific labeling 5 times less than that of the non-fluorinated Pdots. In some cases, the fluorinated Pdots can simultaneously have a fluorescence quantum yield more than 5 times higher than that of the non-fluorinated Pdots, but nonspecific labeling more than 5 times less than that of the non-fluorinated Pdots. In some cases, the fluorinated Pdots can simultaneously have a fluorescence quantum yield more than 6 times higher than that of the non-fluorinated Pdots, but nonspecific labeling more than 6 times less than that of the non-fluorinated Pdots. In some cases, the fluorinated Pdots can simultaneously have a fluorescence quantum yield more than 7 times higher than that of the non-fluorinated Pdots, but nonspecific labeling more than 7 times less than that of the non-fluorinated Pdots. In some cases, the fluorinated Pdots can simultaneously have a fluorescence quantum yield more than 8 times higher than that of the non-fluorinated Pdots, but nonspecific labeling more than 8 times less than that of the non-fluorinated Pdots. In some cases, the fluorinated Pdots can simultaneously have a fluorescence quantum yield more than 9 times higher than that of the non-fluorinated Pdots, but nonspecific labeling more than 9 times less than that of the non-fluorinated Pdots. In some cases, the fluorinated Pdots can simultaneously have a fluorescence quantum yield more than 10 times higher than that of the non-fluorinated Pdots, but nonspecific labeling more than 10 times less than that of the non-fluorinated Pdots. In some cases, the fluorinated Pdots can simultaneously have a fluorescence quantum yield more than 15 times higher than that of the non-fluorinated Pdots, but nonspecific labeling more than 15 times less than that of the non-fluorinated Pdots. In some cases, the fluorinated Pdots can simultaneously have a fluorescence quantum yield more than 20 times higher than that of the non-fluorinated Pdots, but nonspecific labeling more than 20 times less than that of the non-fluorinated Pdots.

Absorption Cross Section

In some cases, the absorption cross section of fluorinated Pdots is affected by the fluorine content in the conjugated polymers. In a preferable case, the fluorine content is less than 50% by mass so that the fluorinated Pdots so that can be prepared by a nanoprecipitation method involving mixing the polymer in THF solution with water. The fluorine content can be varied from 0 to 50% by mass to increase the absorption cross section of the fluorinated Pdots to make highly bright Pdots. In some cases, the fluorinated Pdots has an absorption cross section that equal to or is higher than that of the non-fluorinated Pdots of similar size. In some cases, the fluorinated Pdots has an absorption cross section that is 1.5 times higher than that of the non-fluorinated Pdots of similar size. In some cases, the fluorinated Pdots has an absorption cross section that is 2 times higher than that of the non-fluorinated Pdots of similar size. In some cases, the fluorinated Pdots has an absorption cross section that is 3 times higher than that of the non-fluorinated Pdots of similar size. In some cases, the fluorinated Pdots has an absorption cross section that is 4 times higher than that of the non-fluorinated Pdots of similar size. In some cases, the fluorinated Pdots has an absorption cross section that is 5 times higher than that of the non-fluorinated Pdots of similar size. In some cases, the fluorinated Pdots has an absorption cross section that is more than 5 times higher than that of the non-fluorinated Pdots of similar size. In some cases, the fluorinated Pdots has an absorption cross section that is 6 times higher than that of the non-fluorinated Pdots of similar size. In some cases, the fluorinated Pdots has an absorption cross section that is more than 6 times higher than that of the non-fluorinated Pdots of similar size. In some cases, the fluorinated Pdots has an absorption cross section that is 7 times higher than that of the non-fluorinated Pdots of similar size. In some cases, the fluorinated Pdots has an absorption cross section that is more than 7 times higher than that of the non-fluorinated Pdots of similar size. In some cases, the fluorinated Pdots has an absorption cross section that is 8 times higher than that of the non-fluorinated Pdots of similar size. In some cases, the fluorinated Pdots has an absorption cross section that is more than 8 times higher than that of the non-fluorinated Pdots of similar size. In some cases, the fluorinated Pdots has an absorption cross section that is 9 times higher than that of the non-fluorinated Pdots of similar size. In some cases, the fluorinated Pdots has an absorption cross section that is more than 9 times higher than that of the non-fluorinated Pdots of similar size. In some cases, the fluorinated Pdots has an absorption cross section that is 10 times higher than that of the non-fluorinated Pdots of similar size. In some cases, the fluorinated Pdots has an absorption cross section that is more than 10 times higher than that of the non-fluorinated Pdots of similar size. In some cases, the fluorinated Pdots has an absorption cross section that is 15 times higher than that of the non-fluorinated Pdots of similar size. In some cases, the fluorinated Pdots has an absorption cross section that is more than 15 times higher than that of the non-fluorinated Pdots of similar size. In some cases, the fluorinated Pdots has an absorption cross section that is 20 times higher than that of the non-fluorinated Pdots of similar size. In some cases, the fluorinated Pdots has an absorption cross section that is more than 20 times higher than that of the non-fluorinated Pdots of similar size.

Absorption Wavelength

Pdots may have a wide range of absorption wavelengths. In some cases, the Pdot may not have a fluorine substitution. In some cases, Pdots without any substitutions may have an absorption wavelength less than or equal to about 1000 nm, about 900 nm, about 800 nm, about 750 nm, about 700 nm, about 650 nm, about 600 nm, about 550 nm, about 500 nm, 450 nm, about 400 nm, about 350 nm, about 300 nm, about 250 nm, about 200 nm, about 150 nm, or about 100 nm. In some cases, the Pdot (e.g., PFDPBT) may be bare in aqueous solution and the absorption wavelength may be less than about 800 nm, about 750 nm, about 700 nm, about 650 nm, about 600 nm, about 550 nm, about 500 nm, 450 nm, about 400 nm, about 350 nm, about 300 nm, about 250 nm, about 200 nm, about 150 nm, or about 100 nm. In some cases, the Pdot may have an absorption wavelength within the following ranges, 100-300 nm, 200-400 nm, 300 nm-500 nm, 400 nm-600 nm, 500-700 nm, 600 nm-800 nm or 800 nm-1000 nm. In some cases, the absorption wavelength may be 405 nm, 450 nm, 488, 532 nm, 633 nm or 700 nm.

In some cases, the Pdot (e.g., PFB) may be bare in aqueous solution and the absorption wavelength may be about 1000 nm, about 900 nm, about 800 nm, about 750 nm, about 700 nm, about 650 nm, about 600 nm, about 550 nm, about 500 nm, 450 nm, about 400 nm, about 350 nm, about 300 nm, about 250 nm, about 200 nm, about 150 nm, or about 100 nm. In some cases, the Pdot may have an absorption wavelength within the following ranges, 100-300 nm, 200-400 nm, 300 nm-500 nm, 400 nm-600 nm, 500-700 nm, 600 nm-800 nm or 800 nm-1000 nm. In some cases, the absorption wavelength may be 405 nm, 450 nm, 488, 532 nm, 633 nm or 700 nm. In some cases, the Pdot may be mixed with a solid substance. In some cases, the solid substance may affect the absorption wavelength of the Pdot. In some cases, the Pdot (e.g., PFB) may be mixed with PSMA and the absorption wavelength may be about 800 nm, about 750 nm, about 700 nm, about 650 nm, about 600 nm, about 550 nm, about 500 nm, 450 nm, about 400 nm, about 350 nm, about 300 nm, about 250 nm, about 200 nm, about 150 nm, or about 100 nm. In some cases, the Pdot may have an absorption wavelength within the following ranges, 100-300 nm, 200-400 nm, 300 nm-500 nm, 400 nm-600 nm, 500-700 nm or 600 nm-800 nm. In some cases, the absorption wavelength may be 405 nm, 450 nm, 488, 532 nm, 633 nm or 700 nm. In some cases, the Pdot (e.g., PFB) may be mixed with PSPEG and the absorption wavelength may be about 800 nm, about 750 nm, about 700 nm, about 650 nm, about 600 nm, about 550 nm, about 500 nm, 450 nm, about 400 nm, about 350 nm, about 300 nm, about 250 nm, about 200 nm, about 150 nm, or about 100 nm. In some cases, the Pdot may have an absorption wavelength within the following ranges, 100-300 nm, 200-400 nm, 300 nm-500 nm, 400 nm-600 nm, 500-700 nm or 600 nm-800 nm. In some cases, the absorption wavelength may be 405 nm, 450 nm, 488, 532 nm, 633 nm or 700 nm.

In other cases, the number of substitutions to the Pdot backbone can affect the absorption wavelength of the Pdot. Pdots with fluorine atom substitutions may have an absorption wavelength less than or equal to about 1000 nm, about 900 nm, about 800 nm, about 750 nm, about 700 nm, about 650 nm, about 600 nm, about 550 nm, about 500 nm, 450 nm, about 400 nm, about 350 nm, about 300 nm, about 250 nm, about 200 nm, about 150 nm, or about 100 nm. In some cases, the Pdot (e.g., PFDPFBT) may have a fluorine substitution and is bare in aqueous solution and the absorption wavelength of about 1000 nm, about 900 nm, about 800 nm, about 750 nm, about 700 nm, about 650 nm, about 600 nm, about 550 nm, about 500 nm, 450 nm, about 400 nm, about 350 nm, about 300 nm, about 250 nm, about 200 nm, about 150 nm, or about 100 nm. In some cases, the Pdot may have an absorption wavelength within the following ranges, 100-300 nm, 200-400 nm, 300 nm-500 nm, 400 nm-600 nm, 500-700 nm, 600 nm-800 nm or 800 nm-1000 nm. In some cases, the absorption wavelength may be 405 nm, 450 nm, 488, 532 nm, 633 nm or 700 nm. In some cases, the Pdot may be mixed with a solid substance. In some cases, the solid substance may affect the absorption wavelength of the Pdot. In some cases, the Pdot (e.g., PFDPDFBT) may be mixed with PSPEG and the absorption wavelength may be about 1000 nm, 900 nm, 800 nm, about 750 nm, about 700 nm, about 650 nm, about 600 nm, about 550 nm, about 500 nm, 450 nm, about 400 nm, about 350 nm, about 300 nm, about 250 nm, about 200 nm, about 150 nm, or about 100 nm. In some cases, the Pdot may have an absorption wavelength within the following ranges, 100-300 nm, 200-400 nm, 300 nm-500 nm, 400 nm-600 nm, 500-700 nm or 600 nm-800 nm. In some cases, the absorption wavelength may be 405 nm, 450 nm, 488, 532 nm, 633 nm or 700 nm. In some cases, the Pdot (e.g., PFDPDFBT) may be mixed with PSMA and the absorption wavelength may be about 1000 nm, 900 nm, 800 nm, about 750 nm, about 700 nm, about 650 nm, about 600 nm, about 550 nm, about 500 nm, 450 nm, about 400 nm, about 350 nm, about 300 nm, about 250 nm, about 200 nm, about 150 nm, or about 100 nm. In some cases, the Pdot may have an absorption wavelength within the following ranges, 100-300 nm, 200-400 nm, 300 nm-500 nm, 400 nm-600 nm, 500-700 nm or 600 nm-800 nm. In some cases, the absorption wavelength may be 405 nm, 450 nm, 488, 532 nm, 633 nm or 700 nm. In some cases, the Pdot (e.g., PFDPDFBT) may be bare in aqueous solution and the absorption wavelength may be 800 nm, about 750 nm, about 700 nm, about 650 nm, about 600 nm, about 550 nm, about 500 nm, 450 nm, about 400 nm, about 350 nm, about 300 nm, about 250 nm, about 200 nm, about 150 nm, or about 100 nm. In some cases, the Pdot may have an absorption wavelength within the following ranges, 100-300 nm, 200-400 nm, 300 nm-500 nm, 400 nm-600 nm, 500-700 nm or 600 nm-800 nm. In some cases, the absorption wavelength may be 405 nm, 450 nm, 488, 532 nm, 633 nm or 700 nm.

In some cases, the Pdot (e.g., PFDFB) may be mixed with PSMA and the absorption wavelength may be about 800 nm, about 750 nm, about 700 nm, about 650 nm, about 600 nm, about 550 nm, about 500 nm, 450 nm, about 400 nm, about 350 nm, about 300 nm, about 250 nm, about 200 nm, about 150 nm, or about 100 nm. In some cases, the Pdot may have an absorption wavelength within the following ranges, 100-300 nm, 200-400 nm, 300 nm-500 nm, 400 nm-600 nm, 500-700 nm or 600 nm-800 nm. In some cases, the absorption wavelength may be 405 nm, 450 nm, 488, 532 nm, 633 nm or 700 nm. In some cases, the Pdot (e.g., PFDFB) may be mixed with PSPEG and the absorption wavelength may be about 800 nm, about 750 nm, about 700 nm, about 650 nm, about 600 nm, about 550 nm, about 500 nm, 450 nm, about 400 nm, about 350 nm, about 300 nm, about 250 nm, about 200 nm, about 150 nm, or about 100 nm. In some cases, the Pdot may have an absorption wavelength within the following ranges, 100-300 nm, 200-400 nm, 300 nm-500 nm, 400 nm-600 nm, 500-700 nm or 600 nm-800 nm. In some cases, the absorption wavelength may be 405 nm, 450 nm, 488, 532 nm, 633 nm or 700 nm. In some cases, the Pdot (e.g., PFDFB) may be bare in aqueous solution and the absorption wavelength may be about 800 nm, about 750 nm, about 700 nm, about 650 nm, about 600 nm, about 550 nm, about 500 nm, 450 nm, about 400 nm, about 350 nm, about 300 nm, about 250 nm, about 200 nm, about 150 nm, or about 100 nm. In some cases, the Pdot may have an absorption wavelength within the following ranges, 100-300 nm, 200-400 nm, 300 nm-500 nm, 400 nm-600 nm, 500-700 nm or 600 nm-800 nm. In some cases, the absorption wavelength may be 405 nm, 450 nm, 488, 532 nm, 633 nm or 700 nm.

Photoluminescence Wavelength

In some cases, the photoluminescence wavelength of the Pdot may be a function of the chemical structure. Pdots without a fluorine substitution may have a photoluminescence wavelength that may be less than or equal to about 1000 nm, 900 nm, 800 nm, about 750 nm, about 700 nm, about 650 nm, about 600 nm, about 550 nm, about 500 nm, 450 nm, about 400 nm, about 350 nm, about 300 nm, about 250 nm, about 200 nm, about 150 nm, or about 100 nm. In some cases, the Pdot (e.g., PFDPBT) without a fluorine substitution may be bare in aqueous solution and the photoluminescence wavelength may be less than or equal to about 1000 nm, 900 nm, 800 nm, about 750 nm, about 700 nm, about 650 nm, about 600 nm, about 550 nm, about 500 nm, 450 nm, about 400 nm, about 350 nm, about 300 nm, about 250 nm, about 200 nm, about 150 nm, or about 100 nm. In some cases, the Pdot may have a photoluminescence wavelength within the following ranges, 100-300 nm, 200-400 nm, 300 nm-500 nm, 400 nm-600 nm, 500-700 nm or 600 nm-800 nm.

In some cases, the Pdot (e.g., PFB) may be bare in aqueous solution and the photoluminescence wavelength may be 1000 nm, 900 nm, 800 nm, about 750 nm, about 700 nm, about 650 nm, about 600 nm, about 550 nm, about 500 nm, 450 nm, about 400 nm, about 350 nm, about 300 nm, about 250 nm, about 200 nm, about 150 nm, or about 100 nm. In some cases, the Pdot may have a photoluminescence wavelength within the following ranges, 100-300 nm, 200-400 nm, 300 nm-500 nm, 400 nm-600 nm, 500-700 nm, 600 nm-800 nm, or 800 nm-1000 nm. In some cases, the Pdot is mixed with a solid structure. In some cases, the solid structure may affect the photoluminescence wavelength of the Pdot. In some cases, the Pdot (e.g., PFB) may be mixed with PSMA and the photoluminescence wavelength may be less than or equal to about 1000 nm, 900 nm, 800 nm, about 750 nm, about 700 nm, about 650 nm, about 600 nm, about 550 nm, about 500 nm, 450 nm, about 400 nm, about 350 nm, about 300 nm, about 250 nm, about 200 nm, about 150 nm, or about 100 nm. In some cases, the Pdot may have a photoluminescence wavelength within the following ranges, 100-300 nm, 200-400 nm, 300 nm-500 nm, 400 nm-600 nm, 500-700 nm, 600 nm-800 nm or 800 nm-1000 nm. In some cases, the Pdot (e.g., PFB) may be mixed with PSPEG and the photoluminescence wavelength may be less than or equal to about 1000 nm, 900 nm, 800 nm, about 750 nm, about 700 nm, about 650 nm, about 600 nm, about 550 nm, about 500 nm, 450 nm, about 400 nm, about 350 nm, about 300 nm, about 250 nm, about 200 nm, about 150 nm, or about 100 nm. In some cases, the Pdot may have a photoluminescence wavelength within the following ranges, 100-300 nm, 200-400 nm, 300 nm-500 nm, 400 nm-600 nm, 500-700 nm, 600 nm-800 nm or 800 nm-1000 nm.

In some cases, the number of substitutions to the Pdot backbone can affect the photoluminescence wavelength of the Pdot. Pdots with fluorine atom substitutions may have a photoluminescence wavelength less than or equal to about 1000 nm, 900 nm, 800 nm, about 750 nm, about 700 nm, about 650 nm, about 600 nm, about 550 nm, about 500 nm, 450 nm, about 400 nm, about 350 nm, about 300 nm, about 250 nm, about 200 nm, about 150 nm, or about 100 nm. In some cases, the Pdot (e.g., PFDPFBT) with a fluorine substitution may be bare in aqueous solution and the photoluminescence wavelength may be less than or equal to 1000 nm, 900 nm, about 800 nm, about 750 nm, about 700 nm, about 650 nm, about 600 nm, about 550 nm, about 500 nm, 450 nm, about 400 nm, about 350 nm, about 300 nm, about 250 nm, about 200 nm, about 150 nm, or about 100 nm. In some cases, the Pdot may have a photoluminescence wavelength within the following ranges, 100-300 nm, 200-400 nm, 300 nm-500 nm, 400 nm-600 nm, 500-700 nm, 600 nm-800 nm or 800 nm-1000 nm. In some cases, the Pdot (e.g., PFDFB) may be bare in aqueous solution and the photoluminescence wavelength may be 1000 nm, 900 nm, 800 nm, about 750 nm, about 700 nm, about 650 nm, about 600 nm, about 550 nm, about 500 nm, 450 nm, about 400 nm, about 350 nm, about 300 nm, about 250 nm, about 200 nm, about 150 nm, or about 100 nm. In some cases, the Pdot may have a photoluminescence wavelength within the following ranges, 100-300 nm, 200-400 nm, 300 nm-500 nm, 400 nm-600 nm, 500-700 nm or 600 nm-800 nm.

In some cases, the Pdot is mixed with a solid structure. In some cases, the solid structure may affect the photoluminescence wavelength of the Pdot. In some cases, the Pdot (e.g., PFDPDFBT) may be mixed with PSPEG and the photoluminescence wavelength may be less than or equal to about 1000 nm, 900 nm, 800 nm, about 750 nm, about 700 nm, about 650 nm, about 600 nm, about 550 nm, about 500 nm, 450 nm, about 400 nm, about 350 nm, about 300 nm, about 250 nm, about 200 nm, about 150 nm, or about 100 nm. In some cases, the Pdot may have a photoluminescence wavelength within the following ranges, 100-300 nm, 200-400 nm, 300 nm-500 nm, 400 nm-600 nm, 500-700 nm, 600 nm-800 nm or 800 nm-1000 nm. In some cases, the Pdot (e.g., PFDPDFBT) may be mixed with PSMA and the photoluminescence wavelength may be less than or equal to about 1000 nm, 900 nm, 800 nm, about 750 nm, about 700 nm, about 650 nm, about 600 nm, about 550 nm, about 500 nm, 450 nm, about 400 nm, about 350 nm, about 300 nm, about 250 nm, about 200 nm, about 150 nm, or about 100 nm. In some cases, the Pdot may have a photoluminescence wavelength within the following ranges, 100-300 nm, 200-400 nm, 300 nm-500 nm, 400 nm-600 nm, 500-700 nm and 600 nm-800 nm or 800 nm-1000 nm. In some cases, the Pdot (e.g., PFDFB) may be mixed with PSMA and the photoluminescence wavelength may be less than or equal to about 1000 nm, 900 nm, 800 nm, about 750 nm, about 700 nm, about 650 nm, about 600 nm, about 550 nm, about 500 nm, 450 nm, about 400 nm, about 350 nm, about 300 nm, about 250 nm, about 200 nm, about 150 nm, or about 100 nm. In some cases, the Pdot may have a photoluminescence wavelength within the following ranges, 100-300 nm, 200-400 nm, 300 nm-500 nm, 400 nm-600 nm, 500-700 nm, 600 nm-800 nm or 800 nm-1000 nm. In some cases, the Pdot (e.g., PFDFB) may be mixed with PSPEG and the photoluminescence wavelength 1000 nm, 900 nm, 800 nm, about 750 nm, about 700 nm, about 650 nm, about 600 nm, about 550 nm, about 500 nm, 450 nm, about 400 nm, about 350 nm, about 300 nm, about 250 nm, about 200 nm, about 150 nm, or about 100 nm. In some cases, the Pdot may have a photoluminescence wavelength within the following ranges, 100-300 nm, 200-400 nm, 300 nm-500 nm, 400 nm-600 nm, 500-700 nm, 600 nm-800 nm or 800 nm-1000 nm.

Pdots may be blended, e.g., with a polymer. In some cases, the polymer may be an amphiphilic polymer.

Methods for Labeling Analytes in a Sample

This disclosure provides methods for using Pdots to detect analytes within a sample such as a mixed sample. In some cases, the sample may be a fluid sample. The fluid sample may be a biological fluid sample, for example a blood sample, plasma sample, saliva sample, urine sample, lymph sample, or spinal fluid sample. In some cases, the sample may be an environmental fluid sample, for example from a lake, river, ocean, pond, stream, spring, marsh, or reservoir. In other cases, the sample may be a water sample, for example from a desalinization plant, water treatment plant, reservoir, spring, stream, glacial water flow, water tower, or other water source that may be contemplated as a source of potable water.

Figure 17:
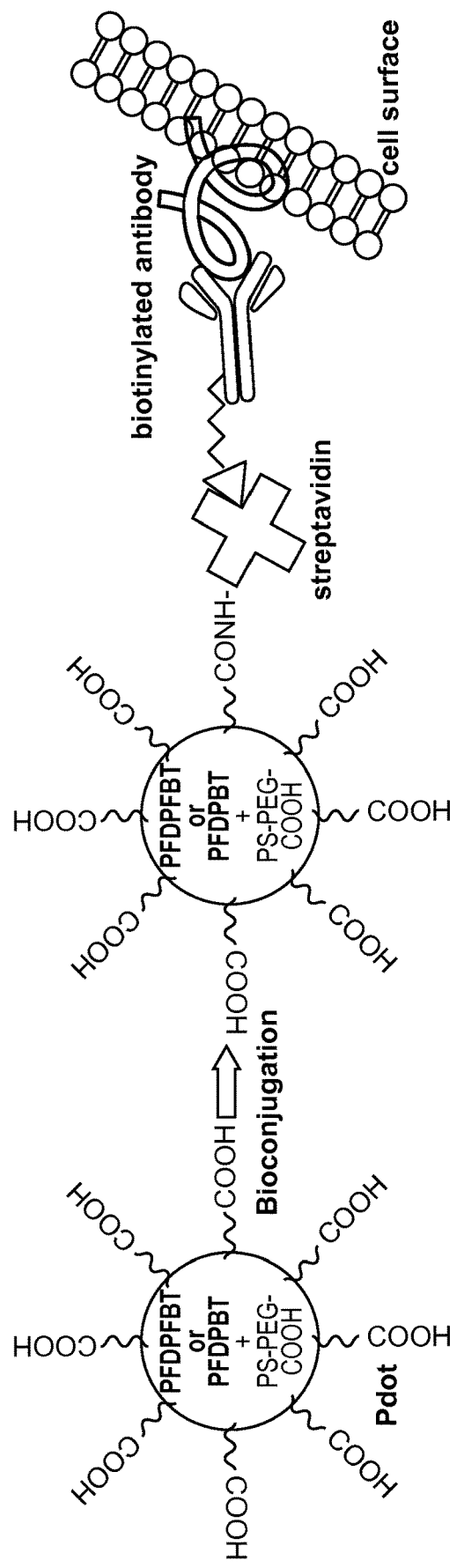
FIG. 17. A schematic depicting PFDPFBT/PSPEGCOOH and PFDPBT/PSPEGCOOH Pdots and their bioconjugated probes for cellular imaging.

In some cases, a molecule expressed by an analyte such as a cell may be detected with the Pdots provided herein. For example, cells may be contacted with an agent (e.g., antibody) that recognizes a molecule (e.g., cell surface marker, intracellular marker, etc.). In some cases provided herein, the agent is modified so that it can bind to or connect to a binding partner that is connected to a Pdot. For example, the agent may be modified by conjugating the agent to biotin or streptavidin. In some specific examples, the agent is conjugated to biotin so that the agent is capable of recognizing a streptavidin molecule that is conjugated to a Pdot. FIG. 17 is an illustration that depicts Pdots that are linked to antibodies via a biotin-avidin linkage. In this illustration, the PFDPFBT/PSPEGCOOH and PFDPBT/PSPEGCOOH Pdots are conjugated to streptavidin. These Pdots are bound to biotinylated antibodies that recognize a specific cellular marker. (See FIG. 17). Such Pdots are useful in a wide variety of applications, including cellular imaging studies.

The methods provided herein may include incubation periods. For example, the Pdots may be incubated with the agents (such as antibodies); the agents (including agents conjugated to Pdots) may be incubated with the analytes (e.g., cells). The incubation period may last for a length of time that is less than or equal to 100 hours, 75 hours, 60 hours, 50 hours, 24 hours, 20 hours, 15 hours, 10 hours, 5 hours, 3 hours, 2 hours, or 1 hour. In some cases, the incubation period may be greater than 5 minutes, 10 minutes, 30 minutes, 1 hour, 2 hours, 5 hours, 10 hours, 24 hours, 30 hours, 50 hours, 60 hours, 75 hours or 100 hours.

The analyte in the fluid sample may be a cell, protein, protein complex, nucleic acid, nucleoprotein complex, carbohydrate, metabolite, catabolite, and the like. In some cases, the analyte may be a cell. Non-limiting examples of cells include: mammalian cells, human cells, non-human mammalian cells, eukaryotic cells, prokaryotic cells, animal cells, insect cells, bacteria cells, microbial cells, fungal cells, amphibian cells and fish cells. The cells can originate from a variety of tissues including but not limited to: neural crest tissue, endodermal tissue, ectodermal tissue, mesodermal tissue, and mesenchymal tissue. Cell types may include but are not limited to: breast cells, brain cells, neural cells, pancreatic cells, liver cells, gall bladder cells, gastrointestinal cells, stomach cells, kidney cells, cells of the reproductive system, heart cells, skin cells, colon cells, urethral cells, endodermal cells, muscle cells, fibroblasts, adipocytes, tumor cells, cancer cells, virally-infected cells, bacterial infected cells, stem cells, dividing cells, apoptotic cells, necrotic cells, blood cells, white blood cells, and stromal cells.

The sample may be contacted with an agent suitable for labeling the analyte. In some cases, the agent may be an antibody, an antibody fragment, a peptide, an Fab fragment, an Fc fragment, a light chain, a heavy chain, an immunoglobin, or an immunoglobin fragment. In some cases, the agent is a peptide or a small molecule. In some cases, the agent is modified. The modification to the agent may include a chemical modification, an enzymatic modification, linkage of a hydrophilic functional group, a hydrophobic functional group and/or a reactive moiety.

In some cases, the cell may express an antigen, for example, that may be detected by the agent. For example, an agent may be an antibody. The antibody may be EpCAM which is expressed on some cancerous cells, including MCF-7 cells. Other examples of antibodies that may be conjugated to a Pdot include but are not limited to the pan-cytokeratin antibody A45B/B3, AE1/AE3, or CAM5.2 (pan-cytokeratin antibodies that recognize Cytokeratin 8 (CK8), Cytokeratin 18 (CK18), or Cytokeratin 19 (CK19) and ones against: breast cancer antigen NY-BR-1 (also known as B726P, ANKRD30A, Ankyrin repeat domain 30A); B305D isoform A or C (B305D-A ro B305D-C; also known as antigen B305D); Hermes antigen (also known as Antigen CD44, PGP1); E-cadherin (also known as Uvomorulin, Cadherin-1, CDH1); Carcino-embryonic antigen (CEA; also known as CEACAM5 or Carcino-embryonic antigen-related cell adhesion molecule 5); β-Human chorionic gonadotophin (β-HCG; also known as CGB, Chronic gonadotrophin, β polypeptide); Cathepsin-D (also known as CTSD); Neuropeptide Y receptor Y3 (also known as NPY3R; Lipopolysaccharide-associated protein3, LAP3, Fusion; Chemokine (CXC motif, receptor 4); CXCR4); Oncogene ERBB1 (also known as c-erbB-1, Epidermal growth factor receptor, EGFR); Her-2 Neu (also known as c-erbB-2 or ERBB2); GABA receptor A, pi (π) polypeptide (also known as GABARAP, GABA-A receptor, pi (π) polypeptide (GABA A(π), γ-Aminobutyric acid type A receptor pi (π) subunit), or GABRP); ppGalNac-T(6) (also known as β-1-4-N-acetyl-galactosaminyl-transferase 6, GalNActransferase 6, GalNAcT6, UDP-N-acetyl-d-galactosamine:polypeptide N-acetylgalactosaminyltransferase 6, or GALNT6); CK7 (also known as Cytokeratin 7, Sarcolectin, SCL, Keratin 7, or KRT7); CK8 (also known as Cytokeratin 8, Keratin 8, or KRT8); CK18 (also known as Cytokeratin 18, Keratin 18, or KRT18); CK19 (also known as Cytokeratin 19, Keratin 19, or KRT19); CK20 (also known as Cytokeratin 20, Keratin 20, or KRT20); Mage (also known as Melanoma antigen family A subtypes or MAGE-A subtypes); Mage3 (also known as Melanoma antigen family A 3, or MAGA3); Hepatocyte growth factor receptor (also known as HGFR, Renal cell carninoma papillary 2, RCCP2, Protooncogene met, or MET); Mucin-1 (also known as MUC1, Carcinoma Antigen 15.3, (CA15.3), Carcinoma Antigen 27.29 (CA 27.29); CD227 antigen, Episialin, Epithelial Membrane Antigen (EMA), Polymorphic Epithelial Mucin (PEM), Peanut-reactive urinary mucin (PUM), Tumor-associated glycoprotein 12 (TAG12)); Gross Cystic Disease Fluid Protein (also known as GCDFP-15, Prolactin-induced protein, PIP); Urokinase receptor (also known as uPR, CD87 antigen, Plasminogen activator receptor urokinase-type, PLAUR); PTHrP (parathyroid hormone-related proteins; also known as PTHLH); BS106 (also known as B511S, small breast epithelial mucin, or SBEM); Prostatein-like Lipophilin B (LPB, LPHB; also known as Antigen BU101, Secretoglobin family 1-D member 2, SCGB1-D2); Mammaglobin 2 (MGB2; also known as Mammaglobin B, MGBB, Lacryglobin (LGB) Lipophilin C (LPC, LPHC), Secretoglobin family 2A member 1, or SCGB2A1); Mammaglobin (MGB; also known as Mammaglobin 1, MGB1, Mammaglobin A, MGBA, Secretoglobin family 2A member 2, or SCGB2A2); Mammary serine protease inhibitor (Maspin, also known as Serine (or cystein) proteinase inhibitor clade B (ovalbumin) member 5, or SERPINBS); Prostate epithelium-specific Ets transcription factor (PDEF; also known as Sterile alpha motif pointed domain-containing ets transcription factor, or SPDEF); Tumor-associated calcium signal transducer 1 (also known as Colorectal carcinoma antigen CO17-1A, Epithelial Glycoprotein 2 (EGP2), Epithelial glycoprotein 40 kDa (EGP40), Epithelial Cell Adhesion Molecule (Ep-CAM), Epithelial-specific antigen (ESA), Gastrointestinal tumor-associated antigen 733-2 (GA733-2), KS1/4 antigen, Membrane component of chromosome 4 surface marker 1 (M4S1), MK-1 antigen, MIC18 antigen, TROP-1 antigen, or TACSTD1); Telomerase reverse transcriptase (also known as Telomerase catalytic subunit, or TERT); Trefoil Factor 1 (also known as Breast Cancer Estrogen-Inducible Sequence, BCEI, Gastrointestinal Trefoil Protein, GTF, pS2 protein, or TFF1); folate; or Trefoil Factor 3 (also known as Intestinal Trefoil Factor, ITF, p1.B; or TFF3).

In some cases, a sample containing analytes may be prepared for labeling. At any stage of a method provided herein, the analytes (e.g., cells) may be incubated with a blocking buffer to prevent or reduce non-specific binding of the agent. In some cases, non-specific binding may be measured, e.g., by percentage, fold, change, of non-specific binding, relative to another compound. For example, the fold of non-specific binding may be less than 1 fold, 2 fold, 3 fold, 4 fold, 5 fold, 6 fold, 7 fold, 8 fold, 9 fold or 10 fold.

At any stage of a method provided herein, the analytes (e.g., cells) may be washed with a suitable buffer solution. The cells may be concentrated by any method known in the art, including but not limited to centrifugation or filtration. In some cases, the analytes (e.g., cells) are not concentrated as part of a method provided herein. In some cases, the method may include fixing the cells with a fixative. In other cases, the method may not include fixing the cells with a fixative. In some cases, the method may include permeablizing the cells with an agent suitable for permeabilization. In other cases, preparation of the cells may not include permeablizing the cells with an agent suitable for permeabilization.

Methods of Detection Analytes in a Sample

The disclosure provides for methods that may be used to detect analytes in a sample, particularly to detect a Pdot provided herein. The analytes may be labeled with Pdots; or, in some cases, the analytes may be labeled with a combination of Pdots and other labeling agents such as fluorophores. In some cases, labeled analytes from a sample may be analyzed for the presence of a Pdot. In some cases, a flow cytometer may be used to detect Pdots (e.g., FACS Canto II). In some cases, the flow cytometer may be equipped with a laser (e.g., 405 nm). In some cases, the Pdots may be detected using a laser (e.g., 405 nm) and detection channels for fluorescence emission with filters (e.g., 502 nm longpass and a 510/50 nm band-pass filter). In some cases, the scattered light and fluorescence emission may be detected by photomultiplier tube arrays. In some cases, the data acquired from flow cytometry experiments may be analyzed using software (e.g., FlowJo).

In some cases, fluorescence microscopy may be used to detect the Pdots. For example, a fluorescent microscope equipped with a camera may be used to image cells. The microscope may be a confocal microscope (e.g., Zeiss LSM 510). The Pdots may be excited by laser (e.g., a 405-nm diode laser or a 488-nm argon laser). In some cases, cells may be imaged such as by using glass-bottomed culture dishes.

In some cases, an analyte may be contacted with a plurality of labels. For example, the analyte may be contacted with a plurality of different Pdots, or with a combination of Pdot(s) and another labeling agent, such as a fluorophore. In some cases, an analyte may be contacted with a plurality of agents. The plurality of agents may be, for example: (a) a plurality of different agents (e.g., different antibodies) conjugated to the same Pdot; (b) a plurality of different agents (e.g., different antibodies) conjugated to different Pdots; (c) a combination of: (i) agents conjugated to one or more Pdots; and (ii) agents conjugated to one or more different labels (e.g., fluorophores).

In some examples, an analytes such as a cell is contacted with Pdots as well as with a second label that is specific for a cellular feature such as the nucleus, cytoplasm, mitochondrion, membrane, or other feature. For example, cells may be labeled with (a) Pdots that are conjugated to a specific agent (e.g., antibody) and (b) a nuclear stain such as Hoechst 34580. The cells may be imaged such as with a fluorescence microscope in order to detect the Pdots and the second label.

Synthesis of Intermediate Compounds

Figure 2:
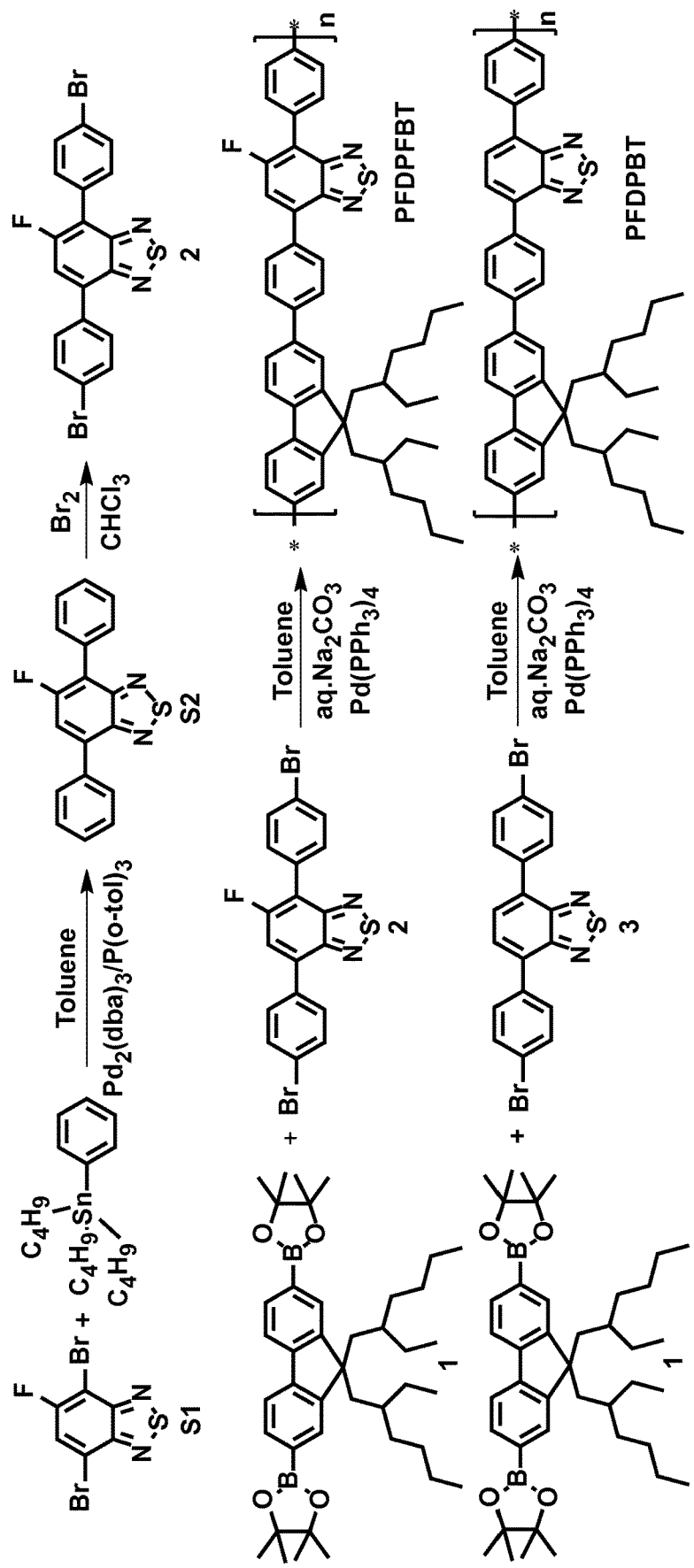
FIG. 2. The synthetic route of monomers and polymers.

The method provides for the synthesis of 4,4-diphenyl-5-fluoro-[2,1,3]benzothiadiazole (DPFBT) (molecule S2 in FIG. 2). Solutions of 4,7-dibromo-5-fluoro-[2,1,3]benzothiadiazole (DiBrDPFBT) (molecule S1 in FIG. 2) (e.g., 0.35 g, 1.1 mmol) and tributylstannyl benzene (e.g., 1.0 g, 2.7 mmol) in toluene (e.g., 5 mL) can be added to $Pd_2(dba)_3$ (50 mg) and $P(o-tol)_3$ (e.g., 100 mg). The resulting mixture can then be degassed twice and be heated to achieve reflux overnight (e.g., 8-18 hours). After cooling (e.g., to room temperature), the organic solvent is removed. The crude product can then be purified in a silica column (e.g., 0.4 g, 96%).

The method provides for the synthesis of 4-di(4'-bromophenyl)-5-fluoro-[2,1,3]benzothiadiazole (molecule 2 in FIG. 2). To a solution of compound 4,4-diphenyl-5-fluoro-[2,1,3]benzothiadiazole (molecule S2 in FIG. 2) (e.g., 0.4 g, 1.3 mmol) in $CHCl_3$ (e.g., 20 mL), bromine (e.g., 1.2 mL) a small amount of iodine (e.g., 50 mg) can be added (e.g., in the dark). The solution is stirred (e.g., at room temperature for 24 hours) before adding saturated $Na_2CO_3$ aqueous solution. The precipitate may be filtered and washed with methanol and hexane. The precipitate may be further dried (e.g., overnight under vacuum) (e.g., 0.5 g, 83%).

Figure 3:
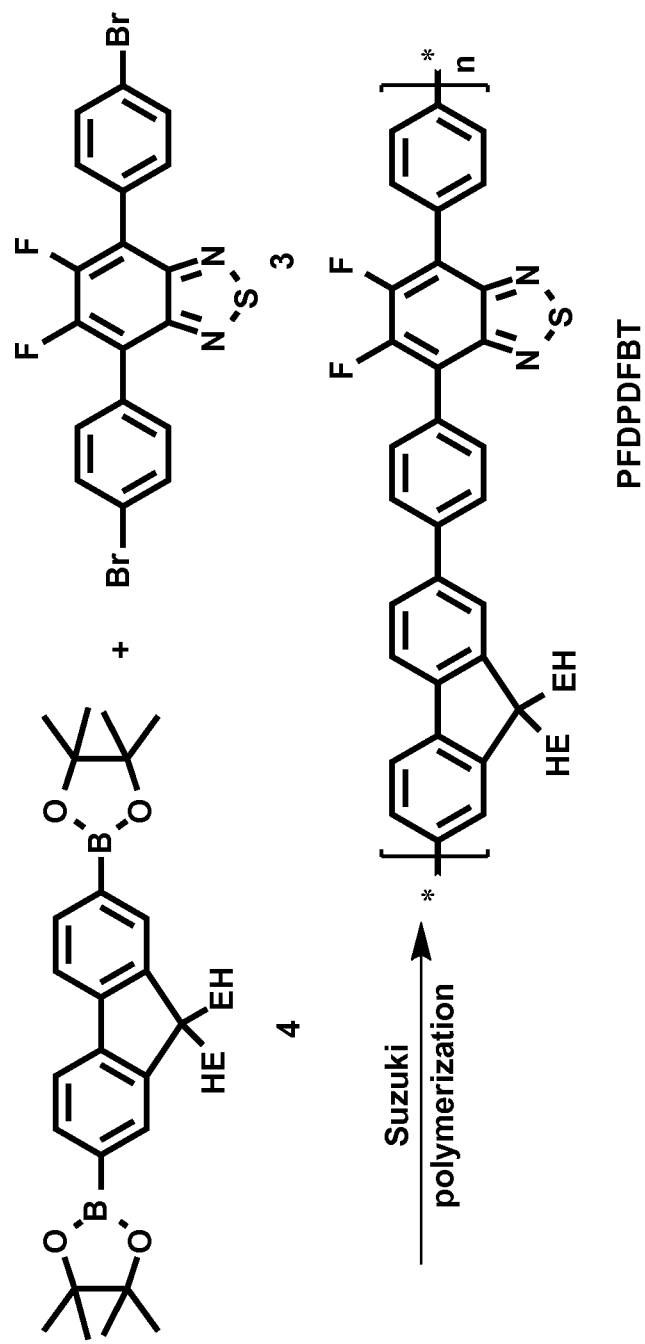
FIG. 3. The synthesis of fluorinated polymer PFDPDFBT.

The method provides for the synthesis of 4,4-di(4'-bromophenyl)-5,6-difluoro-[2,1,3]benzothiadiazole (molecule 3 FIG. 3). To a solution of 4,4-diphenyl-5-fluoro-[2,1,3]benzothiadiazole (molecule S2 FIG. 2) (e.g., 0.6 g, 1.85 mmol) in $CHCl_3$ (e.g., 15 mL), bromine (e.g., 2.0 mL) and a small amount of iodine (e.g., 50 mg) can be added (e.g., in the dark). The solution can be heated (e.g., to 60° C.) overnight (e.g., 8-18 hours) before the addition of saturated $Na_2CO_3$ aqueous solution. The precipitate can filtered (e.g., silica) and washed (e.g., methanol and hexane), and dried overnight (e.g., 8-18 hours) under vacuum.

Synthesis of single fluorinated polymer (poly[(9,9-di(2-ethylhexyl)fluorenyl-2,7-diyl)-alt-4,4'-diphenyl-5-fluoro-1,4-benzo-(2,1,3)-thiadiazole]) PFDPFBT This disclosure provides for the synthesis of the fluorinated semiconducting Pdot PFDPFBT (FIG. 2). FIG. 2 depicts the synthesis reaction to generate PFDPFBT. A Suzuki polymerization between molecules 1 and 2, of FIG. 2, with the $Pd(PPh_3)$ catalyst yields the fluorinated PFDPFBT (FIG. 2). Non-fluorinated PFDPBT is synthesized under the same conditions.

In some cases, the method provides for the synthesis of PFDPFBT (FIG. 2). Compound 2,7-Bis(4,4,5,5-tetramethyl-1,3,2-dioxaborolan-2-yl)-9,9-di(2-ethylhexyl) fluorene (molecule 1 in FIG. 2) (e.g., 120 mg, 0.19 mmol) and (molecule 2 in FIG. 2) (e.g., 88 mg, 0.19 mmol) can be combined in toluene (e.g., 4 mL) and aqueous $Na_2CO_3$ (e.g., 2M, 2 mL) to create a mixture. The mixture can be degassed (e.g., twice) after adding tetrakis(triphenylphosphine) palladium ($Pd(PPh_3)$) (e.g., 6 mg). The mixture can be heated (e.g., to reflux) with vigorous stirring (e.g., for two days under an argon atmosphere). The mixture can be cooled (e.g., to room temperature) and the mixture can be poured into methanol. The precipitated polymer can be recovered by filtration. The crude polymer can be purified by washing (e.g., with water, methanol and acetone) to remove oligomers and catalyst residues. In some cases, the yield of this method can be greater than 70% PFDPFBT (e.g., the yield can be 76%).

In some cases, the single fluorinated polymer PFDPFBT and the non-fluorinated polymer PFDPBT are soluble in the organic solvent tetrahydrofuran (THF). The number-average molecular weights (Mn) of PFDPFBT and PFDPBT are greater than 24.5 and 19.8 kDa, respectively. The polydispersity index (PDI) of PFDPFBT and PFDPBT are 1.8 and 2.1, respectively.

Synthesis of polymer (poly[(9,9-di(2-ethylhexyl)fluorenyl-2,7-diyl)-alt-4,4'-diphenyl-1,4-benzo-(2,1,3)-thiadiazole]) PFDPBT The method provides for the synthesis of the Pdot PFDPBT. In some cases, PFDPBT can be synthesized using a similar procedure as described for PFDPFBT using (monomer 1 FIG. 2) and (monomer 3 FIG. 2).

Synthesis of dual fluorinated polymer (poly[(9,9-di(2-ethylhexyl)fluorenyl-2,7-diyl)-alt-4,4'-diphenyl-5,6-difluoro-1,4-benzo-(2,1,3)-thiadiazole]) PFDPDFBT The method provides for the synthesis of the fluorinated semiconducting Pdot PFDPDFBT. Compound 2,7-Bis(4,4,5,5-tetramethyl-1,3,2-dioxaborolan-2-yl)-9,9-di(2-ethylhexyl) fluorene (molecule 4 FIG. 3) (e.g., 160 mg, 0.25 mmol) and 4,4-di(4'-bromophenyl)-5,6-difluoro-[2,1,3]benzothiadiazole (molecule 3 FIG. 3) (e.g., 120 mg, 0.25 mmol) can be dissolved in toluene (e.g., 5 mL) and aqueous $Na_2CO_3$ (e.g., 2M, 2 mL) to create a mixture. The mixture can be degassed (e.g., twice) after adding tetrakis(triphenylphosphine) palladium ($Pd(PPh_3)$) (e.g., 9 mg). The mixture can be heated (e.g., to reflux) with vigorous stirring (e.g., for two days under an argon atmosphere). The mixture can be cooled (e.g., to room temperature) and the mixture can be poured into methanol. The precipitated polymer can be recovered by filtration. The crude polymer can be purified by washing (e.g., with water, methanol and acetone) to remove oligomers and catalyst residues.

Figure 4:
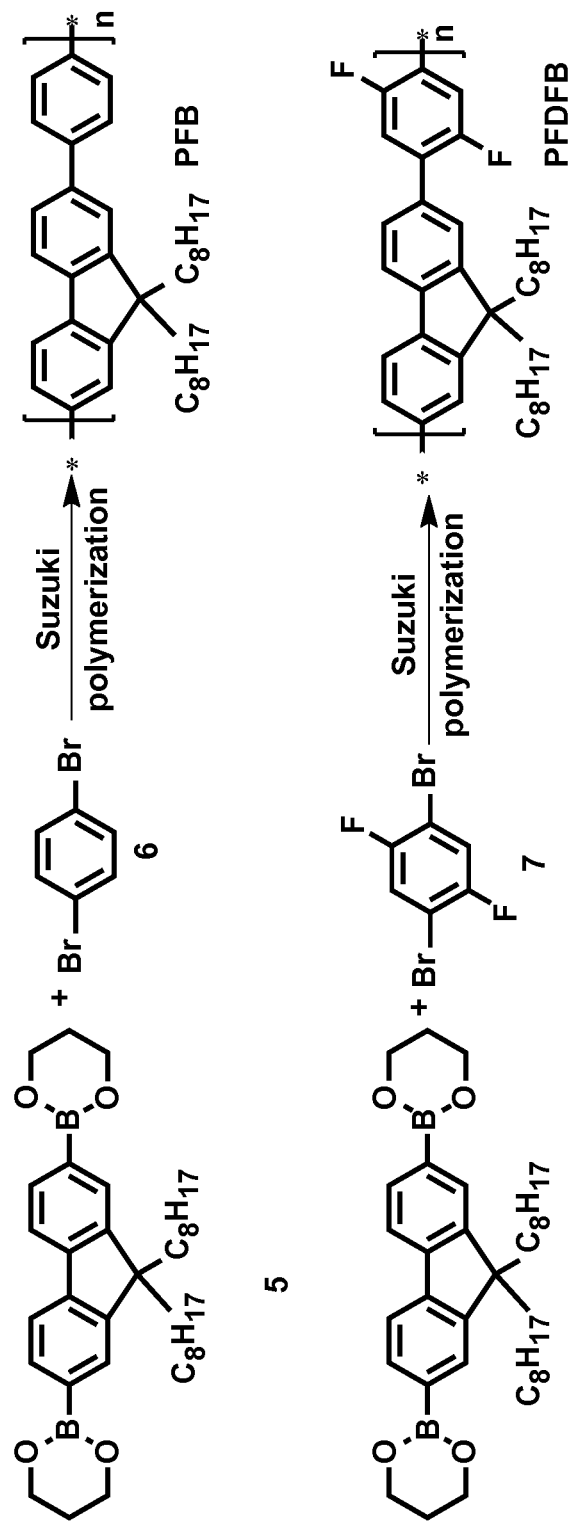
FIG. 4. The synthesis of polymer PFB and fluorinated polymer PFDFB.

Synthesis of dual fluorinated polymer (poly[(9,9-di(2-ethylhexyl)fluorenyl-2,7-diyl)-alt-1,4-benzene]) PFB The method provides for the synthesis of the fluorinated semiconducting Pdot PFB. Compound 9,9-Dioctylfluorene-2,7-diboronic acid bis(1,3-propanediol) ester (molecule 5 FIG. 4) (e.g., 285 mg, 0.5 mmol) and 1,4-dibromobenzene (molecule 6 FIG. 4) (e.g., 118 mg, 0.5 mmol) can be dissolved in toluene (e.g., 6 mL) and aqueous aqueous $Na_2CO_3$ (e.g., 2M, 2 mL) to create a mixture. The mixture can be degassed (e.g., twice) after adding tetrakis(triphenylphosphine) palladium ($Pd(PPh_3)$) (e.g., 10 mg). The mixture can be heated (e.g., to reflux) with vigorous stirring (e.g., for two days under an argon atmosphere). The mixture can be cooled (e.g., to room temperature) and the mixture can be poured into methanol. The precipitated polymer can be recovered by filtration. The crude polymer can be purified by washing (e.g., with water, methanol and acetone) to remove oligomers and catalyst residues.

Synthesis of dual fluorinated polymer (poly[(9,9-di(2-ethylhexyl)fluorenyl-2,7-diyl)-alt-2,5-difluoro-1,4-benzene]) PFDFB The method provides for the synthesis of the fluorinated semiconducting Pdot PFDFB. Compound 9,9-Dioctylfluorene-2,7-diboronic acid bis(1,3-propanediol) ester (molecule 5 FIG. 4) (e.g., 285 mg, 0.5 mmol) and (2,5-difluoro-1,4-dibromobenzene) (molecule 7 FIG. 5) (e.g., 136 mg, 0.5 mmol) can be dissolved in toluene (e.g., 6 mL) and aqueous $Na_2CO_3$ (e.g., 2M, 2 mL) to create a mixture. The mixture can be degassed (e.g., twice) after adding tetrakis(triphenylphosphine) palladium ($Pd(PPh_3)$) (e.g., 10 mg). The mixture can be heated (e.g., to reflux) with vigorous stirring (e.g., for two days under an argon atmosphere). The mixture can be cooled (e.g., to room temperature) and the mixture can be poured into methanol. The precipitated polymer can be recovered by filtration. The crude polymer can be purified by washing (e.g., with water, methanol and acetone) to remove oligomers and catalyst residues.

Preparation of Pdots

The method provides for preparation of Pdots. In some cases, single fluorinated Pdots or the single monomer non-fluorinated Pdots can be prepared by nanoprecipitation. The method of nanoprecipitation is incorporated by reference (Wu 2011, Wu, 2010 and Wu 2010; refs 13-15 in paper). PFDPFBT (or PFDPBT) and PSPEGCOOH dissolved in THF can rapidly be injected into water under ultrasonication. The prepared Pdots can be stored at 4° C. The prepared Pdots can be stored in aqueous solutions.

In some cases, dual fluorinated Pdots can be prepared by nanoprecipitation. A solution of polymer (e.g., 200 ppm) and PSPEG or PSMA (e.g., 50 ppm) blend in tetrahydrafuran (THF) (e.g., 4 mL) can quickly be injected into water (e.g., 10 mL) under ultrasonication. THF can be evaporated by nitrogen flow. The temperature of the nitrogen can be within the range of 60-80° C. In some cases the temperature of the nitrogen is 70° C. and the solution is concentrated to a volume in the range of 6-8 mL. The concentrated solution can be filtered. In some cases the filter can have pores. The pores can be 0.2 microns in diameter. The prepared Pdots aqueous solutions are kept in refrigerator for further use. The semiconducting polymer dots are prepared by similar method without using amphiphilic polymer.

Various amounts of PS-PEG-COOH (10 μL, 30 μL, 50 μL, 100 μL or 150 μL, 1000 ppm) are added to the polymer solution of PFDPFBT or PFDPBT in THF (4 mL, 50 ppm). The mixture solution is injected into DI water (10 mL) under ultrasonication. THF in the aqueous solution is then evaporated under nitrogen flow at 90° C., and the solution is concentrated to 4-5 mL. The solution is then filtered through a 0.2-μm filter. The Pdot solutions are stored at 4° C. until further use.

Detection of Pdots

The particle size and zeta-potentials of Pdots in bulk solution are characterized by dynamic light scattering (DLS) (Malvern Zetasizer NanoS). UV-Vis absorption spectra are recorded with a DU 720 scanning spectrophotometer (Beckman Coulter, Inc., CA, USA) using 1 cm quartz cuvettes. Fluorescence spectra is obtained using a commercial Perkin-Elmer fluorometer. Fluorescence quantum yields are measured using a Hamamatsu photonic multichannel analyzer C10027 equipped with CCD integrating sphere. The fluorescence quantum yields (QYs) of Pdot samples are measured with an absolute photoluminescence quantum yield measurement system (Hamamatsu photonic multichannel analyzer C10027). This system consists of a Xe arc lamp, a monochromator, an integrating sphere, and a multichannel detector. A monochromatic light source is used as the excitation light source. The excitation light is introduced into the integrating sphere by an optical fiber. A CCD camera is used as the multichannel detector.

EXAMPLES

Example 1

Polymer PFDPFBT and PFDPBT Pdots

Synthesis of single fluorinated polymer (poly[(9,9-di(2-ethylhexyl)fluorenyl-2,7-diyl)-alt-4,4'-diphenyl-5-fluoro-1,4-benzo-(2,1,3)-thiadiazole] PFDPFBT This disclosure provides for a synthesis of the fluorinated semiconducting Pdot PFDPFBT. FIG. 2 depicts the synthesis reaction to generate PFDPFBT. A Suzuki polymerization between molecules 1 and 2, of FIG. 2, with the Pd(PPh$_3$) catalyst yields the fluorinated PFDPFBT (FIG. 2). 2,7-Bis(4,4,5,5-tetramethyl-1,3,2-dioxaborolan-2-yl)-9,9-di(2-ethylhexyl) fluorene (1) (120 mg, 0.19 mmol) and 2 (88 mg, 0.19 mmol) were dissolved in a mixture of toluene (4 mL) and aqueous Na$_2$CO$_3$ (2M, 2 mL). The mixture was degassed twice after adding tetrakis(triphenylphosphine) palladium (Pd(PPh$_3$)$_4$ (6 mg). Then, the mixture was heated to reflux with vigorous stirring for two days under an argon atmosphere. After the mixture was cooled to room temperature, the solution was poured into methanol. The precipitated polymer was recovered by filtration. The crude polymer was further purified by washing with water, methanol and acetone to remove oligomers and catalyst residues. Yield: 76%. $^1$H nmR (CDCl$_3$, ppm) 8.17-8.12 (m, 4H), 7.89-7.74 (m, 11H), 2.15 (br, 4H), 0.92 (br, 15H), 0.69-0.61 (m, 15H). M$_n$ (GPC): 24.5 k, PDI: 1.8.

Synthesis of the Non-Fluorinated Polymer PFDPBT

The non-fluorinated Pdot PFDPBT was synthesized by a similar procedure for PFDPFBT using monomers 1 and 3 (FIG. 2).

The single fluorinated polymer PFDPFBT and the non-fluorinated polymer PFDPBT are soluble in the organic solvent tetrahydrofuran (THF). The number-average molecular weights (M$_n$) of PFDPFBT and PFDPBT estimated by gel permeation chromatography (GPC) were 24.5 and 19.8 kDa with a polydispersity index (PDI) of 1.8 and 2.1, respectively.

Purity of PFDPFBT

The synthesized PFDPFBT was analyzed for purity by nmR. The purity analysis was $^1$H nmR (CDCl$_3$, ppm) 8.17-8.12 (m, 4H), 7.89-7.74 (m, 11H), 2.15 (br, 4H), 0.92 (br, 15H), 0.69-0.61 (m, 15H). Mn (GPC): 24.5 k, PDI: 1.8.

Purity of PFDPBT

The synthesized PFDPBT was analyzed for purity by nmR. The purity analysis was $^1$H nmR (CDCl$_3$, ppm) 8.16 (m, 4H), 7.93-7.83 (m, 8H), 7.76-7.71 (m, 4H), 2.15 (br, 4H), 0.92 (br, 15H), 0.69-0.55 (m, 15H). M$_n$ (GPC): 19.8 k, PDI: 2.1.

Characteristics of PFDPFBT and PFDPBT

We studied the sizes and shapes of the Pdots by dynamic light scattering (DLS) and transmission electron microscopy (TEM). FIG. 1 shows the representative DLS and TEM images of PFDPFBT and PFDPBT Pdots at a ratio of 20:5 (polymer:PSPEGCOOH) in weight. From DLS data (FIGS. 1A and 1C), both Pdots showed similar hydrodynamic diameters of ~16 nm, which is consistent with the TEM measurements. As measured by TEM, PFDPBT Pdots were spherical particles with an average diameter of 14 nm (FIG. 1D). Surprisingly, we found the fluorinated Pdots had rod or ellipsoidal shapes (FIG. 1B) when blended with PSPEG-COOH. The case ratio was between 1.6 and 3, with a length between 20 and 40 nm.

Methods for Detection of PFDPFBT and PFDPBT Characteristics $^1$H and $^{13}$C nmR spectra were recorded on Bruker AV 300 or 500 spectrometers. $^1$H nmR and $^{13}$C nmR spectra used tetramethylsilane (TMS) as an internal standard in CDCl$_3$. The molecular weight of polymers was measured by the GPC method (Viscotek TDA305 GPC), and polystyrene was used as the standard (THF as eluent). The particle size and zeta-potentials of Pdots in bulk solution were characterized by DLS (Malvern Zetasizer NanoS). TEM measurements were recorded on a transmission electron microscope (FBI Tecnai F20). UV-vis absorption spectra were recorded with a DU 720 scanning spectrophotometer (Beckman Coulter, Inc., CA, USA) using 1-cm quartz cuvettes. Fluorescence spectra of Pdots in aqueous solution were obtained using a Perkin Elmer LS-50B Luminescence Spectrophotometer. Fluorescence quantum yields were measured using a Hamamatsu photonic multichannel analyzer C10027 equipped with a CCD integrating sphere. ESI-MS spectra were obtained using a Bruker APEX Qe 47e Fourier transform (ion cyclotron resonance) mass spectrometer.

Preparation of PFDPFBT and PFDPBT Pdots

Various amounts of PS-PEG-COOH (10 μL, 30 μL, 50 μL, 100 μL or 150 μL, 1000 ppm) was added to the polymer solution of PFDPFBT or PFDPBT in THF (4 mL, 50 ppm). The mixture solution was injected into DI water (10 mL) under ultrasonication. THF in the aqueous solution was then evaporated under nitrogen flow at 90° C., and the solution was concentrated to 4-5 mL. The solution was then filtered through a 0.2-μm filter. The Pdot solutions were stored at 4° C. until further use.

The Optical Properties of Polymer PFDPFBT and PFDPBT Pdots

Figure 6:
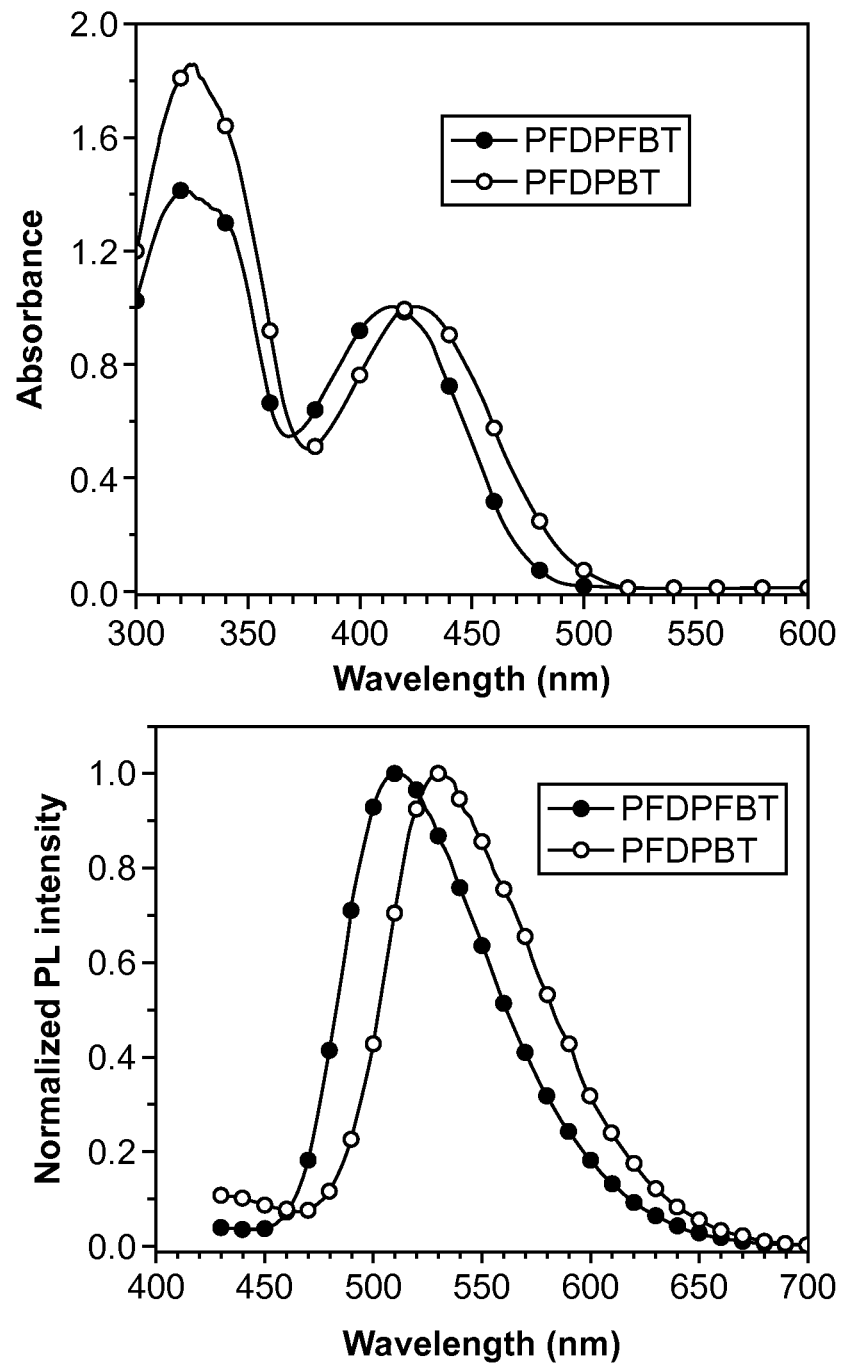
FIG. 6. The UV-Vis and PL spectra of PFDPFBT and PFDPBT Pdots in water.
Figure 7:
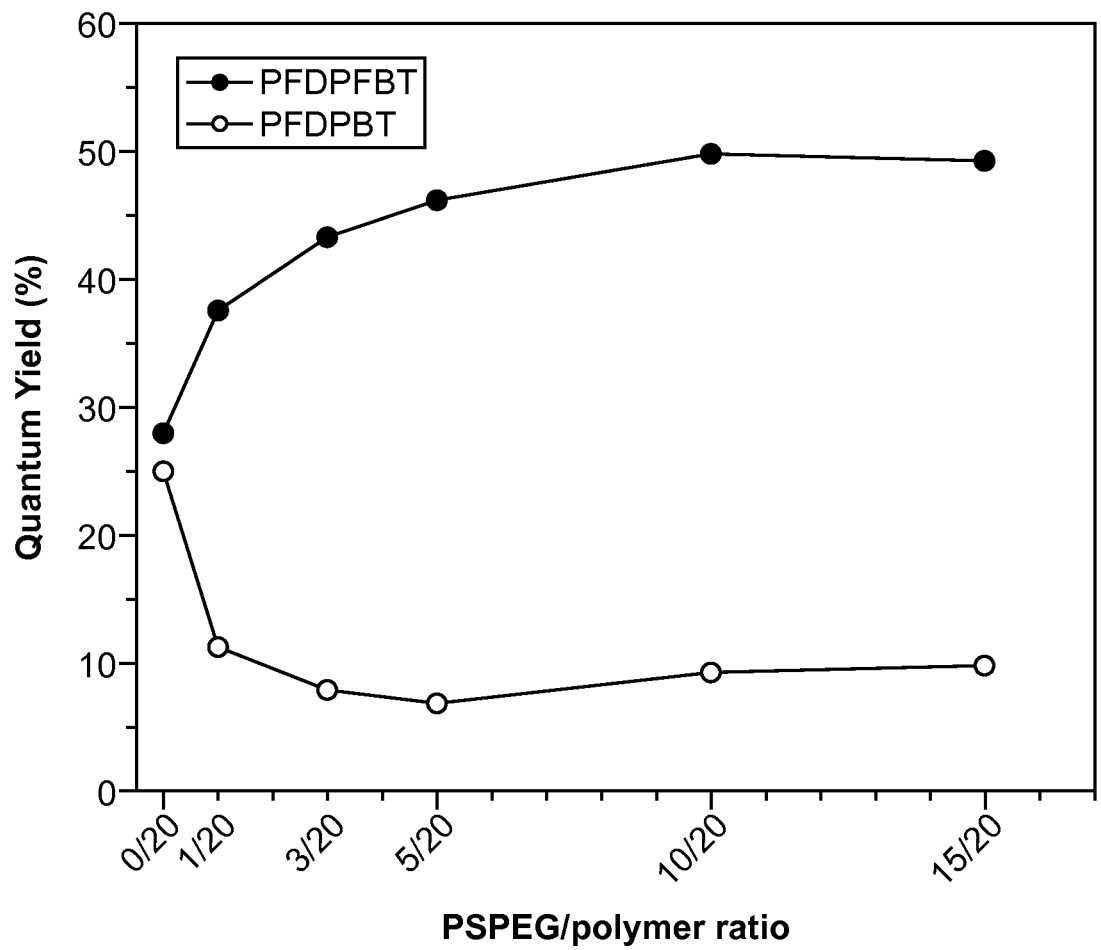
FIG. 7. The quantum yield changes of different PS-PEG-COOH concentration at 20 ppm polymer.

FIG. 6 shows the absorption and photoluminescence (PL) spectra of PFDPFBT and PFDPBT Pdots. The charge transfer (CT) absorption peak in the long wavelength region for PFDPBT Pdot was at ~425 nm; the CT peak for the PFDPFBT Pdot, with the introduction of fluorine atom, blue-shifted the peak to ~410 nm. This result suggests that the introduction of fluorine atom enhanced CT between the donor (fluorene segment) and the acceptor (fluorobenzothiadiazole segment). The PL peak of the PFDPBT Pdot was at ~530 nm; the PL peak was blue-shifted to ~510 nm, with a purer green emission, for PFDPFBT Pdots. Bare PFDPFBT and PFDPBT Pdots without any PSPEGCOOH showed similar quantum yields (QYs) of 25% and 28%, respectively, which indicates that the two types of polymer chains have a similar degree of aggregation in Pdots. However, the difference in quantum yields between the two types of Pdots when blended with PSPEGCOOH displayed a remarkable difference: the quantum yield of PFDPFBT/PSPEGCOOH (20:5 w/w) Pdots increased to 46% but that of PFDPBT Pdots decreased to 7%. This big difference in QY caused by the presence of PSPEGCOOH prompted us to study how the amount of blended PSPEGCOOH affected the resulting QY of the two types of Pdots. The QY of PFDPFBT Pdots exhibited a gradual increase when the weight ratio was increased from 20:1 to 20:10 (FIG. 7). In contrast, for PFDPBT Pdots, the QY first decreased to 7% at a ratio of 20:5 and then slightly increased from 7% to 10% at higher PSPEGCOOH amounts.

Example 2

Polymer PFDFB and PFB

Synthesis of single fluorinated polymer (poly[(9,9-di)2-ethylhexyl)fluorenyl-2,7-diyl)-alt-2,5-difluoro-1,4-benzene]) PFDFB The method provides for a synthesis of the fluorinated semiconducting Pdot PFDFB (FIG. 4). 9,9-Dioctylfluorene-2,7-diboronic acid bis(1,3-propanediol) ester (5) (285 mg, 0.5 mmol) and 7 (136 mg, 0.5 mmol) were dissolved in a mixture of toluene (6 mL) and aqueous $Na_2CO_3$ (2M, 2 mL). The mixture was degassed twice after adding tetrakis(triphenylphosphine) palladium $(Pd(PPh_3)_4)$ (10 mg). Then, the mixture was heated to reflux with vigorous stirring for two days under an argon atmosphere. After the mixture was cooled to room temperature, the solution was poured into methanol. The precipitated polymer was recovered by filtration. The crude polymer was further purified by washing with water, methanol and acetone to remove oligomers and catalyst residues. Yield: 72%.

Synthesis of the Non-Fluorinated Polymer PFB

The non-fluorinated Pdot PFB was synthesized by the following method (FIG. 4). 9,9-Dioctylfluorene-2,7-diboronic acid bis(1,3-propanediol) ester (5) (285 mg, 0.5 mmol) and 6 (118 mg, 0.5 mmol) were dissolved in a mixture of toluene (6 mL) and aqueous $Na_2CO_3$ (2M, 2 mL). The mixture was degassed twice after adding tetrakis(triphenylphosphine) palladium $(Pd(PPh_3)_4)$ (10 mg). Then, the mixture was heated to reflux with vigorous stirring for two days under an argon atmosphere. After the mixture was cooled to room temperature, the solution was poured into methanol. The precipitated polymer was recovered by filtration. The crude polymer was further purified by washing with water, methanol and acetone to remove oligomers and catalyst residues. Yield: 82%.

The single fluorinated polymer PFDPFBT and the non-fluorinated polymer PFDPBT are soluble in the organic solvent tetrahydrofuran (THF). The number-average molecular weights (Mn) of PFDPFBT and PFDPBT estimated by gel permeation chromatography (GPC) were 24.5 and 19.8 kDa with a polydispersity index (PDI) of 1.8 and 2.1, respectively.

Preparation of PFDFB and PFB Pdots

Pdots were prepared by nano-precipitation method. A solution of polymer (200 ppm) and PSPEG or PSMA (50 ppm) blend in THF (4 mL) was quickly injected into water (10 mL) under ultrasonication. THF was evaporated by $N_2$ flow at 70° C. and the solution was concentrated to 6-8 mL, followed by filtration through a 0.2 micron filter. The prepared Pdots aqueous solutions were kept in refrigerator for further use. The semiconducting polymer dots were prepared by similar method without using amphiphilic polymer.

Methods for Detection of PFDFB and PFB Characteristics

The particle size and zeta-potentials of Pdots in bulk solution was characterized by dynamic light scattering (DLS) (Malvern Zetasizer NanoS). UV-Vis absorption spectra were recorded with a DU 720 scanning spectrophotometer (Beckman Coulter, Inc., CA, USA) using 1 cm quartz cuvettes. Fluorescence spectra were obtained using a commercial Perkin-Elmer fluorometer. Fluorescence quantum yields were measured using a Hamamatsu photonic multichannel analyzer C10027 equipped with CCD integrating sphere. The fluorescence quantum yields (QYs) of Pdot samples were measured with an absolute photoluminescence quantum yield measurement system (Hamamatsu photonic multichannel analyzer C10027). This system consists of a Xe arc lamp, a monochromator, an integrating sphere, and a multichannel detector. A monochromatic light source was used as the excitation light source. The excitation light was introduced into the integrating sphere by an optical fiber. A CCD camera was used as the multichannel detector.

The Optical Properties of Polymer PFDFB and PFB Pdots

Figure 8:
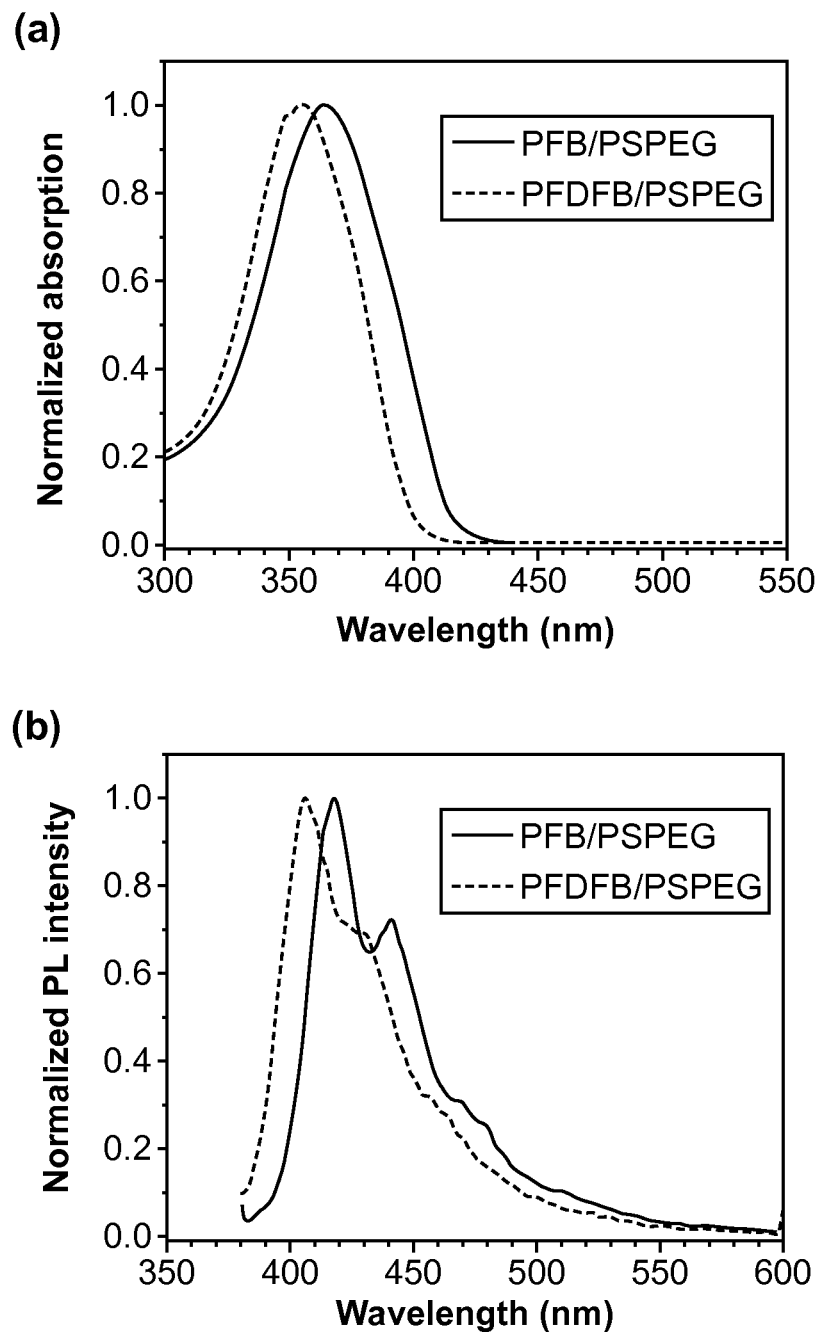
FIG. 8. The UV-Vis (a) and PL (b) spectra of PFB/PSPEG and PFDFB/PSPEG Pdots in aqueous solution.
Figure 9:
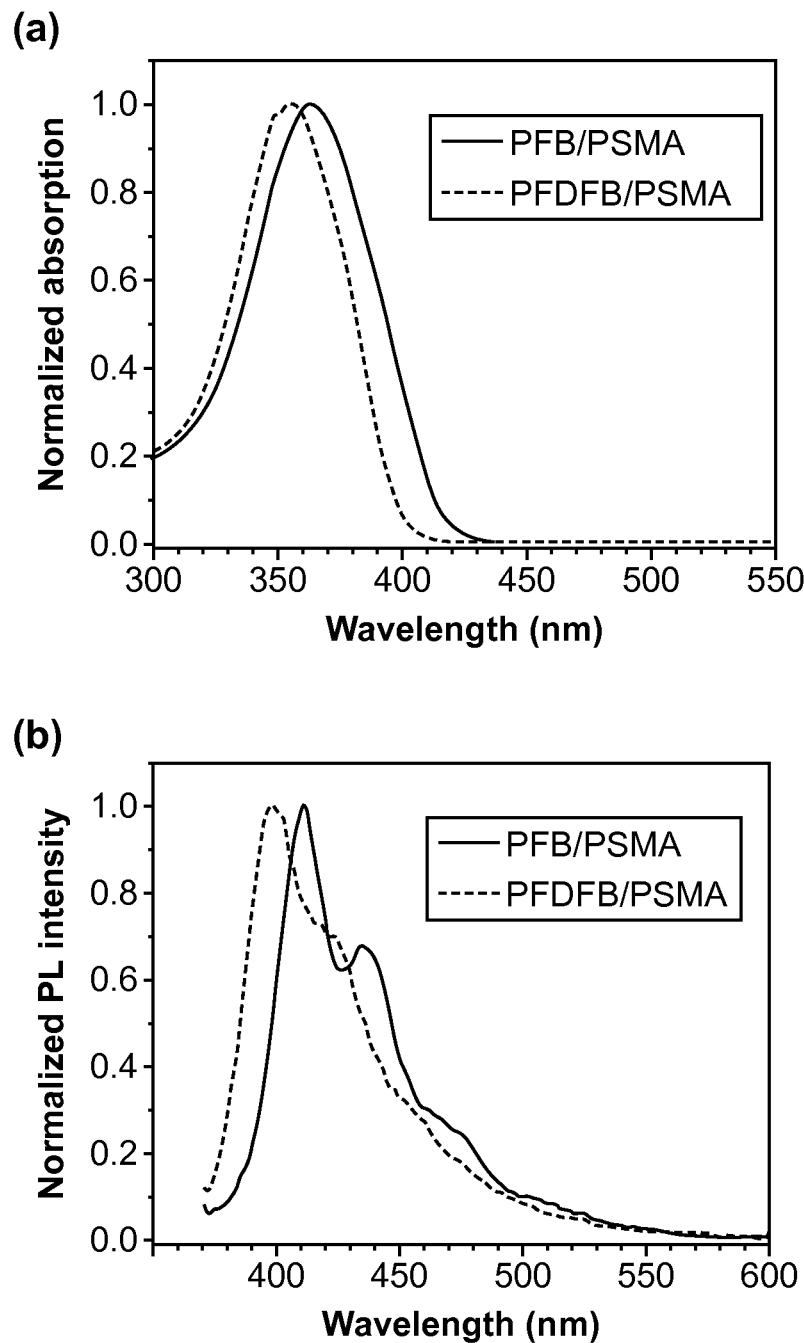
FIG. 9. The UV-Vis (a) and PL (b) spectra of PFB/PSMA and PFDFB/PSMA Pdots in aqueous solution.
Figure 10:
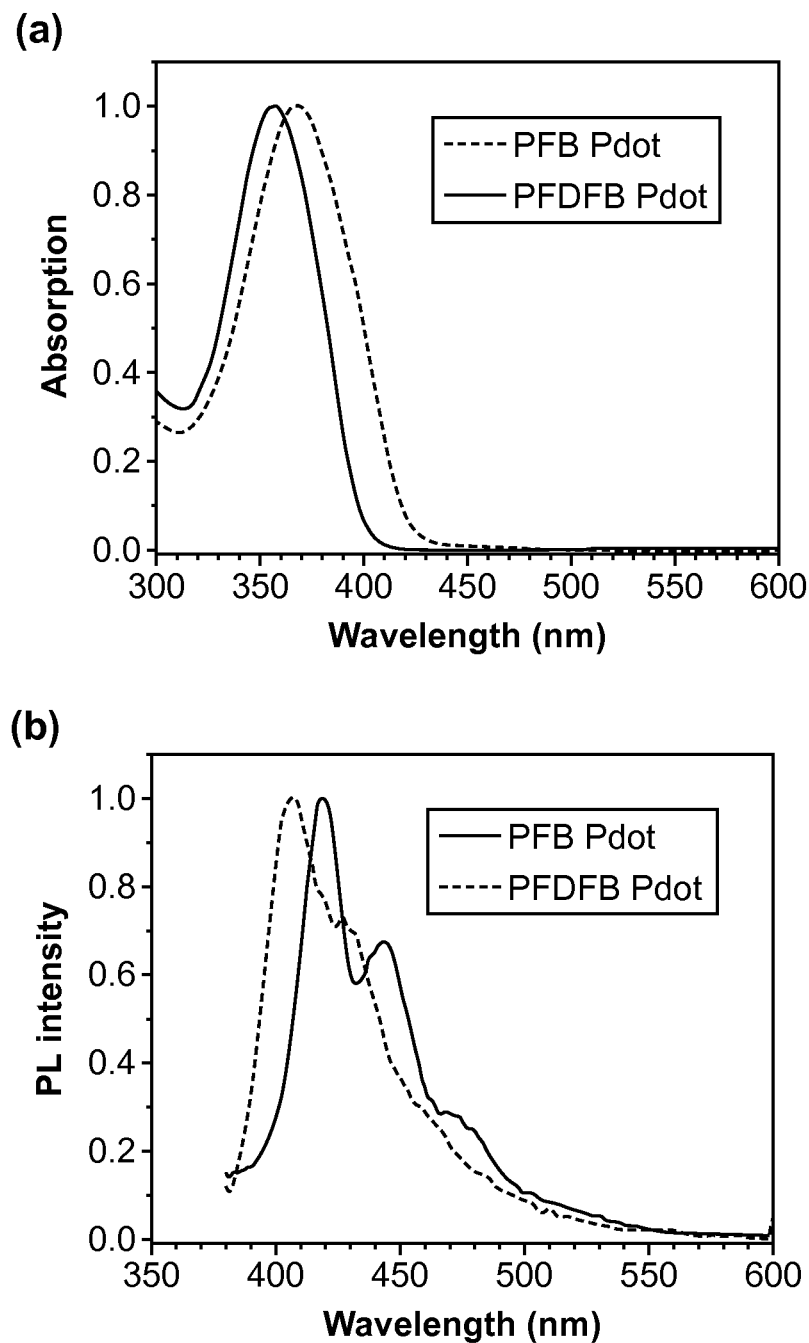
FIG. 10. The UV-Vis (a) and PL (b) spectra of PFB and PFDFB Pdots in aqueous solution.

FIGS. 8, 9, and 10 show the UV-Vis and PL spectra of PFB/PSPEG and PFDFB/PSPEG, PFB/PSMA and PFDFB/PSMA, bare PFB and PFDFB Pdots. Similar with above polymer, the fluorinated polymer PFDFB shows the blue-shift in their absorption and fluorescence spectra. Table 1 below summarizes these data.

TABLE 1

Summary of optical properties of PFB/PSMA, PFDFB/PSMA, PFB/PSPEPG, PFDFB/PSPEG, PFB and PFDFB Pdots.

| Pdots | λmax (UV) | λmax (PL) | DLS | PLQY |
|---|---|---|---|---|
| PFB/PSMA | 363 nm | 418 nm | 18 nm | 15.9% |
| PFDFB/PSMA | 355 nm | 406 nm | 20 nm | 22.4% |
| PFB/PSPEG | 364 nm | 417 nm | 18 nm | 25% |
| PFDFB/PSPEG | 355 nm | 406 nm | 19 nm | 29% |
| PFB only | 366 nm | 418 nm | 35 nm | 22.2% |
| PFDFB only | 357 nm | 407 nm | 22 nm | 34.7% |

For example, in PSMA type Pdots, the absorption peak in non-fluorinated polymer PFB Pdot is 363 nm, it shifted to 355 nm in the difluoro-substituted polymer PFDFB Pdot; there is ~8-9 nm shift. A similar trend in fluorescent spectra was found, where the fluorinated polymer blue-shifted ~12 nm. It is noted that in this type of polymer, the blue-shift in both UV-Vis and PL spectra is weaker than the fluorinated benzothiadiazole polymer, which is a kind of charge transfer polymer.

The quantum yields for these Pdots are listed in Table 1. In PSMA Pdots, PFB/PSMA Pdot has a QY of 15.9%, but the QY increased to 22.4% in the fluorinated PFDFB/PSMA Pdot. It is a 40% increase in quantum yield under same condition with similar size. In PSPEG Pdots, the QY of fluorinated PFDFB/PSPEG Pdot is also higher than that of non-fluorinated PFB/PSPEG Pdot, where there is around 16% increase in PSPEG Pdots. In bare polymer Pdots, the QY for PFB Pdot is 22.2%, but the fluorinated PFDFB Pdot has the QY of 34.7%, a ~56% increase.

Example 3

Polymer PFDPDFBT

Synthesis of double fluorinated polymer (poly[(9,9-di(2-ethylhexyl)fluorenyl-2,7-diyl)-alt-4,4'-diphenyl-5,6-difluoro-1,4-benzo-(2,1,3)-thiadiazole]) PFDPDFBT The method provides for a synthesis of the fluorinated semiconducting Pdot PFDPDFBT. FIG. 3 depicts the synthesis reaction to generate PFDPDFBT., 7-Bis(4,4,5,5-tetramethyl-1,3,2-dioxaborolan-2-yl)-9,9-di(2-ethylhexyl) fluorene (4) (160 mg, 0.25 mmol) and 3 (120 mg, 0.25 mmol) were dissolved in a mixture of toluene (5 mL) and aqueous $Na_2CO_3$ (2M, 2 mL). The mixture was degassed twice after adding tetrakis(triphenylphosphine) palladium ($Pd(PPh_3)_4$) (9 mg). Then, the mixture was heated to reflux with vigorous stirring for two days under an argon atmosphere. After the mixture was cooled to room temperature, the solution was poured into methanol. The precipitated polymer was recovered by filtration. The crude polymer was further purified by washing with water, methanol and acetone to remove oligomers and catalyst residues. Yield: 65%.

Methods for Detection of PFDPDFBT Characteristics

The particle size and zeta-potentials of Pdots in bulk solution was characterized by dynamic light scattering (DLS) (Malvern Zetasizer NanoS). UV-Vis absorption spectra were recorded with a DU 720 scanning spectrophotometer (Beckman Coulter, Inc., CA, USA) using 1 cm quartz cuvettes. Fluorescence spectra were obtained using a commercial Perkin-Elmer fluorometer. Fluorescence quantum yields were measured using a Hamamatsu photonic multi-channel analyzer C10027 equipped with CCD integrating sphere. The fluorescence quantum yields (QYs) of Pdot samples were measured with an absolute photoluminescence quantum yield measurement system (Hamamatsu photonic multichannel analyzer C10027). This system consists of a Xe arc lamp, a monochromator, an integrating sphere, and a multichannel detector. A monochromatic light source was used as the excitation light source. The excitation light was introduced into the integrating sphere by an optical fiber. A CCD camera was used as the multichannel detector.

Preparation of PFDPDFBT Pdots

Pdots were prepared by nano-precipitation method. A solution of polymer (200 ppm) and PSPEG or PSMA (50 ppm) blend in THF (4 mL) was quickly injected into water (10 mL) under ultrasonication. THF was evaporated by $N_2$ flow at 70° C. and the solution was concentrated to 6-8 mL, followed by filtration through a 0.2 micron filter. The prepared Pdots aqueous solutions were kept in refrigerator for further use.

The Optical Properties of Polymer PFDPDFBT and PFDPDBT Pdots

Figure 5:
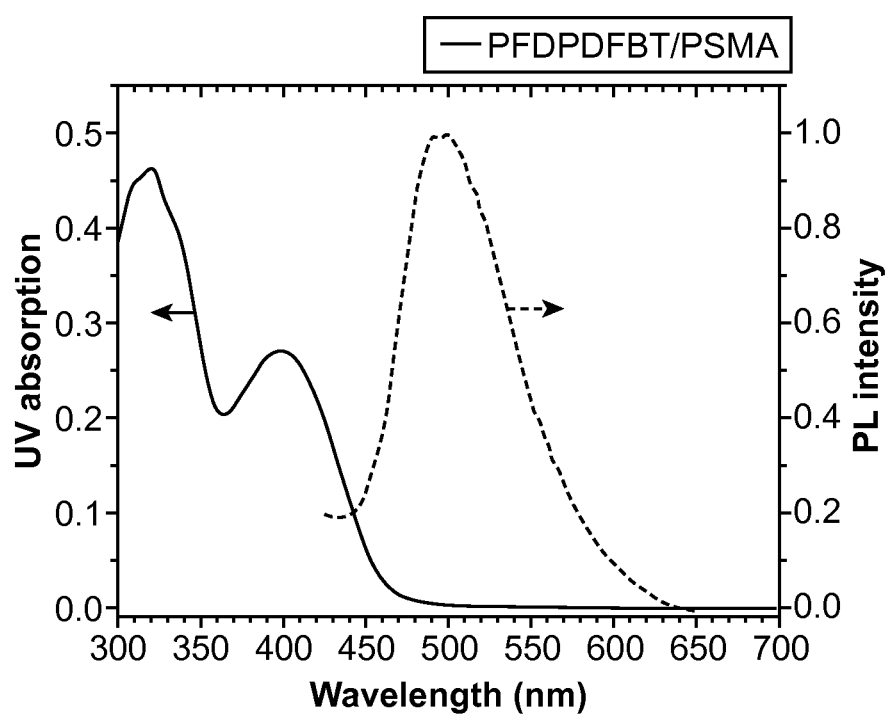
FIG. 5. The UV-Vis and PL spectra of PFDPDFBT/PSMA Pdot in aqueous solution.
Figure 11:
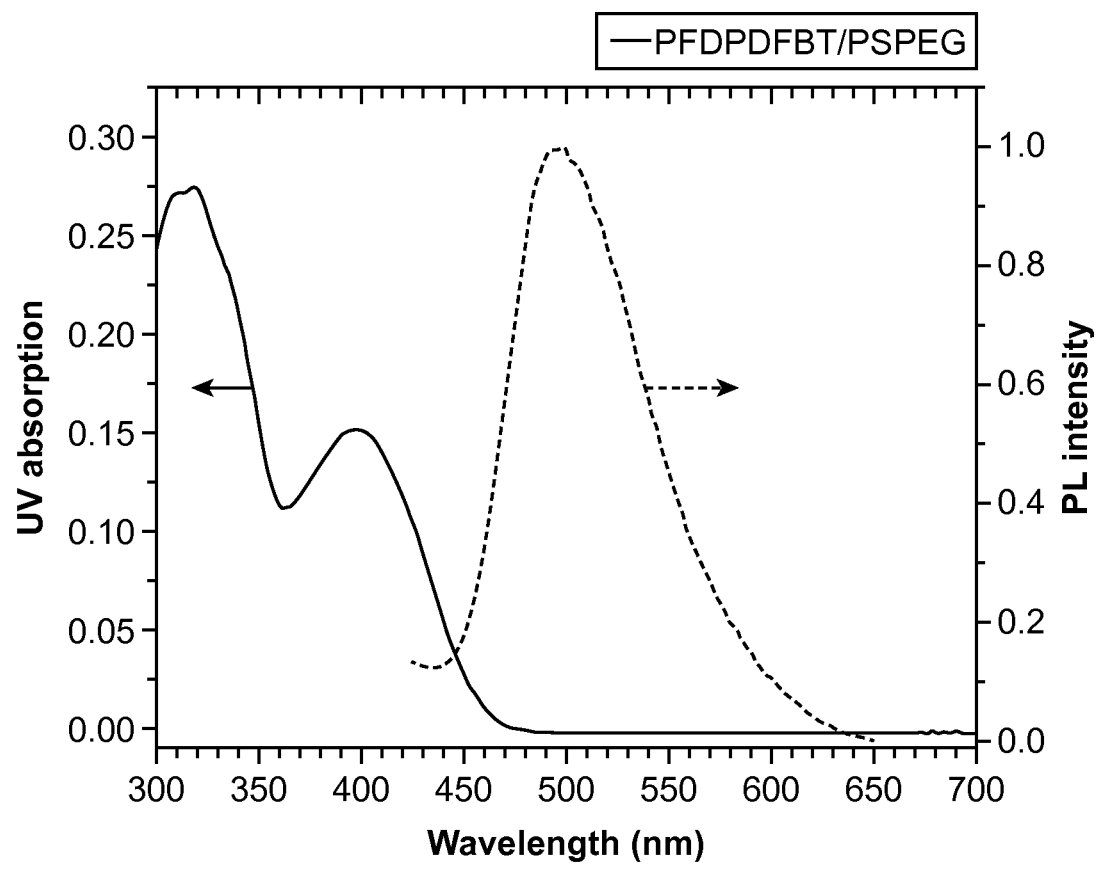
FIG. 11. The UV-Vis and PL spectra of PFDPDFBT/PSPEG Pdot in aqueous solution.
Figure 12:
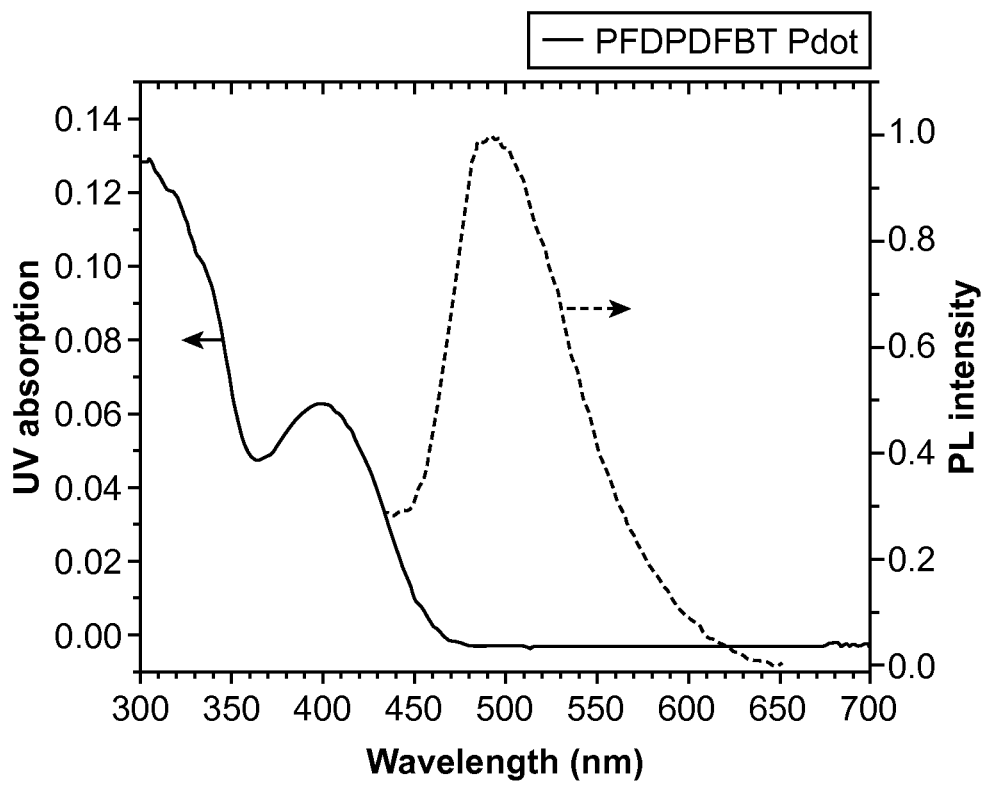
FIG. 12. The UV-Vis and PL spectra of PFDPDFBT Pdot in aqueous solution.

FIGS. 11, 5, and 12 show the UV-Vis and PL spectra of PFDPDFBT/PSPEG, PFDPDFBT/PSMA and PFDPDFBT Pdots. After introducing difluoro-substitutes onto the benzothiadiazole unit, the UV-Vis and PL spectra of PFDPDFBT in all Pdots further blue-shifted. The absorption maximum peak at longer wavelength is ~397 nm, which is around 13 nm blue-shift compared with the monofluoro-substituted PFDPFBT Pdot, and ~23 nm blue-shift in comparison with non-fluorinated polymer PFDPBT Pdot. The fluorescence maximum peak for PFDPDFBT/PSPEG (or PSMA) Pdots is 499 nm, it is ~493 nm in PFDPDFBT-only Pdot. The PL peaks have 10-30 nm blue shift compared to PFDPFBT or PFDPBT Pdots. The blue shift in both absorption and PL spectra should be attributed to the stronger electron-withdrawing properties of two fluorine substitutes on benzothiadiazole unit.

The particle sizes for PFDPDFBT/PSPEG, PFDPDFBT/PSMA and PFDPDFBT Pdots are 17 nm, 25 nm and 55 nm, respectively. (Table 2)

TABLE 2

The summary of optical properties of PFDPDFBT/PSPEG, PFDPDFBT/PSMA and PFDPDFBT Pdots.

| Pdots | λmax (UV) | λmax (PL) | DLS | PLQY |
|---|---|---|---|---|
| PFDPDFBT/PSPEG | 398 nm | 499 nm | 17 nm | 31.4% |
| PFDPDFBT/PSMA | 397 nm | 499 nm | 25 nm | 29.6% |
| PFDPDFBT | 397 nm | 493 nm | 55 nm | 27.3% |

The quantum yield for PFDPDFBT/PSPEG, PFDPDFBT/PSMA and PFDPDFBT Pdots are 31.4%, 29.6% and 27.3%, respectively. (Table 2) In PFDPDFBT/PSPEG Pdot, the quantum yield (31.4%) is around 5 times higher than that of PFDPBT/PSPEG Pdot (non-fluorinated polymer), which further prove that the fluorine substitute is an effective way to enhance the quantum yield, and further increase brightness. The enhancement may be caused by that F—F and/or F—H interactions, together with the strong hydrophobic property of F atom, which may have led to a rigid and extended polymer chain, thus minimizing aggregation-induced quenching. The rigid and extended polymer chain present in PFDPDFBT/PSPEG Pdots also had an impact on the shape of the resultant Pdots.

Example 4

Use of Pdots for Detection of MCF-7 Cells by Flow Cytometry and Cellular Imaging Bioconjugation of Pdots Pdot bioconjugation was performed via the EDC-catalyzed reaction between carboxyl groups on the Pdots' surface and the amine groups on the biomolecules. In a typical bioconjugation reaction, 80 µL of polyethylene glycol (5% w/v PEG, MW 3350) and 80 µL of concentrated HEPES buffer (1 M) were added to 4 mL of Pdot solution (~50 mg/mL in water), resulting in a Pdot solution in 20 mM HEPES buffer with a pH of 7.3. Then, 240 µL of streptavidin (Invitrogen, Eugene, Oreg., USA) was added to the solution and mixed well on a vortex. 8 µL of a freshly prepared EDC solution (10 mg/mL in water) was added to the solution, and the mixture was left on a rotary shaker. After stirring for 4 h at room temperature, Triton-X 100 (0.25% (w/v), 80 µL) and bovine serum albumin (BSA; 2% (w/v), 80 µL) were added. The mixture was left on rotary shaker for 1 h Finally, the resulting Pdot bioconjugates were separated from free biomolecules by gel filtration using Sephacryl HR-300 gel media.

Cell Culture

The breast cancer cell line MCF-7 was purchased from American Type Culture Collection (Manassas, Va., USA). Cells were cultured at 37° C., 5% $CO_2$ in Eagle's minimum essential medium supplemented with 10% fetal bovine serum (FBS), 50 U/mL penicillin, and 50 µg/mL streptomycin. The cells were cultured prior to experiments until confluence was reached. The cells were harvested from the culture flask by briefly rinsing with culture media followed by incubation with 5 mL of trypsin-EDTA solution (0.25 w/v % trypsin, 0.53 mM EDTA) at 37° C. for 5-15 min. After complete detachment, the cells were rinsed, centrifuged, and resuspended in labeling buffer (1×PBS, 2 mM EDTA, 1% BSA). The cell concentration was determined by microscopy using a hemacytometer.

To evaluate the performance of the two types of Pdots for biological applications, we applied them to flow cytometry and cellular imaging. We conjugated the Pdots to streptavidin via the 1-ethyl-3-[3-dimethylaminopropyl]carbodiimide hydrochloride (EDC)-catalyzed coupling reaction (see Experimental Section for details). We then used them to label MCF-7 cells incubated with biotinylated antibodies against the cell-surface protein EpCAM. The MCF-7 cells were incubated with a biotinylated primary anti-EpCAM antibody and then with Pdot-streptavidin probes.

Flow Cytometery

For specific cell labeling with the Pdot-streptavidin conjugates, a million cells were blocked with BlockAid blocking buffer (Invitrogen, Eugene, Oreg., USA). The cells were then incubated sequentially with biotinylated primary anti-EpCAM antibody (used to label the cell-surface EpCAM receptors on MCF-7 cells) and 10 µg/mL (based on Pdots) Pdot-streptavidin for 30 min each, followed by two washing steps using labeling buffer. Finally, the specifically labeled cells were fixed in 0.6 mL of 4% (v/v) paraformaldehyde solution. For the control labeling, biotinylated primary anti-EpCAM antibody was not added. Flow cytometry measurements were performed on fresh samples with $10^6$ cells/0.5 mL, prepared following the procedure described previously.[52] The flow cytometer FACS Canto II (BD Bioscience, San Jose, Calif., USA) was used for both Pdots with a 405-nm laser. Corresponding detection channels for fluorescence emission were filtered by a 502 nm long-pass followed by a 510/50 nm band-pass filter. Scattered light and fluorescence emission were detected by photomultiplier tube arrays. Representative populations of cells were chosen by selection of appropriate gates. Detection of cell scattered and fluorescent light was continued until at least $10^4$ events had been collected in the active gate. Data were analyzed using FlowJo Software (Tree Star, Inc., Ashland, Oreg., USA).

Figure 13:
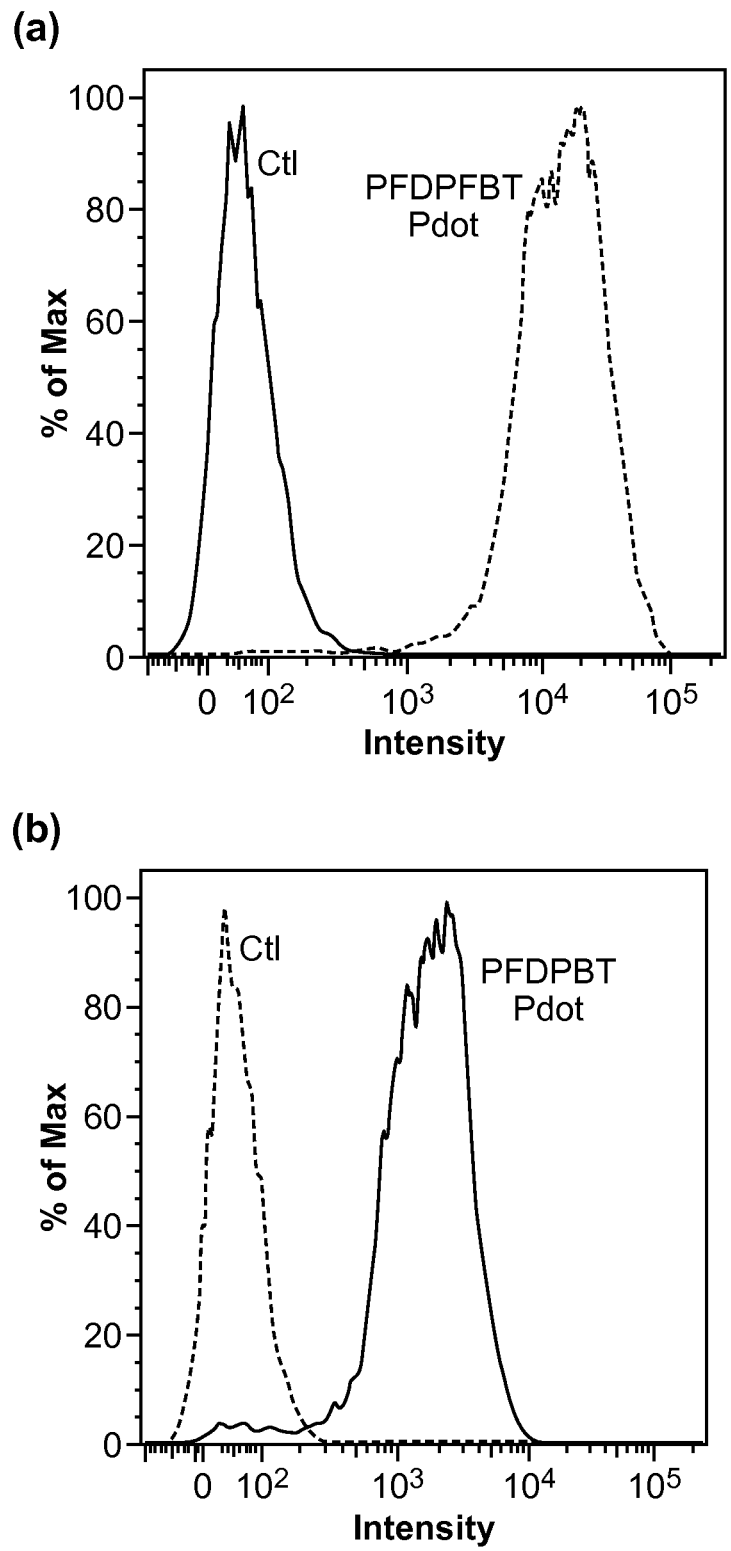
FIG. 13. The intensity distributions of flow cytometry of MCF-7 breast cancer cells labeled via non-specific binding (negative control) and positive specific targeting (positive) using (a) PFDPFBT and (b) PFDPBT Pdots conjugated with streptavidin.
Figure 14:
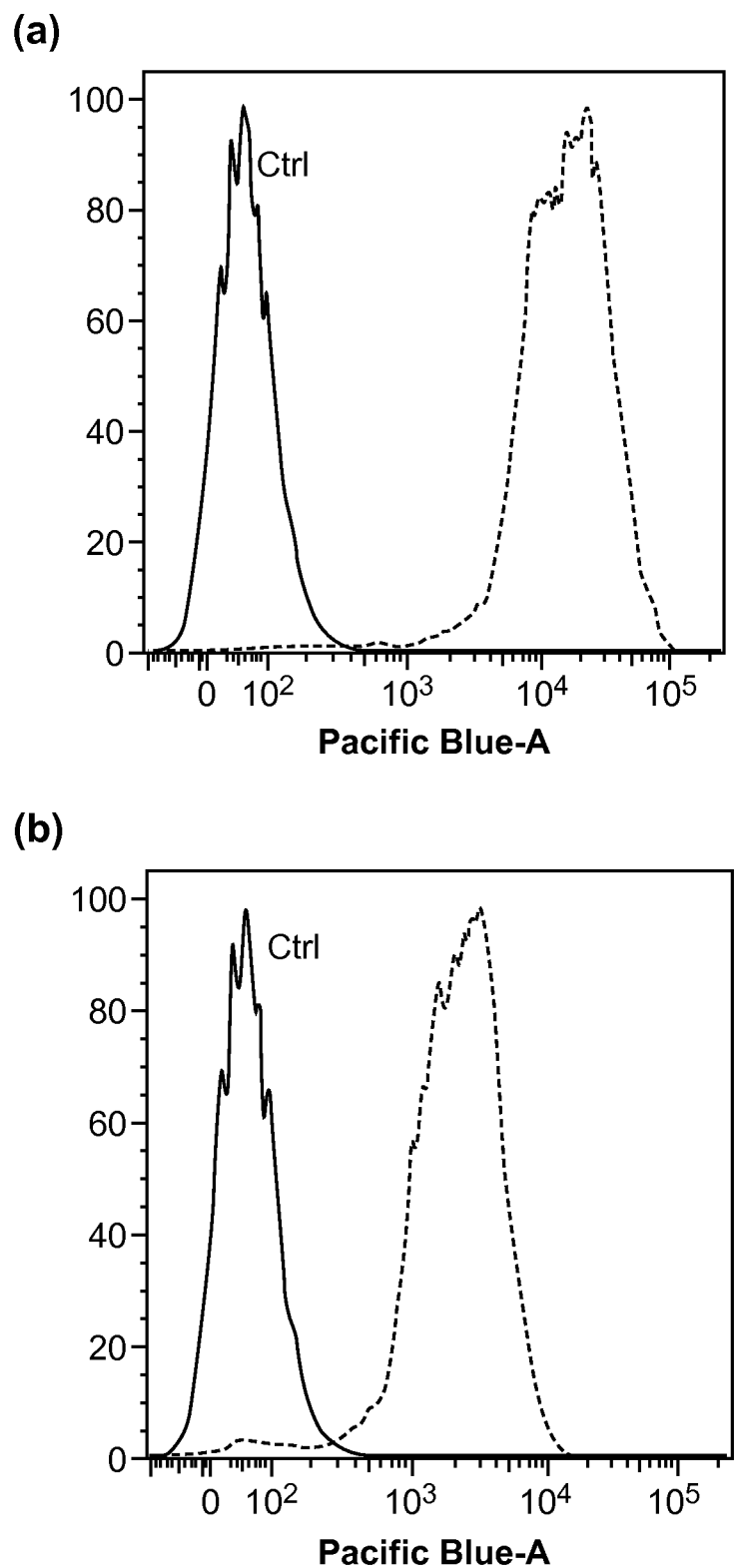
FIG. 14. The intensity distributions of flow cytometry (measured with 530 nm/30 nm band-pass filter) of MCF-7 breast cancer cells labeled via non-specific binding (negative control) and positive specific targeting (positive) using (a) PFDPFBT/PSPEGCOOH and (b) PFDPBT/PSPEGCOOH Pdots conjugated with streptavidin.

FIG. 13 shows the flow cytometry results. There was excellent separation between Pdot-streptavidin-labelled cells and the negative control, which were cells incubated with Pdots but in the absence of the biotinylated primary antibody. MCF-7 cells labelled with bioconjugated PFDPFBT Pdots exhibited a much higher intensity than cells labelled with bioconjugated PFDPBT Pots under identical labelling and experimental conditions. Quantitative analysis of the flow cytometry results taken with a 510/50 nm bandpass and a 502-nm long-pass filter showed that the average fluorescence intensity of MCF-7 cells labelled with PFDPFBT Pdots was ~8 times brighter than those labelled with PFDPBT Pdots. This result is consistent with the QY and molar absorption coefficient of both Pdots. We also used a different band-pass filter (530 nm/30 nm) and obtained similar results (FIG. 14).

Cellular Labeling and Imaging

For labeling cell-surface proteins with the Pdot-streptavidin conjugates, live MCF-7 cells in the glass-bottomed culture dish were blocked with BlockAid blocking buffer (Invitrogen, Eugene, Oreg., USA). Then, the MCF-7 cells were incubated sequentially with biotinylated primary anti-EpCAM antibody (used to label the cell-surface EpCAM receptors on MCF-7 cells) and 5 nm Pdot-streptavidin for 30 min each, followed by two washing steps after each incubation. Biotinylated primary anti-EpCAM antibody was not added to the control sample. The Pdot-tagged cells were then counterstained with Hoechst 34580 and imaged immediately on a fluorescence confocal microscope (Zeiss LSM 510). Both types of Pdot-labeled MCF-7 cells were excited by a 405-nm diode laser or a 488-nm argon laser. A Plan-Apochromat 63x/1.40 oil DIC objective lens was utilized for imaging.

Figure 15:
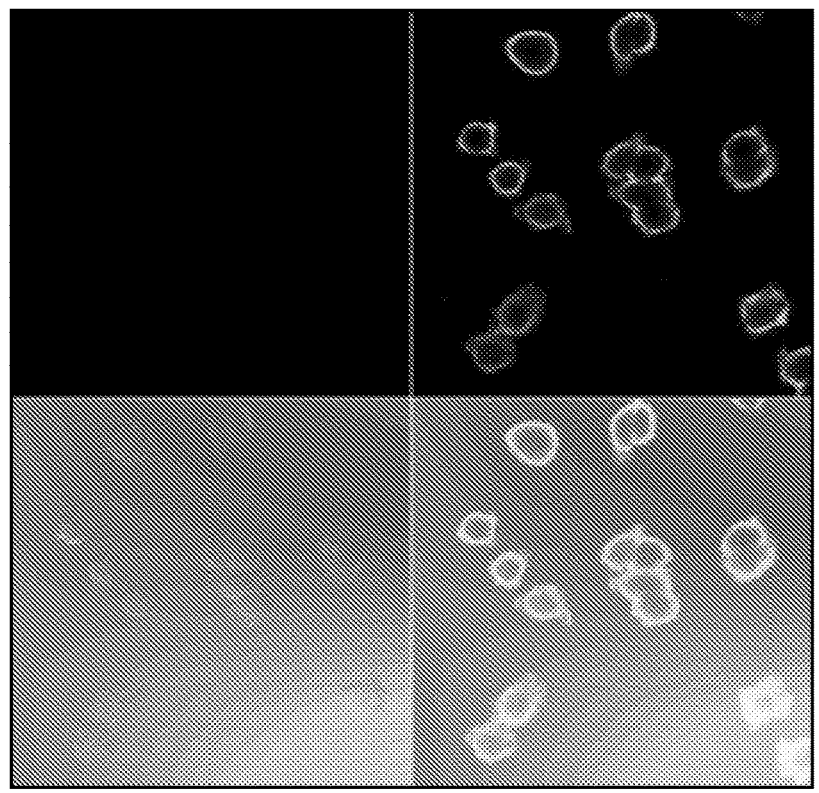
FIG. 15. Confocal fluorescence images of MCF-7 breast cancer cells labelled with (a) PFDPFBT/PS-PEG-COOH/streptavidin probes and (b) PFDPBT/PS-PEG-COOH/streptavidin probes under 405-nm excitation.
Figure 15:
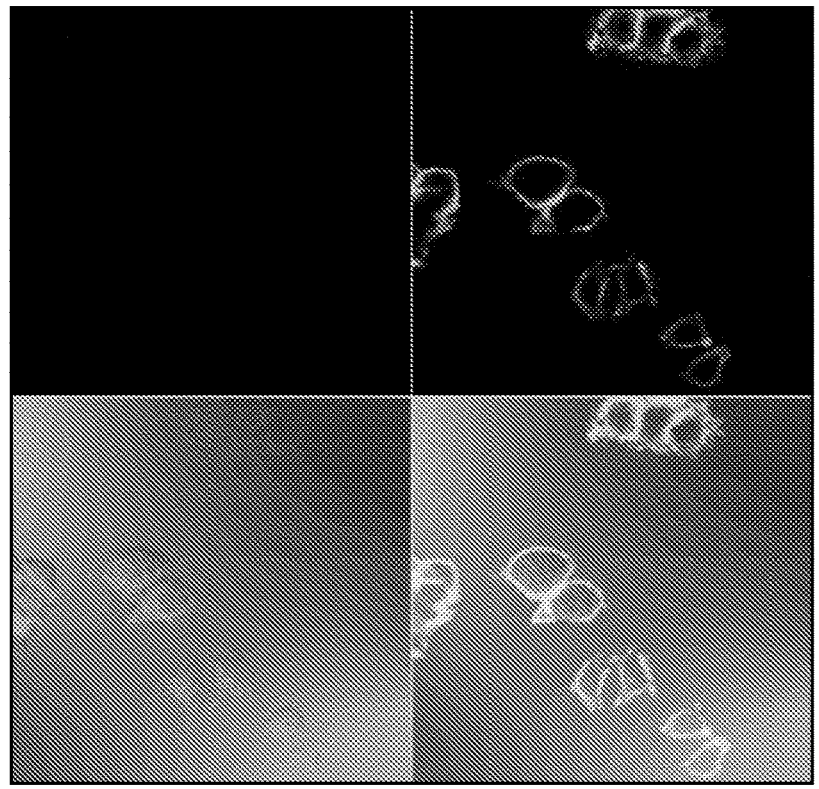
Figure 16:
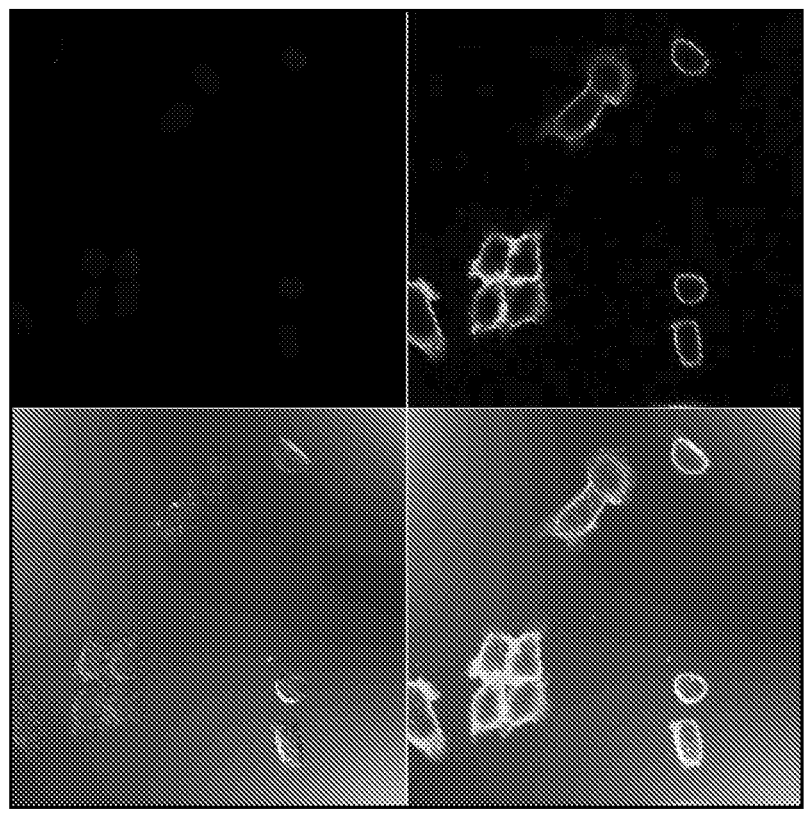
FIG. 16. Confocal fluorescence images of MCF-7 breast cancer cells labeled with (a) PFDPFBT/PS-PEG-COOH/streptavidin probes and (b) PFDPFBT/PS-PEG-COOH/streptavidin probes under 488-nm excitation.
Figure 16:
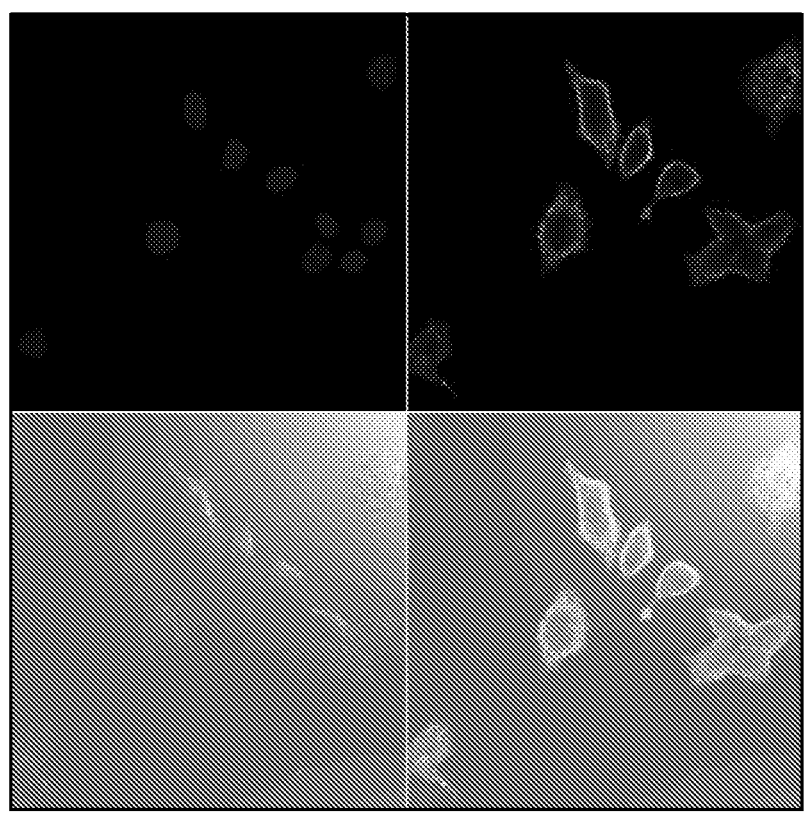

We also studied the Pdot-streptavidin labelled MCF-7 cells with confocal fluorescence imaging (FIG. 15). Again, we did not observe any noticeable non-specific background binding of the Pdots to the cell surface, where cells were incubated with Pdots-streptavidin but without biotinylated primary antibodies. The positive cells were bright and clearly visible. We repeated the experiment with 488-nm excitation (FIG. 16), a commonly used wavelength in bioimaging and flow cytometry, and observed similarly bright cells with no detectable non-specific binding of the Pdots to the cells.

Example 5

Non-Specific Binding Dot Blot Experiment for Fluorinated Pdot (F-Pdot)

Transferrin protein was diluted in TTBS buffer (20 mM Tris, 500 mM NaCl, pH 7.4, 0.05% Tween-20) to the desired concentrations and deposited a 2-µL droplet of this solution onto a dry PVDF membrane. The blot was air-dried for 1.5 hours, after which the membrane was activated by immersion in methanol for 1 min and rinsed off and washed with constant rocking in water and then in TTBS buffer for 2 min each. Then the membrane was blocked to prevent non-specific biding with 3% BSA TTBS (w/v) for 1 hour at room temperature with constant rocking, and washed the PVDF membrane for 2 min with TTBS before finally incubating with ~1 nm Pdot solution in 3% BSA TTBS. The Pdot solutions included F-Pdot, F-Pdot-Strep, C-Pdot and C-Pdot-Strep, respectively. After incubation, the blot was washed in TTBS six times (5 min each) before imaging. The dot blots were imaged in TTBS on a Bio-Rad ChemiDoc MP, where a 302-nm UV lamp was used for excitation and a 530/30 nm bandpass filter was used for emission acquisition. The result was shown in FIG. 18. The F-Pdot was shown to be ~4 times less nonspecific binding than that of C-Pdot. In addition, the F-Pdot-Strep was shown to be ~2 times less nonspecific binding than that of C-Pdot-Strep.

Figure 18:
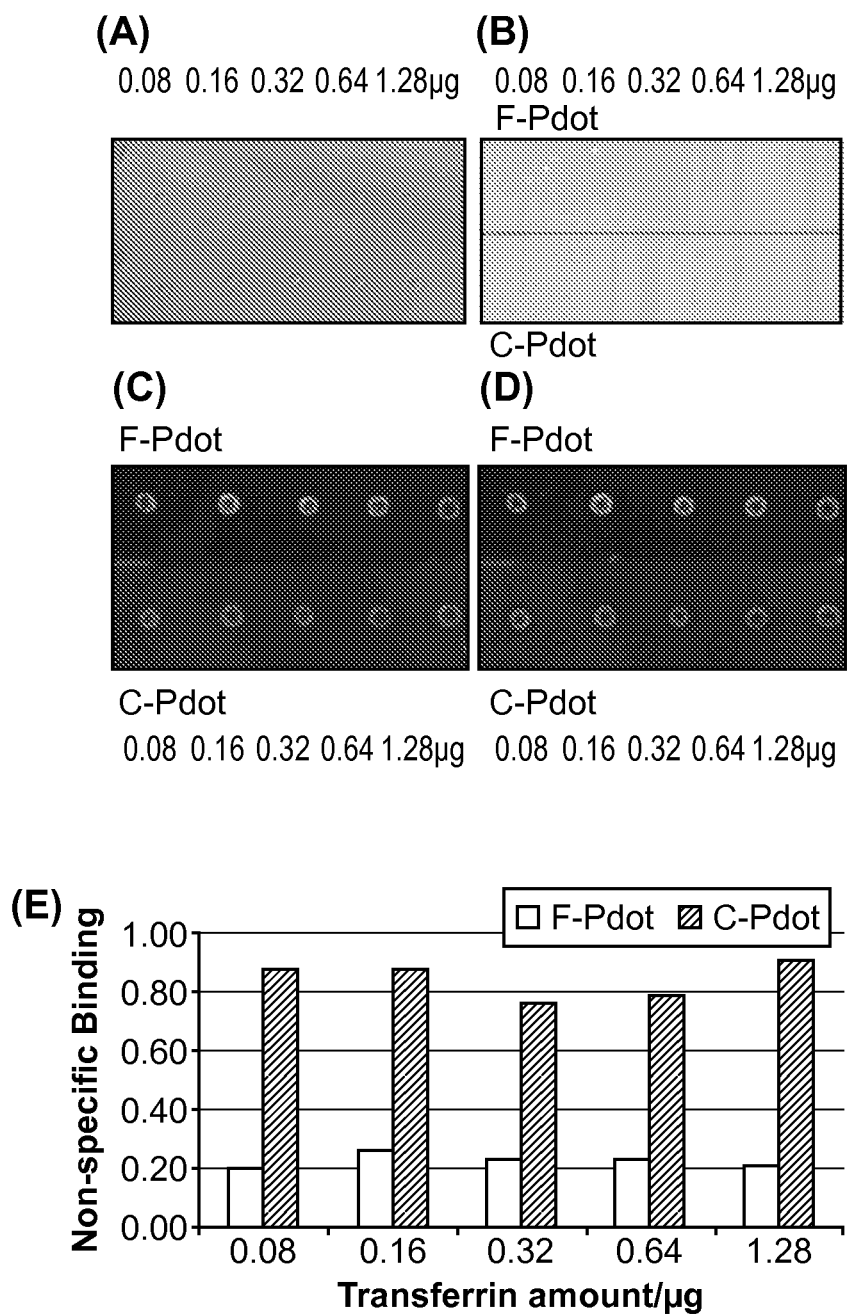
FIG. 18. A dot blot of nonspecific binding of F-Pdot (PFDPFBT), F-Pdot-Strep (PFDPFBT-Streptavidin), C-Pdot (PFDPBT) and C-Pdot-Strep (PFDPBT-Streptavidin) to transferrin protein (from 0.08 μg to 1.28 μg). PFDPFBT/PSPEGCOOH and PFDPBT/PSPEGCOOH Pdots and their bioconjugated probes for cellular imaging were evaluated.
Figure 18:
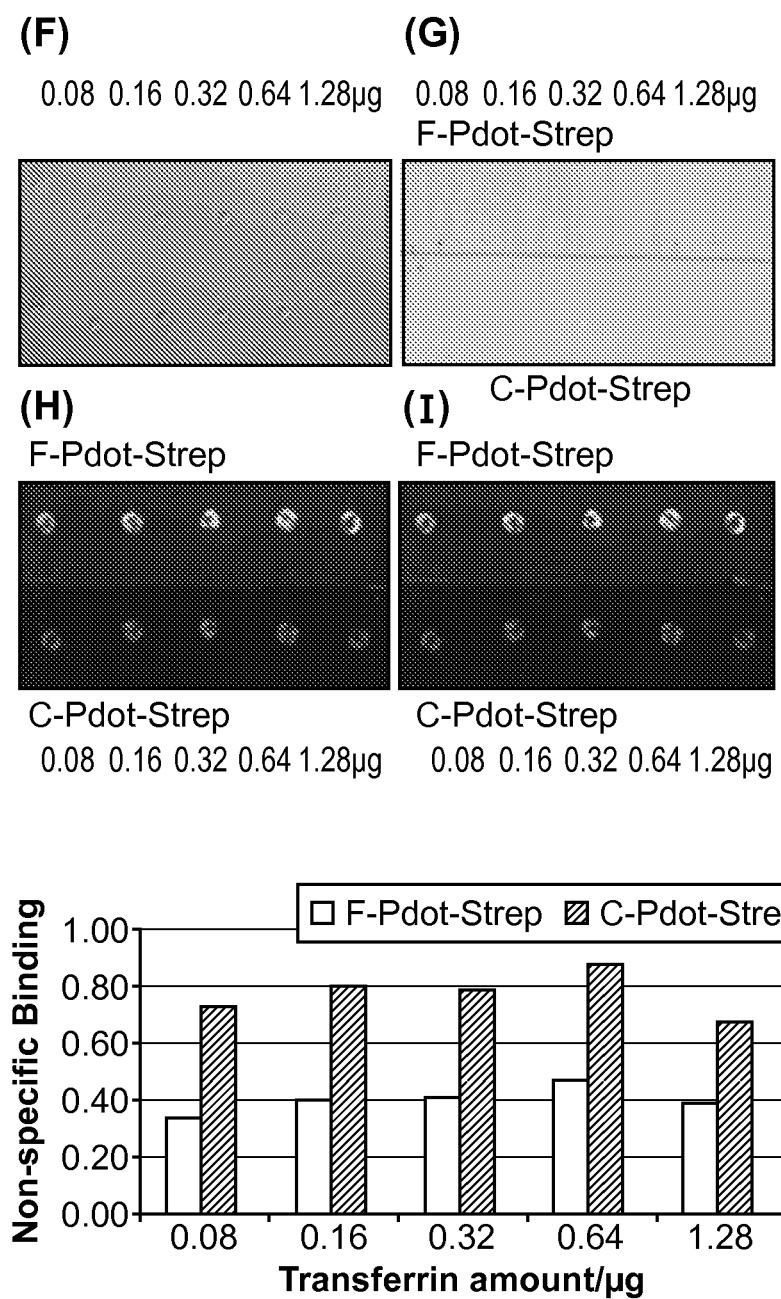
Figure 19:
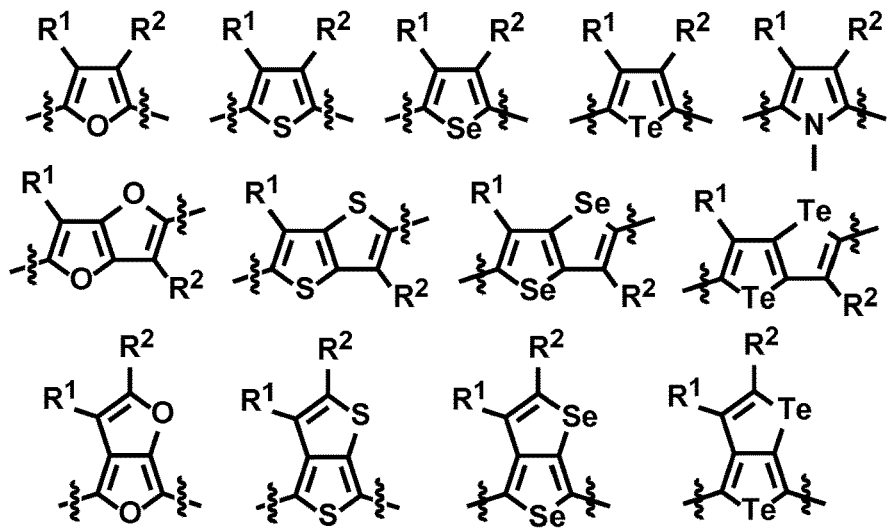
FIG. 19. Example schematic structures of narrow-band acceptors based on furan, thiophene, selenophene, tellurophene, wherein $R^1$ and $R^2$ are independently H and/or F.
Figure 19:
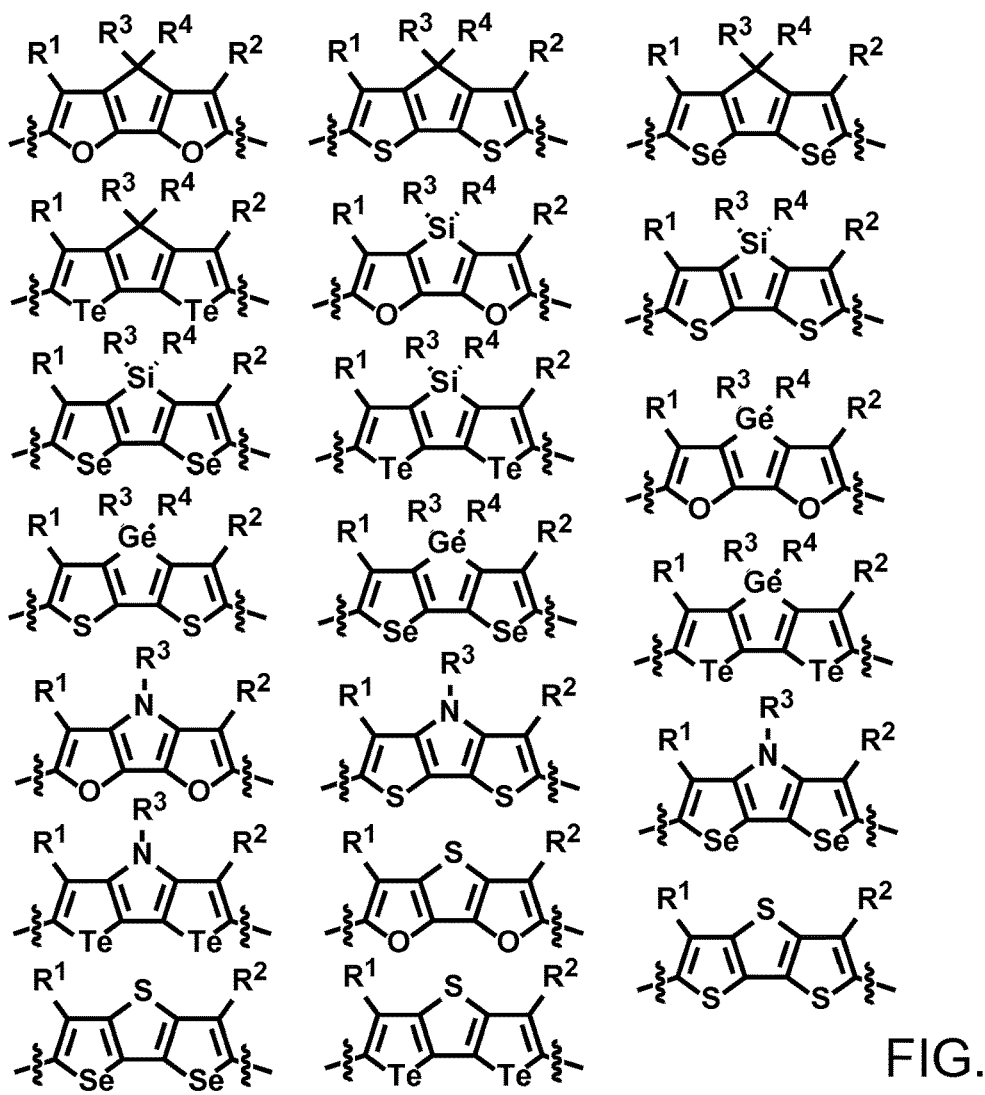
Figure 20:
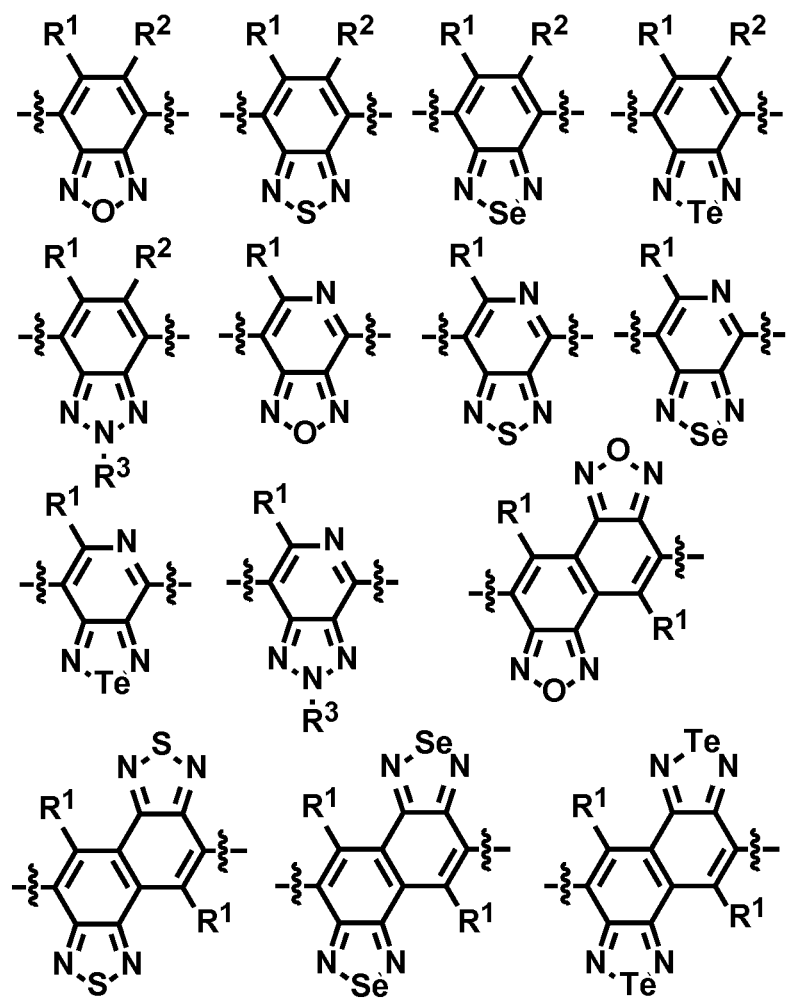
FIG. 20. Example schematic structures of narrow-band acceptors based on benzoxadiazole, benzothiadiazole, benzoselenadiazole, benzotelluradiazole, wherein $R^1$ and $R^2$ are independently H and/or F.
Figure 21:
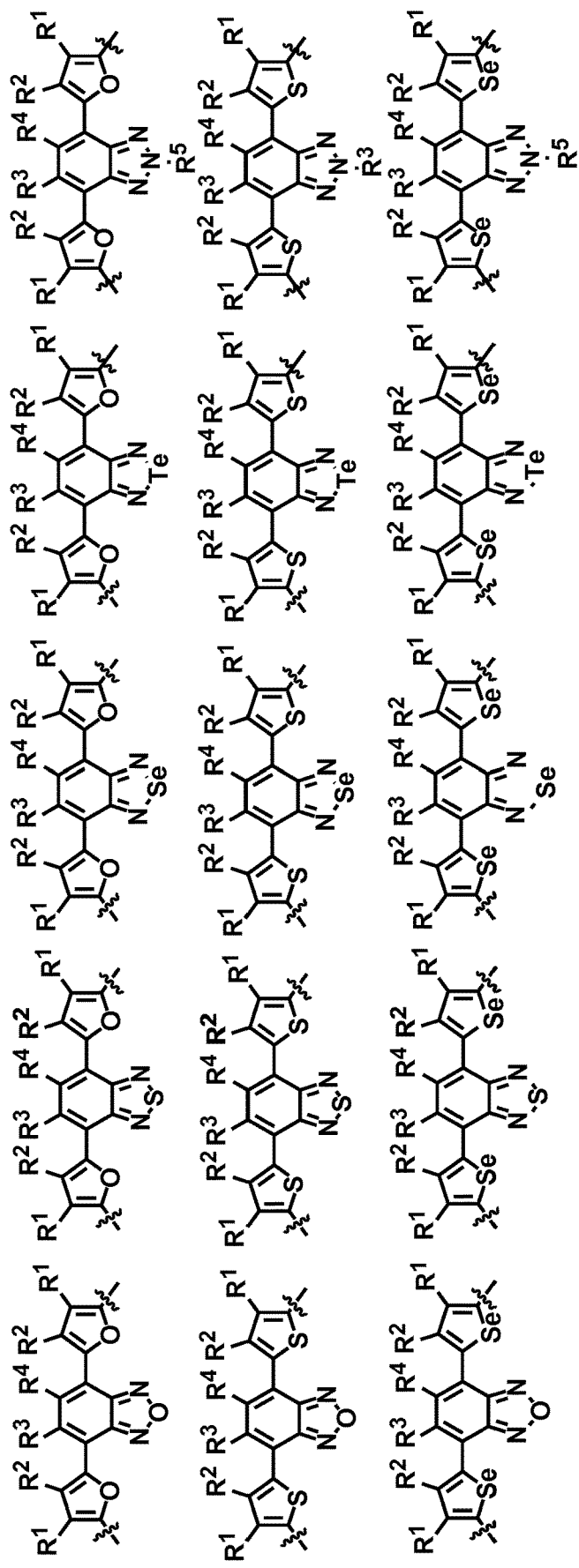
FIG. 21. Example schematic structures of narrow-band acceptors based on benzoxadiazole, benzothiadiazole, benzoselenadiazole, benzotelluradiazole with aromatic substitutes at 4 and 7 positions, wherein $R^1$, $R^2$, $R^3$, $R^4$, $R^5$, $R^6$, $R^7$ are independently H and/or F.
Figure 22:
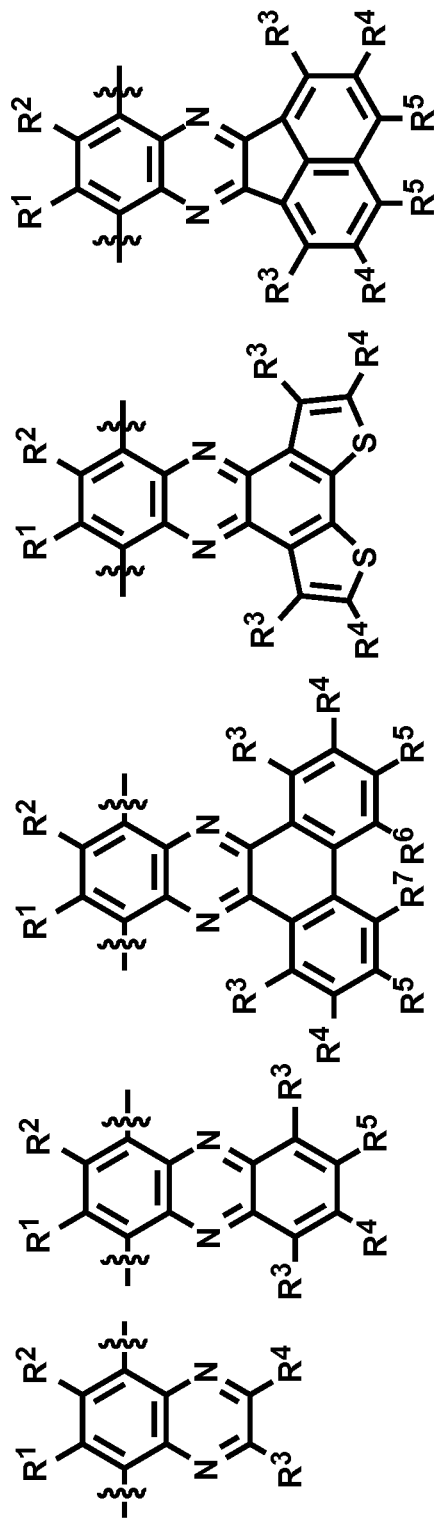
FIG. 22. Example schematic structures of narrow-band acceptors based on quinoxaline units, wherein $R^1$, $R^2$, $R^3$, $R^4$, $R^5$, $R^6$, $R^7$ are independently H and/or F.
Figure 23:
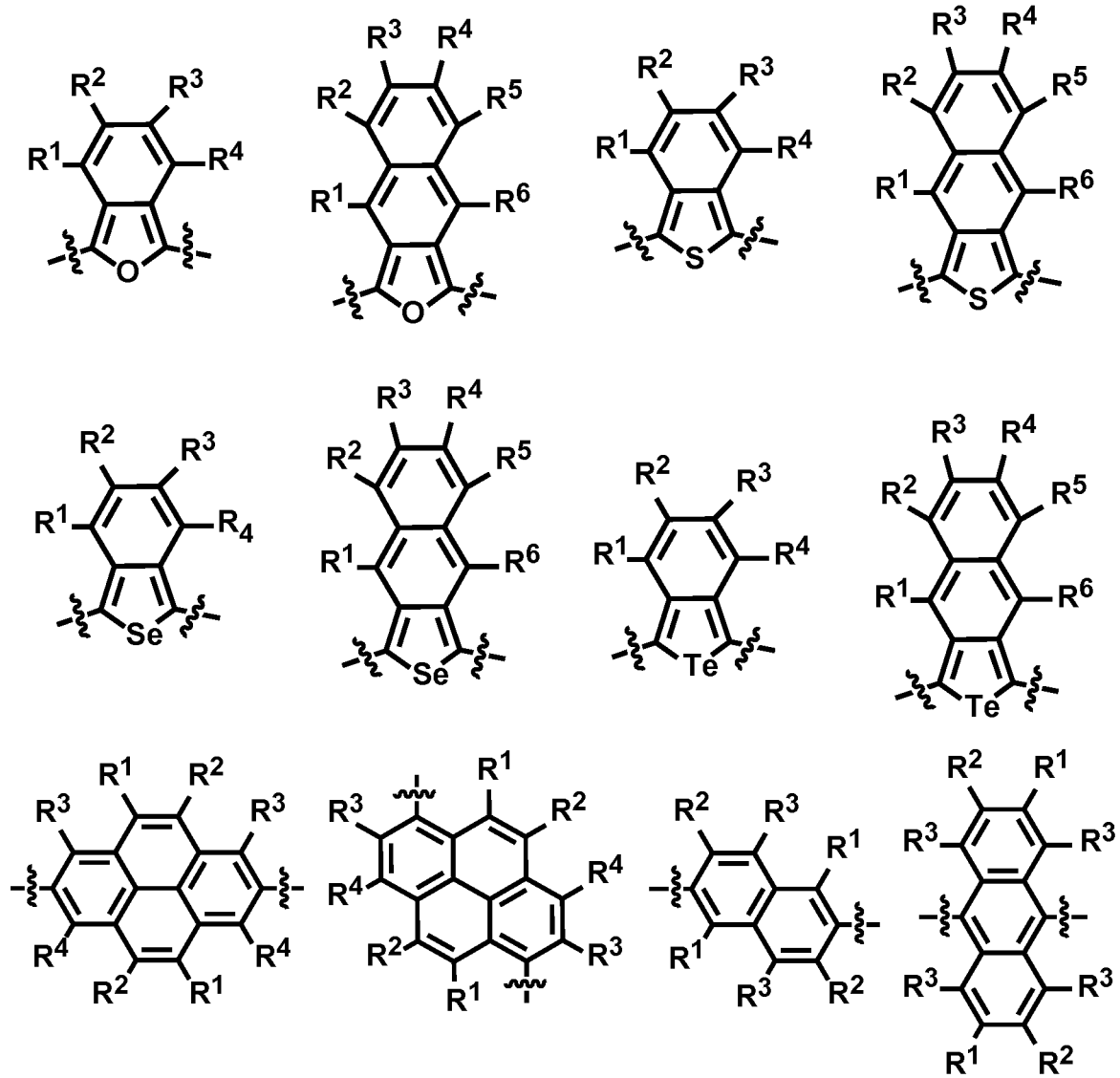
FIG. 23. Example schematic structures of narrow-band acceptors based on pyrene, naphthalene, anthracene units, wherein $R^1$, $R^2$, $R^3$, $R^4$, $R^5$, $R^6$ are independently H and/or F.
Figure 24:
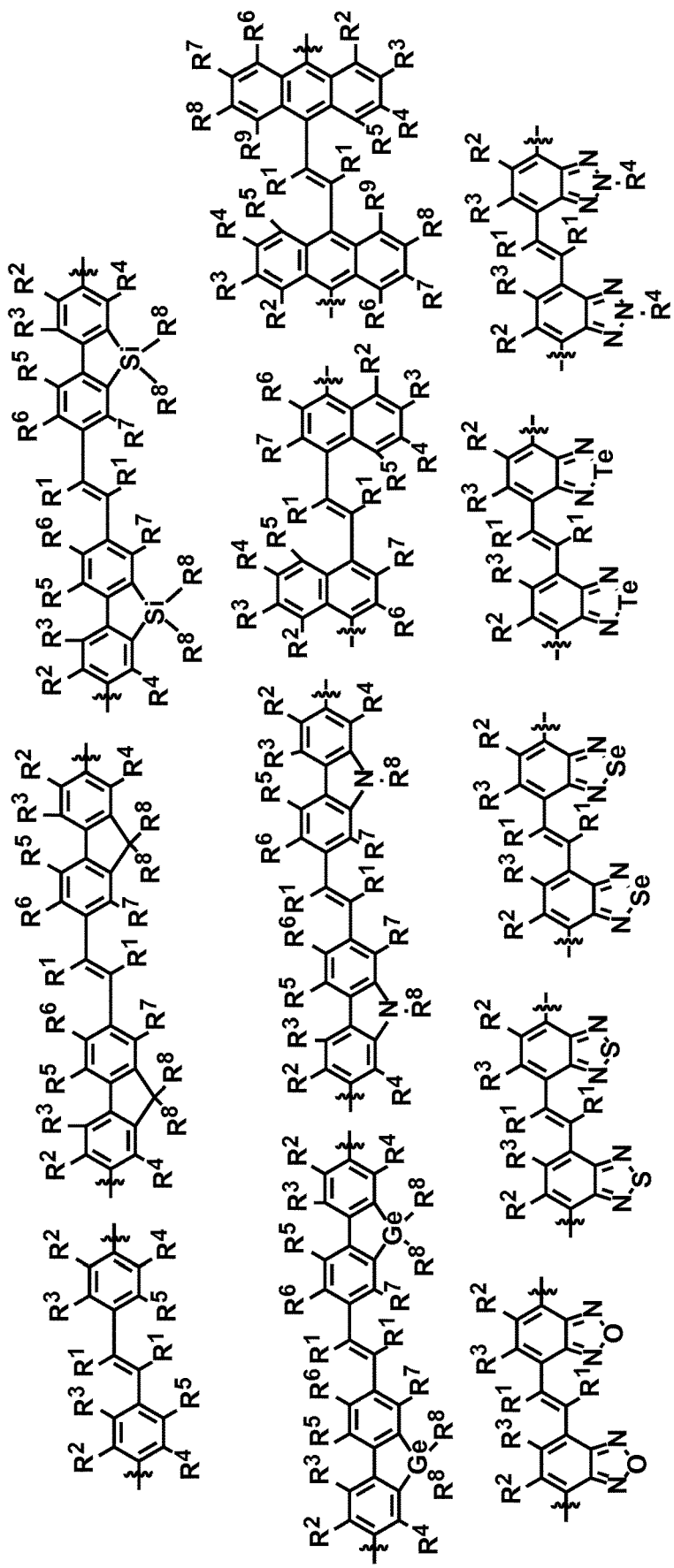
FIG. 24. Example schematic structures of narrow-band acceptors contains the fluorinated vinyl units, wherein $R^1$-$R^5$ is H and/or F.
Figure 25:
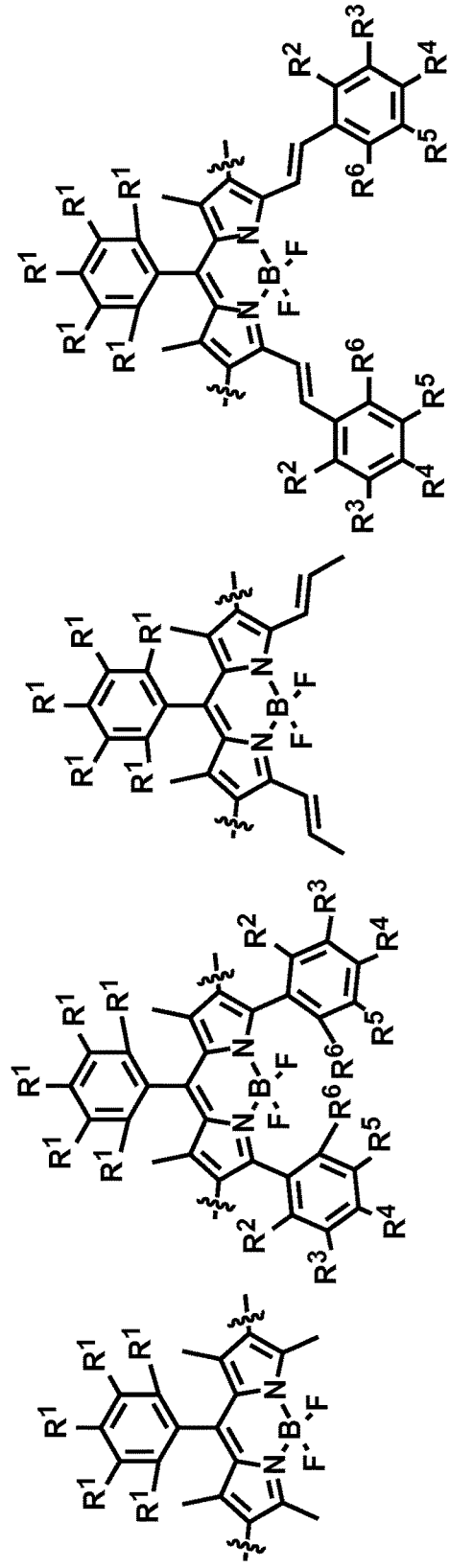
FIG. 25. Example schematic structures of narrow-band acceptors based on boron dipyrromethene complex units, wherein $R^1$-$R^{10}$ is H and/or F.
Figure 25:
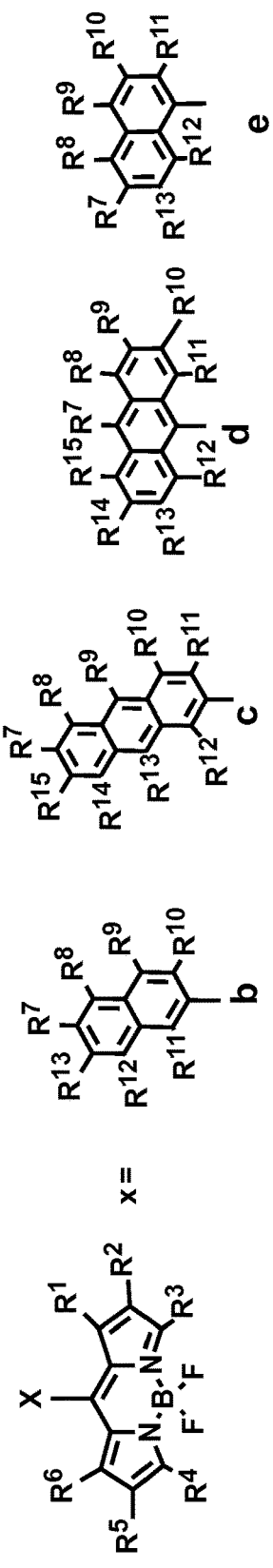
Figure 25:
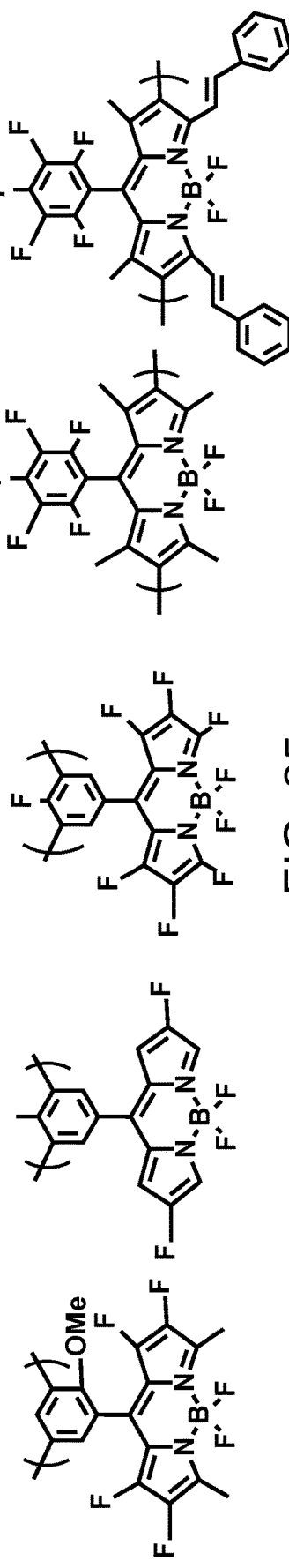
Figure 26:
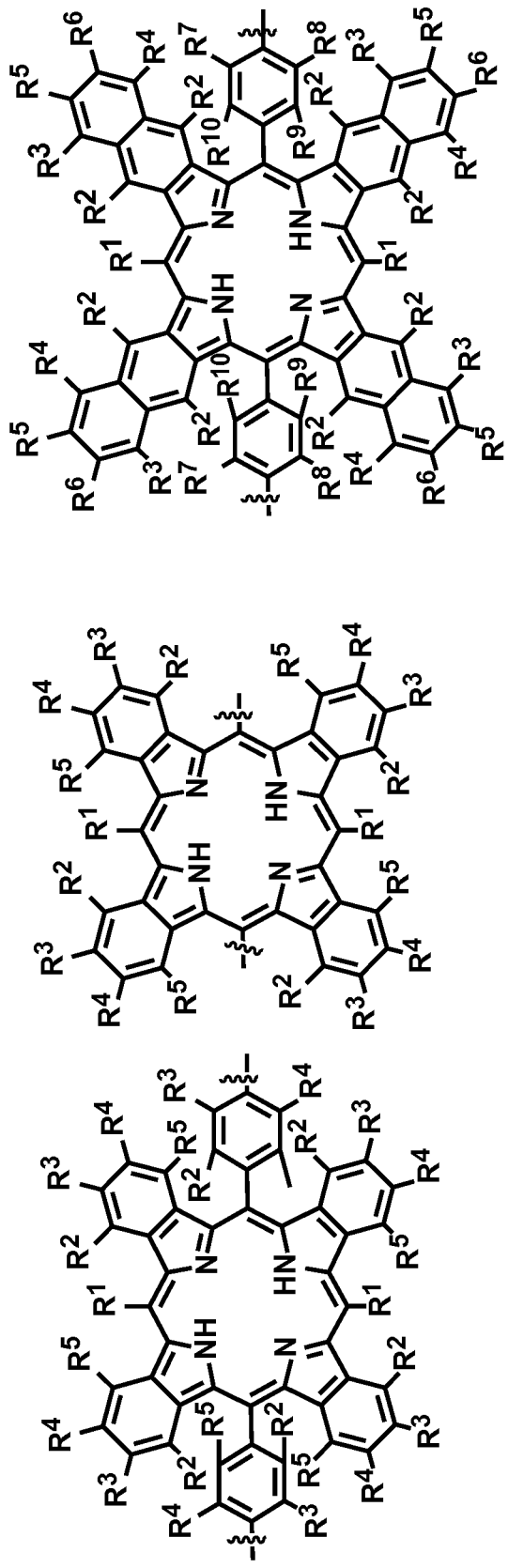
FIG. 26. Example schematic structures of narrow-band acceptors based on porphyrin units, wherein $R^1$-$R^{13}$ is H and/or F.
Figure 26:
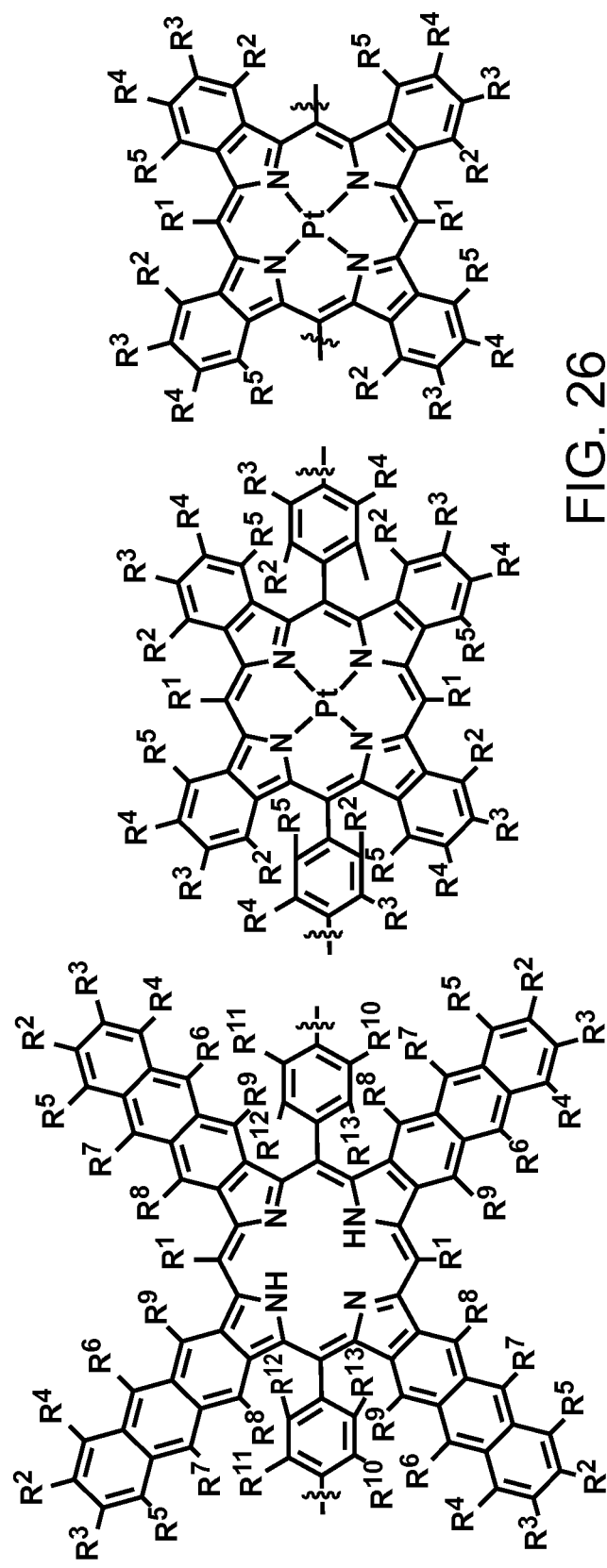
Figure 27:
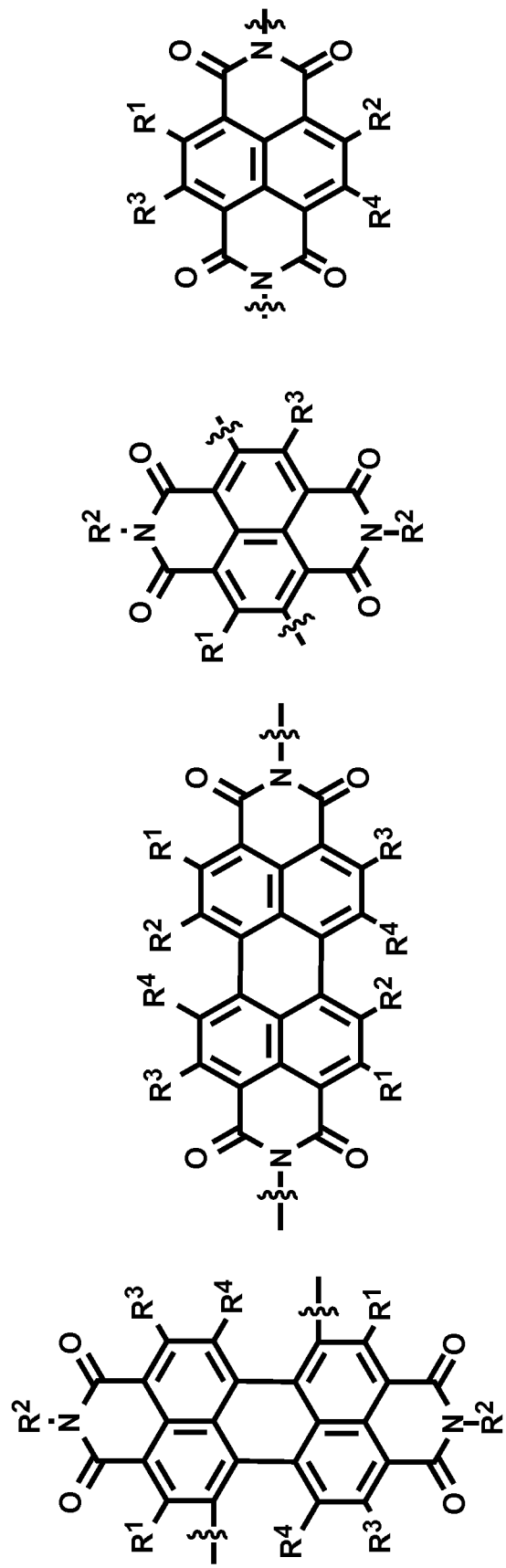
FIG. 27. Examples of schematic structures of narrow-band acceptors based on benzophenanthroline and anthradiisoquinoline units, wherein $R^1$-$R^4$ is H and/or F.
Figure 28:
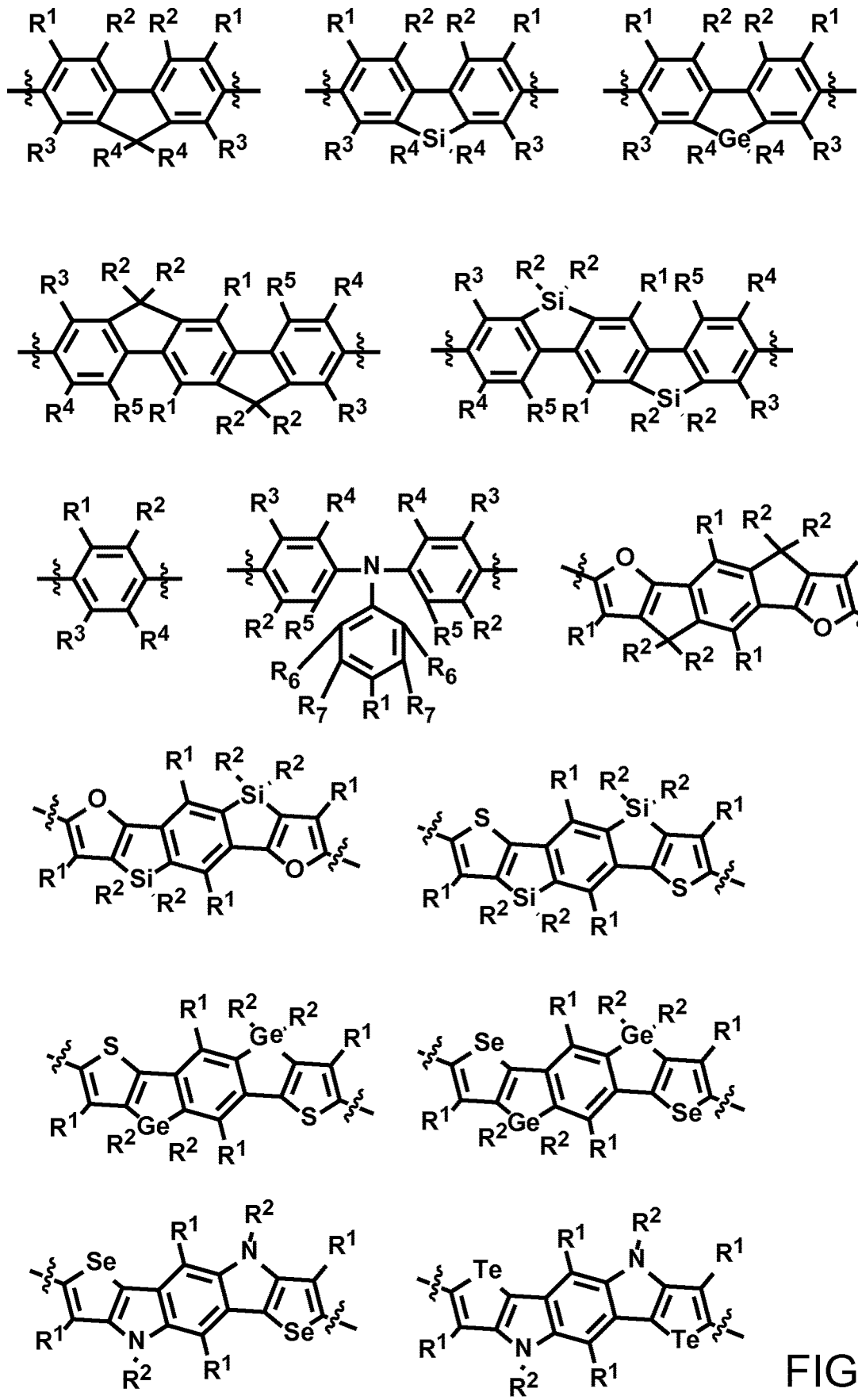
FIG. 28. Example schematic structures of wide band-gap donors, wherein $R^1$-$R^5$ is H and/or F.

A dot blot of nonspecific binding of F-Pdot (PFDPFBT), F-Pdot-Strep (PFDPFBT-Streptavidin), C-Pdot (PFDPBT) and C-Pdot-Strep (PFDPBT-Streptavidin) to transferrin protein (from 0.08 µg to 1.28 µg) in FIG. 18. (A) shows the transferrin protein droplet (2 µl) on PVDF membrane. (B) shows the bright field of the dot blot; (C) shows the UV-excited image of the dot blot; (D) shows the image of Pdot with the circles indicating the area of transferrin protein dot blot, where the integrated fluorescence intensity was calculated; (E) is comparison of the non-specific binding (normalized by the absorption cross section, quantum yield of Pdot and the integrated fluorescence intensity of Pdot from the dot blot) for the F-Pdot and C-Pdot. The non-specific binding of F-Pdot to transferrin is about 4 times less than that of C-Pdot. (F) shows the transferrin protein droplet (2 µl) on PVDF membrane. (G) shows the bright field of the dot blot; (H) shows the UV-excited image of the dot blot; (I) shows the UV-excited image of the dot blot with the circles indicating the area of transferrin protein dot blot, where the integrated fluorescence intensity was calculated; (J) is comparison of the non-specific binding (normalized by the absorption cross section, quantum yield of the Pdot and the integrated fluorescence intensity of Pdot from the dot blot) for the F-Pdot-Strep and C-Pdot-Strep. The non-specific binding of F-Pdot-Strep to transferrin is about 2 times less than that of C-Pdot-Strep.

What is claimed is:

1. A composition comprising a fluorinated semiconducting polymer dot comprising a semiconducting polymer, wherein:

the semiconducting polymer comprises a repeating subunit having a structure

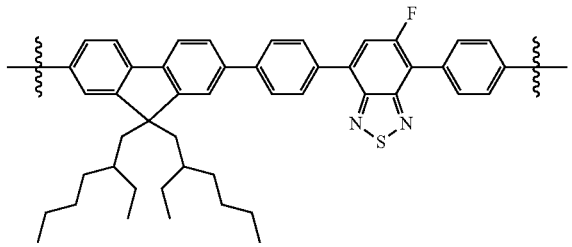

or

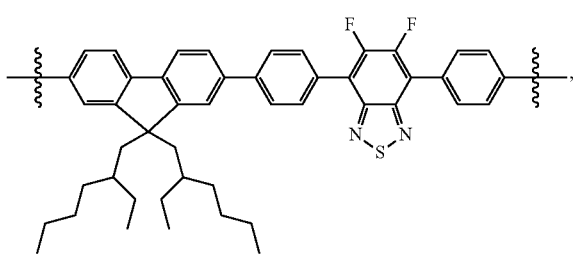

wherein the fluorinated semiconducting polymer dot has a greater quantum yield upon exposure to light than a quantum yield obtained from an analogous non-fluorinated semiconducting polymer dot upon exposure to light; and wherein the fluorinated semiconducting polymer dot has decreased non-specific binding than an analogous non-fluorinated semiconducting polymer dot.

2. The composition of claim 1, wherein the fluorinated semiconducting polymer dot is blended with an amphiphilic polymer.

3. The composition of claim 1, wherein a quantum yield of the fluorinated semiconducting polymer dot is greater than 10%.

4. The composition of claim 1, wherein an absorption peak of the fluorinated semiconducting polymer dot is at a wavelength greater than 350 nm.

5. The composition of claim 1, wherein a photoluminescence peak of the fluorinated semiconducting polymer dot is at a wavelength greater than 410 nm.

6. The composition of claim 1, wherein a size of the fluorinated semiconducting polymer dot is less than 60 nm.

7. The composition of claim 1, wherein the semiconducting polymer has greater than 10 subunits.

8. A composition comprising a fluorinated semiconducting polymer dot comprising a semiconducting polymer, wherein:

the semiconducting polymer comprises a repeating subunit having a structure

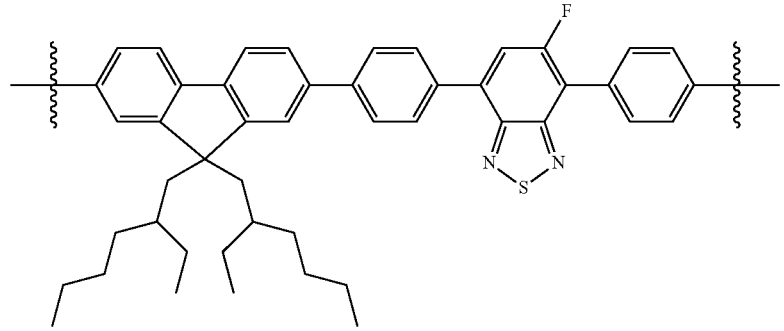

or

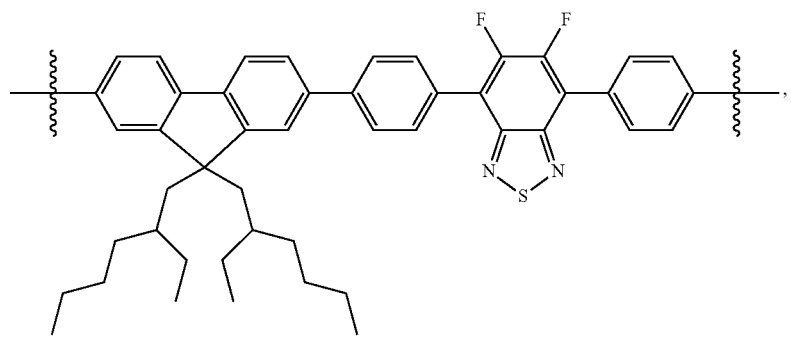

wherein the polymer dot further comprises polystyrene polyethylene glycol carboxylic acid, wherein the fluorinated semiconducting polymer dot has a greater quantum yield upon exposure to light than a quantum yield obtained from an analogous non-fluorinated semiconducting polymer dot upon exposure to light; and wherein the fluorinated semiconducting polymer dot has decreased non-specific binding than an analogous non-fluorinated semiconducting polymer dot.

9. The composition of claim 8, wherein the composition has a quantum yield upon exposure to light that is at least two times greater than a quantum yield obtained from an analogous non-fluorinated semiconducting polymer dot upon exposure to light.

10. The composition of claim 8, wherein the polymer dot comprises a blend of the semiconducting polymer and the polystyrene polyethylene glycol carboxylic acid.

* * * * *